US011963767B2

(12) United States Patent
Bohm et al.

(10) Patent No.: US 11,963,767 B2
(45) Date of Patent: Apr. 23, 2024

(54) ANALYTE SENSOR WITH IMPEDANCE DETERMINATION

(71) Applicant: DexCom, Inc., San Diego, CA (US)

(72) Inventors: Sebastian Bohm, San Diego, CA (US); Anna Claire Harley-Trochimczyk, San Diego, CA (US); Daiting Rong, San Diego, CA (US); Rui Ma, San Diego, CA (US); Wenjie Lan, San Diego, CA (US); Minglian Shi, San Diego, CA (US); Disha B. Sheth, Oceanside, CA (US); Vincent P. Crabtree, San Diego, CA (US); Kamuran Turksoy, Clarksburg, MD (US)

(73) Assignee: Dexcom, Inc., San Diego, CA (US)

( * ) Notice: Subject to any disclaimer, the term of this patent is extended or adjusted under 35 U.S.C. 154(b) by 460 days.

(21) Appl. No.: 16/729,021

(22) Filed: Dec. 27, 2019

(65) Prior Publication Data

US 2020/0209179 A1 Jul. 2, 2020

Related U.S. Application Data

(60) Provisional application No. 62/786,116, filed on Dec. 28, 2018, provisional application No. 62/786,228, (Continued)

(51) Int. Cl.
*A61B 5/1495* (2006.01)
*A61B 5/00* (2006.01)
(Continued)

(52) U.S. Cl.
CPC .......... *A61B 5/1495* (2013.01); *A61B 5/0537* (2013.01); *A61B 5/14532* (2013.01);
(Continued)

(58) Field of Classification Search
CPC . A61B 5/14546; A61B 5/1473; A61B 5/1486; A61B 5/6844; A61B 5/004;
(Continued)

(56) References Cited

U.S. PATENT DOCUMENTS 5,800,420 A 9/1998 Gross et al.
6,001,067 A 12/1999 Shults et al.
(Continued)

FOREIGN PATENT DOCUMENTS

GB 1505343 A 3/1978
JP 2000171431 A 6/2000
(Continued)

OTHER PUBLICATIONS

International Search Report and Written Opinion for Application No. PCT/US2019/068713 dated Apr. 16, 2020, 11 pages.

*Primary Examiner* — Natalie Huls
*Assistant Examiner* — Sharad Timilsina
(74) *Attorney, Agent, or Firm* — Schwegman Lundberg & Woessner, P.A.

(57) ABSTRACT

Various examples described herein are directed to systems and methods of detecting damage to an analyte sensor using analyte sensor impedance values. In some examples, a method of assessing sensor membrane integrity using sensor electronics comprises determining an impedance parameter of an analyte sensor and determining a membrane integrity state of the analyte sensor based on the impedance parameter.

55 Claims, 48 Drawing Sheets

Related U.S. Application Data filed on Dec. 28, 2018, provisional application No. 62/786,127, filed on Dec. 28, 2018, provisional application No. 62/786,166, filed on Dec. 28, 2018, provisional application No. 62/786,208, filed on Dec. 28, 2018.

(51) Int. Cl.

| | | |
|---|---|---|
| A61B 5/0537 | (2021.01) | |
| A61B 5/145 | (2006.01) | |
| A61B 5/1473 | (2006.01) | |
| A61B 5/1486 | (2006.01) | |
| G01N 27/22 | (2006.01) | |
| G01N 27/24 | (2006.01) | |
| G01N 33/487 | (2006.01) | |
| G01N 27/02 | (2006.01) | |

(52) U.S. Cl.
CPC ........ *A61B 5/14546* (2013.01); *A61B 5/1473* (2013.01); *A61B 5/1486* (2013.01); *A61B 5/14865* (2013.01); *A61B 5/6844* (2013.01); *G01N 27/221* (2013.01); *G01N 27/24* (2013.01); *G01N 33/48707* (2013.01); *A61B 5/0004* (2013.01); *A61B 5/0031* (2013.01); *A61B 2560/0223* (2013.01); *A61B 2560/0252* (2013.01); *A61B 2560/0276* (2013.01); *G01N 27/026* (2013.01)

(58) Field of Classification Search
CPC .......... A61B 5/0031; A61B 2560/0223; A61B 2560/0252; A61B 2560/0276; G01N 27/221; G01N 27/24; G01N 33/48707; G01N 27/026
See application file for complete search history.

(56) References Cited

U.S. PATENT DOCUMENTS

| | | | |
|---|---|---|---|
| 6,424,847 | B1 | 7/2002 | Mastrototaro et al. |
| 6,477,395 | B2 | 11/2002 | Schulman et al. |
| 6,484,046 | B1 | 11/2002 | Say et al. |
| 6,512,939 | B1 | 1/2003 | Colvin et al. |
| 6,565,509 | B1 | 5/2003 | Say et al. |
| 6,579,690 | B1 | 6/2003 | Bonnecaze et al. |
| 7,494,465 | B2 | 2/2009 | Brister et al. |
| 8,372,266 | B2 | 2/2013 | Biswas et al. |
| 8,682,408 | B2 | 3/2014 | Boock et al. |
| 8,834,707 | B2 | 9/2014 | Milam et al. |
| 9,044,199 | B2 | 6/2015 | Brister et al. |
| 9,481,917 | B2 | 11/2016 | Bochiechio et al. |
| 9,808,190 | B2 * | 11/2017 | Bohm ................... G01N 33/49 |
| 2002/0098119 | A1 | 7/2002 | Goodman |
| 2003/0191376 | A1 | 10/2003 | Samuels et al. |
| 2005/0027463 | A1 | 2/2005 | Goode et al. |
| 2005/0043598 | A1 | 2/2005 | Goode, Jr. et al. |
| 2006/0020187 | A1 | 1/2006 | Brister et al. |
| 2007/0027385 | A1 | 2/2007 | Brister et al. |
| 2007/0128681 | A1 | 6/2007 | Barman et al. |
| 2007/0197890 | A1 | 8/2007 | Boock et al. |
| 2008/0108942 | A1 | 5/2008 | Brister et al. |
| 2008/0119703 | A1 | 5/2008 | Brister et al. |
| 2008/0156661 | A1 | 7/2008 | Cooper et al. |
| 2010/0196203 | A1 | 8/2010 | Sanghera et al. |
| 2011/0024307 | A1 | 2/2011 | Simpson et al. |
| 2012/0003687 | A1 * | 1/2012 | Toner ................. G01N 33/5005 435/39 |
| 2012/0004524 | A1 | 1/2012 | Van Antwerp et al. |
| 2012/0262298 | A1 | 10/2012 | Böhm et al. |
| 2012/0265037 | A1 | 10/2012 | Bohm et al. |
| 2013/0245981 | A1 | 9/2013 | Estes et al. |
| 2014/0005509 | A1 | 1/2014 | Bhavaraju et al. |
| 2015/0351672 | A1 * | 12/2015 | Vanslyke ............. A61B 5/6898 600/301 |
| 2017/0181672 | A1 | 6/2017 | Nogueira et al. |
| 2017/0184527 | A1 * | 6/2017 | Nogueira ......... G01N 33/48707 |
| 2017/0228345 | A1 | 8/2017 | Gupta et al. |
| 2017/0281092 | A1 | 10/2017 | Burnette et al. |
| 2017/0311852 | A1 | 11/2017 | Morgan |
| 2018/0279928 | A1 | 10/2018 | Previl |
| 2018/0325430 | A1 | 11/2018 | Vaddiraju et al. |
| 2018/0372667 | A1 | 12/2018 | Gupta |
| 2019/0004005 | A1 | 1/2019 | Oja et al. |
| 2019/0227022 | A1 | 7/2019 | Harley-Trochimczyk et al. |

FOREIGN PATENT DOCUMENTS

| | | |
|---|---|---|
| JP | 2015509803 A | 4/2015 |
| WO | 2012154548 A1 | 11/2012 |
| WO | 2019007842 A1 | 1/2019 |

* cited by examiner

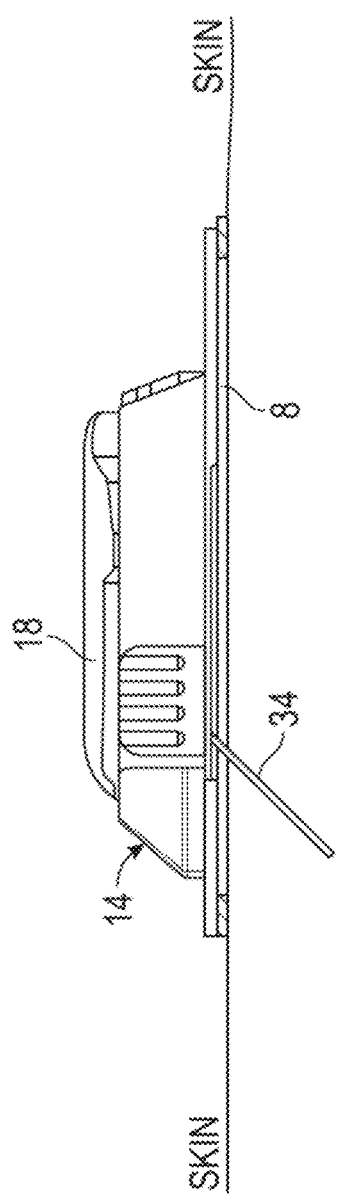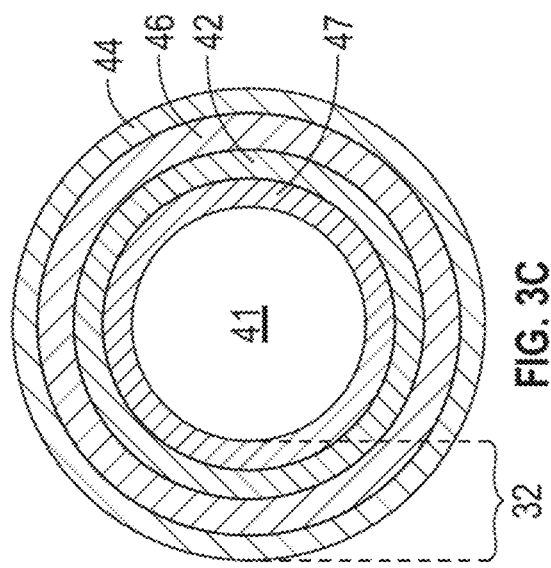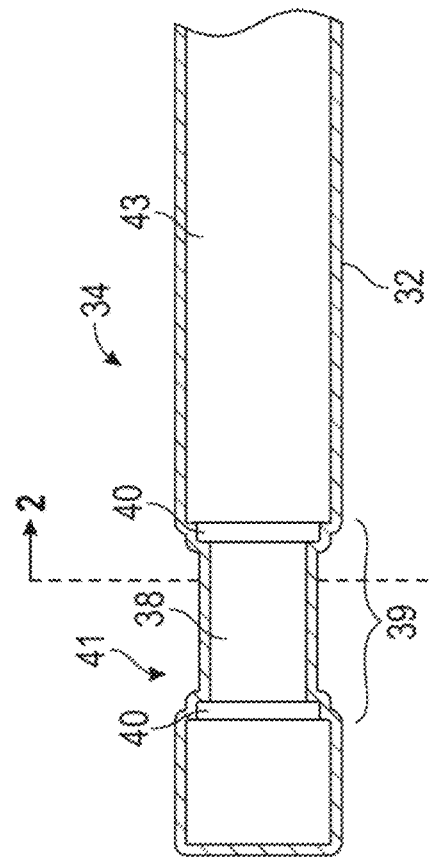

Damage Level 0
(No Damage)

Damage Level 1

Damage Level 4

Damage Level 7

Damage Level 8

|  | MARD Percentiles ||| RMSE (pA/mg/dL) | % RMSE |
| Algo | 2.5%-tile | Median | 97.5%-tile | | |
| FC | 10.21 | 11.66 | 13.38 | 4.88 | 15.36 |
| FC Local | 8.98 | 10.20 | 11.33 | 4.30 | 14.62 |
| Impd | 9.12 | 10.29 | 11.53 | 4.35 | 14.84 |
| Impd+cc | 8.92 | 10.12 | 11.29 | 4.27 | 14.55 |
| Impd+T | 8.70 | 9.87 | 11.14 | 4.28 | 14.60 |
| Impd+T+cc | 8.04 | 9.38 | 10.69 | 4.11 | 13.97 |

ANALYTE SENSOR WITH IMPEDANCE DETERMINATION

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application Ser. No. 62/786,166, filed on Dec. 28, 2018, U.S. Provisional Application Ser. No. 62/786,116, filed on Dec. 28, 2018, U.S. Provisional Application Ser. No. 62/786,208, filed on Dec. 28, 2018, U.S. Provisional Application Ser. No. 62/786,127, filed on Dec. 28, 2018, and U.S. Provisional Application Ser. No. 62/786,228, filed on Dec. 28, 2018. Each of the aforementioned applications is incorporated by reference herein in its entirety, and each is hereby expressly made a part of this specification.

TECHNICAL FIELD

The present development relates generally to medical devices such as analyte sensors, and more particularly, but not by way of limitation, to systems, devices, and methods that use impedance measurements in a continuous glucose monitoring system.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information, such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This present application discloses, among other things, systems, devices, and methods for use of impedance or conductance measurements or estimates in an analyte sensor, such as a glucose sensor.

Example 1 is a method of assessing sensor membrane integrity using sensor electronics may comprise determining an impedance parameter of an analyte sensor and determining a membrane integrity state of the analyte sensor based on the impedance parameter.

In Example 2, the subject matter of Example 1 optionally includes wherein determining the membrane integrity state includes determining whether an impedance condition has been satisfied.

In Example 3, the subject matter of Example 2 optionally includes wherein determining whether the impedance condition has been satisfied includes determining when the impedance parameter is below a specified threshold.

In Example 4, the subject matter of any one or more of Examples 2-3 optionally includes alerting a user to replace a sensor responsive to the impedance condition being satisfied.

In Example 5, the subject matter of any one or more of Examples 1-4 optionally includes wherein determining the membrane integrity state includes determining a level of membrane damage or abnormality.

In Example 6, the subject matter of Example 5 optionally includes compensating an estimated analyte concentration level based at least in part on a determined level of membrane damage or abnormality.

In Example 7, the subject matter of Example 6 optionally includes compensating the estimated analyte concentration level by adjusting a sensitivity value based on the determined level.

In Example 8, the subject matter of any one or more of Examples 1-7 optionally includes determining the impedance parameter at a specified frequency.

In Example 9, the subject matter of Example 8 optionally includes determining the impedance parameter at a frequency above 100 Hz.

In Example 10, the subject matter of Example 9 optionally includes determining the impedance at a frequency between 100 Hz and 10,000 Hz.

In Example 11, the subject matter of any one or more of Examples 1-10 optionally includes the determined impedance parameter being an impedance of the analyte sensor after hydration.

In Example 12, the subject matter of any one or more of Examples 1-11 optionally includes the determined impedance parameter being a determined impedance of a membrane portion of an analyte sensor after hydration.

In Example 13, the subject matter of any one or more of Examples 1-12 optionally includes the determined impedance parameter being based on a comparison of an impedance at a first frequency and an impedance at a second frequency.

In Example 14, the subject matter of Example 13 optionally includes the comparison between an impedance at the first frequency and the impedance at the second frequency becoming stable, after hydration, before the impedance at the first frequency or the impedance at the second frequency becomes stable.

In Example 15, the subject matter of any one or more of Examples 13-14 optionally includes the first frequency and second frequency providing a relatively pronounced impedance difference.

In Example 16, the subject matter of any one or more of Examples 13-15 optionally includes the comparison between the impedance at the frequency and the impedance at the second frequency being a difference between the impedance at the first frequency and the impedance at the second frequency.

In Example 17, the subject matter of any one or more of Examples 13-16 optionally includes wherein the comparison includes determining an existence or amount of a kickback of in a dual frequency impedance vs time relationship.

In Example 18, the subject matter of any one or more of Examples 1-17 optionally includes determining the impedance parameter based on a measurement a specified time after hydration of the sensor.

In Example 19, the subject matter of Example 18 optionally includes the specified time being between 5 and 600 seconds after hydration.

In Example 20, the subject matter of any one or more of Examples 1-19 optionally includes determining the impedance parameter based on a measurement after a measured parameter has reached a steady state condition.

In Example 21, the subject matter of any one or more of Examples 1-20 optionally includes the impedance parameter being a first derivative of impedance with respect to time.

In Example 22, the subject matter of Example 21 optionally includes determining the membrane integrity state based on a shape of a first derivative vs. time curve.

In Example 23, the subject matter of any one or more of Examples 1-22 optionally includes wherein the impedance parameter is a second derivative of impedance with respect to time.

In Example 24, the subject matter of any one or more of Examples 1-23 optionally includes wherein determining the membrane integrity state is based at least in part on a fitted membrane resistance determined using a constant phase element model.

In Example 25, the subject matter of any one or more of Examples 1-24 optionally includes wherein determining a membrane integrity state includes performing a template match.

In Example 26, the subject matter of Example 25 optionally includes determining a best fit from a plurality of templates.

In Example 27, the subject matter of Example 26 optionally includes determining a best fit using dynamic time warping.

Example 28 is an analyte sensor system comprising an analyte sensor sized and shaped for insertion into a host and sensor electronics coupled to the analyte sensor. The sensor electronics may be to determine an impedance parameter of the analyte sensor and determine a membrane integrity state of the analyte sensor based on the impedance parameter.

In Example 29, the subject matter of Example 28 optionally includes the impedance parameter being an impedance value and the sensor electronics determining whether the impedance value is below a threshold, wherein an impedance value below the threshold indicates a presence of damage or abnormality in a sensor membrane portion of the analyte sensor.

In Example 30, the subject matter of any one or more of Examples 28-29 optionally includes the sensor electronics determining a level of membrane damage or abnormality based on the impedance parameter, and compensate an estimated analyte concentration level based at least in part on the level of membrane damage or abnormality.

In Example 31, the subject matter of any one or more of Examples 28-30 optionally includes the sensor electronics determining the impedance parameter by applying a voltage signal at a specified frequency.

In Example 32, the subject matter of Example 31 optionally includes the sensor electronics determining the impedance parameter at frequency between 100 Hz and 10,000 Hz.

In Example 33, the subject matter of any one or more of Examples 31-32 optionally includes the sensor electronics comparing an impedance at a first frequency and an impedance at a second frequency.

In Example 34, the subject matter of Example 33 optionally includes wherein the impedance parameter is a difference between an impedance at a first frequency and an impedance at a second frequency.

In Example 35, the subject matter of any one or more of Examples 33-34 optionally includes the sensor electronics determining an existence or amount of kickback in a dual frequency impedance vs. time relationship; and determining the existence or amount of membrane damage based on the existence or amount of kickback.

In Example 36, the subject matter of any one or more of Examples 28-35 optionally includes the sensor electronics determining a first derivative of impedance with respect to time and determine the membrane integrity state based on a value of the first derivative or a shape of a first derivative vs. time curve.

In Example 37, the subject matter of any one or more of Examples 28-36 optionally includes wherein the sensor electronics determining a second derivative of impedance with respect to time and determining the membrane integrity state based on a value of the second derivative.

In Example 38, the subject matter of any one or more of Examples 28-37 optionally includes the sensor electronics matching an impedance curve to a template.

In Example 39, the subject matter of Example 38 optionally includes the sensor electronics performing dynamic time warping to determine a template match.

Example 40 is a method of operating analyte sensor comprising determining an impedance parameter of an analyte sensor and determining an insertion state of the analyte sensor based on the impedance parameter.

In Example 41, the subject matter of Example 40 optionally includes wherein determining the insertion state includes detecting a dislodgment of a sensor from an insertion position in a host.

In Example 42, the subject matter of Example 41 optionally includes detecting that a sensor has been at least partially pulled out of an initial insertion position.

In Example 43, the subject matter of any one or more of Examples 41-42 optionally includes detecting dislodgement based upon an increase in impedance.

Example 44 is an analyte sensor system comprising an analyte sensor sized and shaped for insertion into a host and sensor electronics coupled to the analyte sensor. The sensor electronics are to determine an impedance parameter of an analyte sensor and determine an insertion state of the analyte sensor based on the impedance parameter.

In Example 45, the subject matter of Example 44 optionally includes the sensor electronics detecting a dislodgement of a sensor based at least in part on an increase in the impedance parameter.

Example 46 is a method of operating an analyte sensor system comprising determining an impedance parameter of an analyte sensor; determining membrane state based on the impedance parameter; and compensating an analyte concentration level based on the membrane state.

In Example 47, the subject matter of Example 46 optionally includes wherein the impedance parameter is an estimated membrane impedance.

In Example 48, the subject matter of any one or more of Examples 46-47 optionally includes wherein the impedance parameter is an impedance at a specified frequency.

In Example 49, the subject matter of any one or more of Examples 46-48 optionally includes wherein the impedance parameter is a dual frequency impedance.

In Example 50, the subject matter of any one or more of Examples 46-49 optionally includes determining when the impedance parameter is in a steady state and compensating based on the impedance parameter in the steady state.

In Example 51, the subject matter of any one or more of Examples 46-50 optionally includes determining an existence or amount of a kickback of in a dual frequency impedance vs. time relationship and determining an amount of compensation based on the existence or amount of kickback.

In Example 52, the subject matter of any one or more of Examples 46-51 optionally includes wherein the impedance parameter is a first derivative of impedance with respect to time.

In Example 53, the subject matter of any one or more of Examples 46-52 optionally includes wherein the impedance parameter is a second derivative of impedance with respect to time.

Example 54 is an analyte sensor system comprising an analyte sensor sized and shaped for insertion into a host and sensor electronics coupled to the analyte sensor. The sensor electronics are to determine an impedance parameter of an analyte sensor and compensate an analyte concentration level based on the impedance parameter to compensate for damage or abnormality in a membrane.

In Example 55, the subject matter of Example 54 optionally includes wherein the impedance parameter is an estimated membrane impedance.

In Example 56, the subject matter of any one or more of Examples 54-55 optionally includes wherein the impedance parameter is an impedance at a specified frequency.

In Example 57, the subject matter of any one or more of Examples 54-56 optionally includes wherein the impedance parameter is a dual frequency impedance.

In Example 58, the subject matter of any one or more of Examples 54-57 optionally includes wherein the impedance parameter is a first derivative of impedance with respect to time.

In Example 59, the subject matter of any one or more of Examples 54-58 optionally includes wherein the impedance parameter is a second derivative of impedance with respect to time.

In Example 60, the subject matter of any one or more of Examples 54-59 optionally includes wherein the sensor electronics determine when the impedance parameter is in a steady state and compensate based on the steady state impedance parameter.

In Example 61, the subject matter of any one or more of Examples 54-60 optionally includes the sensor electronics determining an existence or amount of a kickback of in a dual frequency impedance vs. time relationship and determine an amount of compensation based on the existence or amount of kickback.

Example 62 is a method of calibrating damage to impedance in a population of analyte sensors comprising damaging a first sensor and damaging a second sensor. The method also comprises determining an impedance parameter for the first sensor using a first process and determining an impedance parameter for the second sensor using a second process. The second process may be different than the first process. The method also comprises determining an impedance parameter for a third sensor and estimating a damage state of the third sensor based at least in part on the determined impedance parameter for the first sensor, the determined impedance parameter for the second sensor, and the determined impedance parameter for the third sensor.

In Example 63, the subject matter of Example 62 optionally includes determining a damage curve based at least in part on the determined impedance parameter for the first sensor and the determined impedance parameter for the second sensor and estimating the damage state of the third sensor based upon the determined impedance parameter for the third sensor and the damage curve.

In Example 64, the subject matter of any one or more of Examples 62-63 optionally includes wherein damaging the first sensor comprises scratching the first sensor against an abrasive surface a specified number of times and damaging the second sensor comprises scratching the second sensor against an abrasive surface a specified number of times.

An example (e.g., "Example 9") of subject matter (e.g., a system or apparatus) may optionally combine any portion or combination of any portion of any one or more of Examples 1-8 to include "means for" performing any portion of any one or more of the functions or methods of Examples 1-8.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments described in the present document.

FIG. 3A is an illustration of an example analyte sensor system.

FIG. 3B is an enlarged view of an example analyte sensor portion of the analyte sensor system shown in FIG. 3A.

FIG. 3C is a cross-sectional view of the analyte sensor of FIG. 3B.

FIG. 33G is a table providing MARD Percentiles, RMSE, and % RMSE.

DETAILED DESCRIPTION

Figure 1:
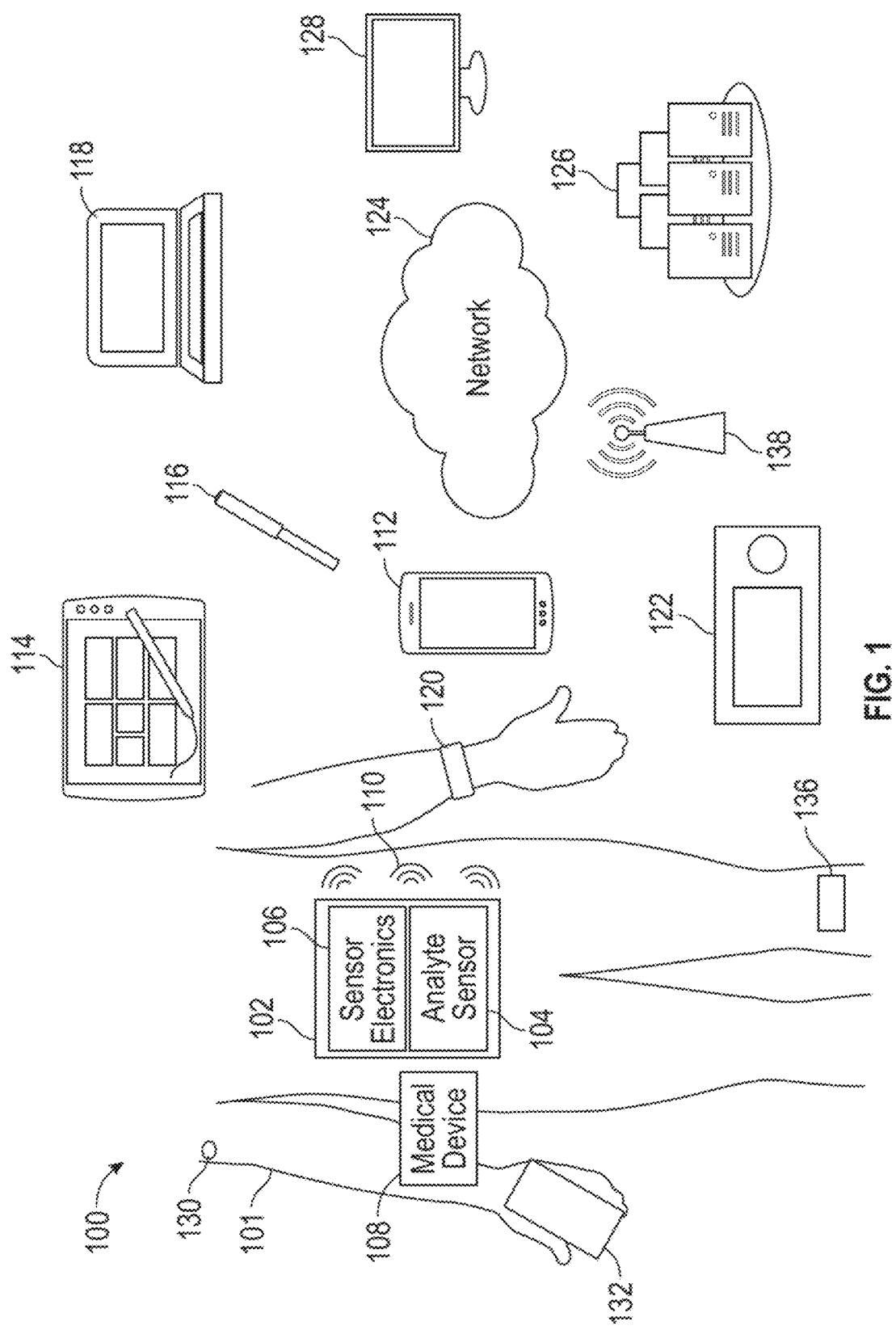
FIG. 1 is an illustration of an example medical device system.

The present inventors have recognized, among other things, that measurements or estimates of impedance in an analyte sensor system may be used to improve the operation of the analyte sensor system. For example, impedance may be used to improve the performance (e.g., accuracy or precision) of an analyte sensor system, or to detect damage or a fault in a sensor. In some examples, an estimate of the impact (e.g., effective capacitance) of a membrane layer interface may be determined.

Overview

An estimate of an impedance of a sensor (e.g., double-layer impedance of a membrane) may be determined using electronic measurements. The impedance estimate may be used, for example, to calibrate a sensor, compensate for drift, identify a damaged sensor, compensate for damage or deviation from a performance standard (e.g., default sensitivity curve).

Impedance may also be used to reduce or eliminate a need for in vivo sensor calibration using blood glucose meter (e.g., "finger stick") data. An analyte sensor, such as a glucose sensor, may be calibrated during manufacture ("factory calibration"), to provide a predictable analyte response curve. For example, a sensor's response to the presence of an analyte (e.g., a glucose concentration) may be checked during (or after) manufacture to assure that the sensor's response to the analyte (e.g., the current signal generated in response to exposure to a known glucose concentration) is within an acceptable range. After implantation in the body, the analyte sensitivity of a sensor is subject to change over time, i.e. "drift." One approach to accounting for in vivo drift is to periodically calibrate the sensor using information from a blood glucose meter (i.e., "finger stick" blood glucose measurements). However, it may be desirable to avoid use of blood glucose meter data or reduce the number or frequency of such in-vivo calibration events. For reasons described in detail below, determining one or more impedance values (e.g., for the circuit 400 shown in FIG. 4) may reduce or eliminate the need to rely on blood glucose meter information. In some examples, impedance may allow for factory calibration, without further in vivo calibration events.

An analyte sensor may include a number of domains or layers, which may include a diffusion resistance domain (e.g., domain 44 shown in FIG. 3C). In a glucose sensor, for example, the diffusion coefficient of electrically neutral glucose molecules in the resistance layer may be a direct correlate or determinant of glucose sensitivity. The electrochemical impedance of the resistance layer is a measure of the mobility of electrically charged ions in the resistance layer. Although the diffusion coefficient and electrochemical impedance are two fundamentally different physical properties associated with two different agents (glucose vs. ions), bench experiments have shown these properties to correlate with each other. As a result, the electrochemical impedance may be used as a surrogate to estimate the diffusion coefficient, which may allow for compensations in in vivo drift of glucose sensitivity. For example, a sensor compensation may be based upon a membrane impedance determined from circuit measurements made in vivo or prior to implantation.

As further described in detail below, the impedance of the membrane (e.g., the electrochemical impedance of the resistance layer) may be determined or estimated based on electrical measurements by sensor electronics or other instrumentation. In various examples, an impedance measurement may be obtained using a sine-wave approach, a step response function approach, or an impulse response function approach. A sine-wave approach may include imposing sinusoidal perturbations in the bias voltage over the RL and measuring the amplitudes of sinusoidal response currents: a scan through a band of frequencies may be performed, and the ratio between the voltage and current excursions may be taken as the impedance at a specific frequency. In step response function approach, a square step change in the bias may be imposed and held, and a perturbation in the sensor current may be measured: the ratio between the Fourier or Laplace transform of the step voltage and that of the transient current is the impedance of the membrane. In an impulse response function approach, a short square wave pulse in the bias voltage may be imposed, and a perturbation in the sensor current may be measured. The impedance may be determined from the current perturbation and the applied bias voltage pulse.

The sensor sensitivity ($m_t$) correlates linearly with the reciprocal of the membrane impedance ($ZRL,t$), i.e. $ZRL,t * m_t$=constant. This relationship can be employed to make use of impedance for estimating in vivo sensitivity in real time:

$$\hat{m}_t = Z_{RL,t}^{-1} \cdot \text{constant}$$

Based on this relationship, a sensor may be calibrated in vivo, which may allow for compensation for drift after deployment in a host.

In some examples, a sensor elapsed time (t) since insertion and an impedance ($R_t$) determined from measurements at the elapsed time may be used as input for a function to estimate sensitivity, e.g., sensitivity ($m_t$) of the sensor may be provided by the function $m_t = f(t)/R_t$. In some examples, an initial calibration curve (CC) may also be used to determine an estimated sensor sensitivity, e.g., $m_t = f(CC, t)/R_t$.

An estimated sensor sensitivity may be used to determine an estimated analyte concentration (e.g., estimated glucose concentration) based upon sensor output (e.g., a current or charge count from a working electrode measured using sensor electronics) and the sensor sensitivity ($m_t$) estimated using the impedance.

Testing and experimentation have been conducted to establish and verify techniques for improving performance of analyte sensor systems, mitigating the effect of double-layer capacitance effects, and detecting, quantifying, or compensating for damage or abnormalities in a sensor membrane. Data, charts, and examples are provided to assist with describing the present subject matter.

Impedance characteristics of a sensor may be used to detect or determine (e.g., quantify) an amount of damage or manufacturing abnormality (e.g., membrane imperfection) in a sensor. A sensor may be functional even though a membrane may include minor imperfections that may be identifiable under a microscope. Some sensors with extensive damage or major manufacturing abnormalities may provide unacceptable performance. Identification of such sensors may provide an opportunity to remove a sensor from circulation or compensate an estimated analyte concentration based on an understanding of impedance characteristics of the sensor. In some examples, a combination of characteristics may be used to assess the integrity of a sensor membrane, e.g., to identify sensors with damage or abnormality, or characterize the extent of sensor abnormality or damage. For example, impedance may be used in combination with dual frequency impedance (e.g., impedance 100 Hz and 1000 Hz), or impedance may be used in combination with an impedance trend or time-based variable (e.g., impedance difference at different points in time), or impedance difference at different frequencies may be used in combination with impedance difference at different points in time (e.g., 72 seconds and 180 seconds or low point and a stable point.) In other examples, other variables, such as signal variability (e.g., perceived noise level), or response to a voltage change (e.g., rate of impedance change) may also be used in combination with any of the above factors and combinations.

In certain situations, such as accidently bumping an analyte sensor, catching a sensor base on an object, or "tenting" of an adhesive patch (e.g., when portions of the adhesive patch are not completely adhered to the skin) to which a sensor is attached, an analyte sensor may be partially pulled out of the skin or otherwise dislodged, which may result in an inaccurate sensor reading. Such an event may be detected based upon a change in impedance.

Sensor impedance may depend on the insertion depth of the sensor into a host. If a sensor is retracted a significant distance, a step change in sensor impedance may be observed.

In an example, an impedance may be measured after insertion, and subsequently measured after insertion. For example, the impedance may be measured recurrently, or may be measured responsive to detection of an event, such as a potential dislodgement event, which may for example be detected using an accelerometer in sensor electronics, or from other sensor information. A sudden change in impedance may indicate dislodgment. For example, a determined impedance change greater than a predetermined impedance change (e.g., in ohms) over a predetermined time period may indicate a dislodgement event. In some examples, a system may declare an alert or raise a "replace sensor" alarm" responsive to detection of a sudden change in impedance.

In some examples, factory calibration may be improved by using impedance for factory calibration. Impedance may be used to determine a calibration value or curve for a sensor, or verification that a sensitivity of the sensor is within acceptable limits. Without use of impedance, calibration may require sequentially exposing a sensor to immersion in fluid baths having varying levels of analyte concentration (e.g., varying glucose concentrations), while applying a bias potential, which may be complicated, time consuming, expensive, or difficult to scale. In some examples, impedance may be used as a replacement (or compliment) to such soaking in analyte solutions.

In an example, a sensor may be pre-soaked in a solution to facilitate measurement of impedance. An impedance measurement may then be made. In an example, the impedance determination (e.g., using current measurements described above) may take one minute, or less, in contrast to a typical one-hour measurement process of current measurements in response to analyte concentrations. This approach may be desirable, for example, because the process does not require application of a bias potential, and a large number of sensors may be soaked simultaneously. In an example, an eight-channel potentiostat may be used to simultaneously measure the impedance of eight sensors on a single fixture. In some examples, the determined impedance values may be used to determine a sensor sensitivity or confirm that the sensor sensitivity or impedance is within defined limits, or to predict drift or later estimate in vivo drift, e.g., using in vivo impedance determinations, which may be compared to the factory impedance values or a default value or range.

In some examples, a sensor may be pre-screened using an impedance procedure, so that damaged sensors may be identified and removed from a production process, which may improve sensor accuracy statistics (e.g., reduce MARD), or improve process efficiency by reducing the number of sensors that proceed through a conventional bath calibration process.

Example System

FIG. 1 is an illustration of an example system 100. The system 100 may include an analyte sensor system 102 that may be coupled to a host 101. The host 101 may be a human patient. The patient may, for example, be subject to a temporary or permanent diabetes condition or other health condition for which analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor 104 may be wearable on the body (e.g., on the body but not under the skin), or the analyte sensor 104 may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor 104 to a host (e.g., an adhesive pad), or a mounting structure configured to receive another component. The system 102 may also include a sensor electronics package, which may include some or all of the sensor electronics 106 shown in FIG. 2. The sensor electronics package may be reusable.

An analyte sensor 104 may use any known method, including invasive, minimally-invasive, or non-invasive sensing techniques (e.g., optically excited fluorescence, microneedle, transdermal monitoring of glucose), to provide a data stream indicative of the concentration of the analyte in a host 101. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host 101).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™, (e.g., the DexCom G5™ sensor or Dexcom G6™ sensor or any variation thereof), from Abbott™ (e.g., the Libre™ sensor), or from Medtronic™ (e.g., the Enlite™ sensor).

In some examples, analyte sensor 104 may be an implantable glucose sensor, such as described with reference to U.S. Pat. No. 6,001,067 and U.S. Patent Publication No. US-2005-0027463-A1, which are incorporated by reference. In some examples, analyte sensor 104 may be a transcutaneous glucose sensor, such as described with reference to U.S. Patent Publication No. US-2006-0020187-A1, which is incorporated by reference. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007, all of which are incorporated by reference. In some examples, the continuous glucose sensor may include a transcutaneous sensor such as described in U.S. Pat. No. 6,565,509 to Say et al., which is incorporated by reference. In some examples, analyte sensor 104 may be a continuous glucose sensor that includes a subcutaneous sensor such as described with reference to U.S. Pat. No. 6,579,690 to Bonnecaze et al. or U.S. Pat. No. 6,484,046 to Say et al., which are incorporated by reference. In some examples, the continuous glucose sensor may include a refillable subcutaneous sensor such as described with reference to U.S. Pat. No. 6,512,939 to Colvin et al., which is incorporated by reference. The continuous glucose sensor may include an intravascular sensor such as described with reference to U.S. Pat. No. 6,477,395 to Schulman et al., which is incorporated by reference. The continuous glucose sensor may include an intravascular sensor such as described with reference to U.S. Pat. No. 6,424,847 to Mastrototaro et al., which is incorporated by reference.

The system 100 may also include a second medical device 108, which may, for example, be a drug delivery device (e.g., insulin pump or insulin pen). In some examples, the medical device 108 may be or include a sensor, such as another analyte sensor 104, a heart rate sensor, a respiration sensor, a motion sensor (e.g. accelerometer), posture sensor (e.g. 3-axis accelerometer), acoustic sensor (e.g. to capture ambient sound or sounds inside the body). In some examples, medical device 108 may be wearable, e.g., on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g., glucose, lactate, insulin or other substance), heart rate, respiration (e.g., using impedance), activity (e.g., using an accelerometer), posture (e.g., using an accelerometer), galvanic skin response, tissue fluid levels (e.g., using impedance or pressure).

The analyte sensor system 102 may communicate with the second medical device 108 via a wired connection, or via a wireless communication signal 110. For example, the analyte sensor system 102 may be configured to communicate using via radio frequency (e.g., Bluetooth, Medical Implant Communication System (MICS), Wi-Fi, NFC, RFID, Zigbee, Z-Wave or other communication protocols), optically (e.g., infrared), sonically (e.g., ultrasonic), or a cellular protocol (e.g., CDMA (Code Division Multiple Access) or GSM (Global System for Mobiles)), or via a wired connection (e.g., serial, parallel, etc.).

The system 100 may also include a wearable sensor 130, which may include a sensor circuit (e.g., a sensor circuit configured to detect a glucose concentration or other analyte concentration) and a communication circuit, which may, for example, be a near field communication (NFC) circuit. In some examples, information from the wearable sensor 130 may be retrieved from the wearable sensor 130 using a user device 132 such as a smart phone that is configured to communicate with the wearable sensor 130 via NFC when the user device 132 is placed near the wearable sensor 130

(e.g., swiping the user device 132 over the sensor 130 retrieves sensor data from the wearable sensor 130 using NFC). The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above,) communication. The additional wearable sensor 130 may be any of the examples described above with respect to medical device 108. The analyte sensor system 102, medical device 108, and additional sensor 130 on the host 101 are provided for the purpose of illustration and description and are not necessarily drawn to scale.

The system 100 may also include one or more peripheral devices, such as a hand-held smart device (e.g., smartphone) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) 126 or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

The system 100 may also include a wireless access point (WAP) 138 that may be used to communicatively couple one or more of analyte sensor system 102, network 124, server system 126, medical device 108 or any of the peripheral devices described above. For example, WAP 138 may provide Wi-Fi and/or cellular connectivity within system 100. Other communication protocols (e.g., Near Field Communication (NFC) or Bluetooth) may also be used among devices of the system 100. In some examples, the server system 126 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100.

Figure 2:
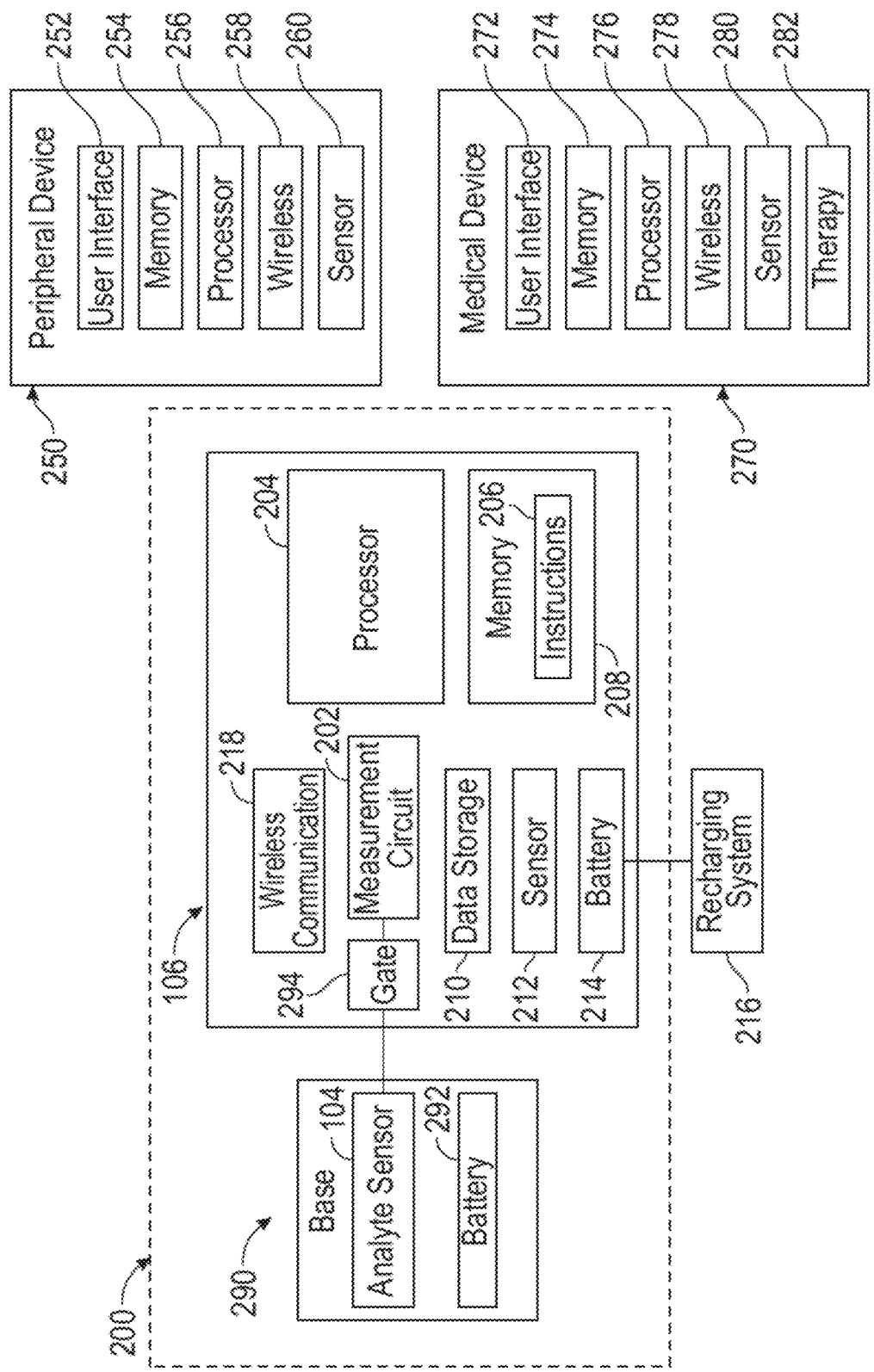
FIG. 2 is a schematic illustration of various example electronic components that may be part of the medical device system shown in FIG. 1.

FIG. 2 is a schematic illustration of various example electronic components that may be part of a medical device system 200. In an example, the system 200 may include sensor electronics 106 and a base 290. While a specific example of division of components between the base 290 and sensor electronics 106 is shown, it is understood that some examples may include additional components in the base 290 or in the sensor electronics 106, and that some of the components (e.g., a battery or supercapacitor) that are shown in the sensor electronics 106 may be alternatively or additionally (e.g., redundantly) provided in the base 290.

In an example, the base 290 may include the analyte sensor 104 and a battery 292. In some examples, the base 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a measurement circuit 202 (e.g., potentiostat), which may be coupled to the analyte sensor 104 and configured to recurrently obtain analyte sensor readings using the analyte sensor 104, for example by continuously or recurrently measuring a current flow indicative of analyte concentration. The sensor electronics 106 may include a gate circuit 294, which may be used to gate the connection between the measurement circuit 202 and the analyte sensor 104. In an example, the analyte sensor 104 accumulates charge over an accumulation period, and the gate circuit 294 is opened so that the measurement circuit 202 can measure the accumulated charge. Gating the analyte sensor 104 may improve the performance of the sensor system 102 by creating a larger signal to noise or interference ratio (e.g., because charge accumulates from an analyte reaction, but sources of interference, such as the presence of acetaminophen near a glucose sensor, do not accumulate, or accumulate less than the charge from the analyte reaction). The sensor electronics 106 may also include a processor 204, which may retrieve instructions 206 from memory 208 and execute the instructions 206 to determine control application of bias potentials to the analyte sensor 104 via the potentiostat, interpret signals from the sensor 104, or compensate for environmental factors. The processor 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor 204. The sensor 212 may be a temperature sensor, accelerometer, or another suitable sensor. The sensor electronics 106 may also include a power source such as a capacitor or battery 214, which may be integrated into the sensor electronics 106, or may be removable, or part of a separate electronics package. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics package (as shown), or in the base 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the processor 204, so that the supercapacitor is prepared for delivery of energy during a subsequent high-load period. In some examples, the supercapacitor may be configured in parallel with the battery 214. A device may be configured to preferentially draw energy from the supercapacitor, as opposed to the battery 214. In some examples, a supercapacitor may be configured to receive energy from a rechargeable battery for short-term storage and transfer energy to the rechargeable battery for long-term storage.

The supercapacitor may extend an operational life of the battery 214 by reducing the strain on the battery 214 during the high-load period. In some examples, a supercapacitor removes at least 10% of the strain off the battery during high-load events. In some examples, a supercapacitor removes at least 20% of the strain off the battery during high-load events. In some examples, a supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor 204 and may be configured to wirelessly communicate with one or more peripheral devices or other medical devices, such as an insulin pump or smart insulin pen.

A peripheral device 250 may, for example, be a wearable device (e.g., activity monitor), such as a wearable device 120. In other examples, the peripheral device 250 may be a hand-held smart device 112 (e.g., smartphone or other device such as a proprietary handheld device available from Dexcom), a tablet 114, a smart pen 116, or special-purpose computer 118 shown in FIG. 1.

The peripheral device 250 may include a user interface 252, a memory circuit 254, a processor 256, a wireless communication circuit 258, a sensor 260, or any combination thereof. The peripheral device 250 may also include a power source, such as a battery. The peripheral device 250 may not necessarily include all of the components shown in FIG. 2. The user interface 252 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as Bluetooth, MICS, or any of the other options described above. The sensor 260 may, for example, include an accelerometer, a temperature sensor, a location sensor, biometric sensor, or blood glucose sensor, blood pressure sensor, heart rate sensor, respiration sensor, or other physiologic sensor. The peripheral device 250 may, for example, be a hand-held smart device 112 (e.g., smartphone or other device such as a proprietary handheld device available from Dexcom), tablet 114, smart pen 116, watch or other wearable device 120, or computer 118 shown in FIG. 1.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

Referring again to FIG. 2, the medical device 270 may include a user interface 272, a memory circuit 274, a processor 276, a wireless communication circuit 278, a sensor 280, a therapy circuit 282, or any combination thereof. The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles)). The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof. In various examples, the medical device 270 may be the medical device 108, peripheral medical device 122, wearable device 120, wearable sensor 130, or wearable sensor 136 shown in FIG. 1.

In examples where the peripheral medical device 122 or medical device 270 is an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receives information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, in the embodiment of FIG. 1, a plurality of different peripheral devices may be in direct wireless communication with a sensor electronics module (e.g., such as an on-skin sensor electronics 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system 102 and relay (i.e., share) information to other devices directly or through a server system (e.g., a network-connected data center) 126.

FIG. 3A is a side view of an analyte sensor system, illustrating an analyte sensor 34 implanted into a host. A mounting unit 14 may be adhered to the host's skin using an adhesive pad 8. The adhesive pad 8 may be formed from an extensible material, which may be removably attached to the skin using an adhesive. The sensor electronics 106 may mechanically couple to the adhesive pad 8.

FIG. 3B is an enlarged view of a distal portion of the analyte sensor 34. The analyte sensor 34 may be adapted for insertion under the host's skin and may be mechanically coupled to the mounting unit 14 and electrically coupled to the sensor electronics 106. The example analyte sensor 34 shown in FIG. 3B includes an elongated conductive body 41. The elongated conductive body 41 can include a core with various layers positioned thereon. A first layer 38 that at least partially surrounds the core and includes a working electrode, for example located in window 39). In some examples, the core and the first layer 38 are made of a single material (such as, for example, platinum). In some examples, the elongated conductive body 41 is a composite of two conductive materials, or a composite of at least one conductive material and at least one non-conductive material. A membrane system 32 is located over the working electrode and may cover other layers and/or electrodes of the sensor 34, as described herein.

The first layer 38 may be formed of a conductive material. The working electrode (at window 39) is an exposed portion of the surface of the first layer 38. Accordingly, the first layer 38 is formed of a material configured to provide a suitable electroactive surface for the working electrode. Examples of suitable materials include, but are not limited to, platinum, platinum-iridium, gold, palladium, iridium, graphite, carbon, a conductive polymer, an alloy, and/or the like.

A second layer 40 surrounds at least a portion of the first layer 38, thereby defining boundaries of the working electrode. In some examples, the second layer 40 serves as an insulator and is formed of an insulating material, such as polyimide, polyurethane, parylene, or any other suitable insulating materials or materials. In some examples, the second layer 40 is configured such that the working electrode (of the layer 38) is exposed via the window 39.

In some examples, the sensor 34 further includes a third layer 43 comprising a conductive material. The third layer 43 may comprise a reference electrode. In some examples, the third layer 43, including the reference electrode, is formed of a silver-containing material that is applied onto the second layer 40 (e.g., an insulator). The silver-containing material may include various materials and be in various forms such as, for example, Ag/AgCl-polymer pasts, paints, polymer-based conducting mixtures, inks, etc.

The analyte sensor 34 may include two (or more) electrodes, e.g., a working electrode at the layer 38 and exposed at window 39 and at least one additional electrode, such as a reference electrode of the layer 43. In the example arrangement of FIG. 1B, the reference electrode also functions as a counter electrode, although other arrangements can include a separate counter electrode. While the analyte sensor 34 may be used with a mounting unit in some examples, in other examples, the analyte sensor 34 may be used with other types of sensor systems. For example, the analyte sensor 34 may be part of a system that includes a battery and sensor in a single package, and may optionally include, for example, a near-field communication (NFC) circuit.

FIG. 3C is a cross-sectional view through the sensor 34 of FIG. 3B on plane 2-2 illustrating a membrane system 32. The membrane system 32 may include a number of domains (e.g., layers). In an example, the membrane system 32 may include an enzyme domain 42, a diffusion resistance domain 44, and a bioprotective domain 46 located around the working electrode. In some examples, a unitary diffusion resistance domain and bioprotective domain may be included in the membrane system 32 (e.g., wherein the functionality of both the diffusion resistance domain and bioprotective domain are incorporated into one domain).

The membrane system 32, in some examples, also includes an electrode layer 47. The electrode layer 47 may be arranged to provide an environment between the surfaces of the working electrode and the reference electrode that facilitates the electrochemical reaction between the electrodes. For example, the electrode layer 47 may include a coating that maintains a layer of water at the electrochemically reactive surfaces of the sensor 34.

In some examples, the sensor 34 may be configured for short-term implantation (e.g., from about 1 to 30 days). However, it is understood that the membrane system 32 can be modified for use in other devices, for example, by including only one or more of the domains, or additional domains. For example, a membrane system may include a plurality of resistance layers, or a plurality of enzyme layers. In some example, the resistance domain 44 may include a plurality of resistance layers, or the enzyme domain 42 may include a plurality of enzyme layers.

The diffusion resistance domain 44 may include a semipermeable membrane that controls the flux of oxygen and glucose to the underlying enzyme domain 42. As a result, the upper limit of linearity of glucose measurement is extended to a much higher value than that which is achieved without the diffusion resistance domain 44.

In some examples, the membrane system 32 may include a bioprotective domain 46, also referred to as a domain or biointerface domain, comprising a base polymer as described in more detail elsewhere herein. However, the membrane system 32 of some examples can also include a plurality of domains or layers including, for example, an electrode domain, an interference domain, or a cell disruptive domain, such as described in more detail elsewhere herein and in U.S. Pat. Nos. 7,494,465, 8,682,408, and 9,044,199, which are incorporated herein by reference in their entirety.

It is to be understood that sensing membranes modified for other sensors, for example, may include fewer or additional layers. For example, in some examples, the membrane system 32 may comprise one electrode layer, one enzyme layer, and two bioprotective layers, but in other examples, the membrane system 32 may comprise one electrode layer, two enzyme layers, and one bioprotective layer. In some examples, the bioprotective layer may be configured to function as the diffusion resistance domain 44 and control the flux of the analyte (e.g., glucose) to the underlying membrane layers.

In some examples, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some examples, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode 30; for example, the enzyme domain 42 deposited over the working electrode does not necessarily need to be deposited over the reference or counter electrodes.

Although the examples illustrated in FIGS. 3B-3C involve circumferentially extending membrane systems, the membranes described herein may be applied to any planar or non-planar surface, for example, the substrate-based sensor structure of U.S. Pat. No. 6,565,509 to Say et al., which is incorporated by reference.

In an example in which the analyte sensor 34 is a glucose sensor, glucose analyte can be detected utilizing glucose oxidase, which produces hydrogen peroxide ($H_2O_2$) as a byproduct of the reaction of glucose with glucose oxidase. The hydrogen peroxide reacts with the surface of the working electrode, producing two protons ($2H^+$), two electrons ($2e^-$) and one molecule of oxygen ($O_2$), which produces an electronic current that may be detected by the sensor electronics 106. The amount of current is a function of the glucose concentration level. A calibration curve may be used to provide an estimated glucose concentration level based on a measured current. The amount of current is also a function of the diffusivity of glucose through the sensor membrane. The glucose diffusivity may change over time, which may cause the sensor glucose sensitivity to change over time, or "drift."

Figure 4:
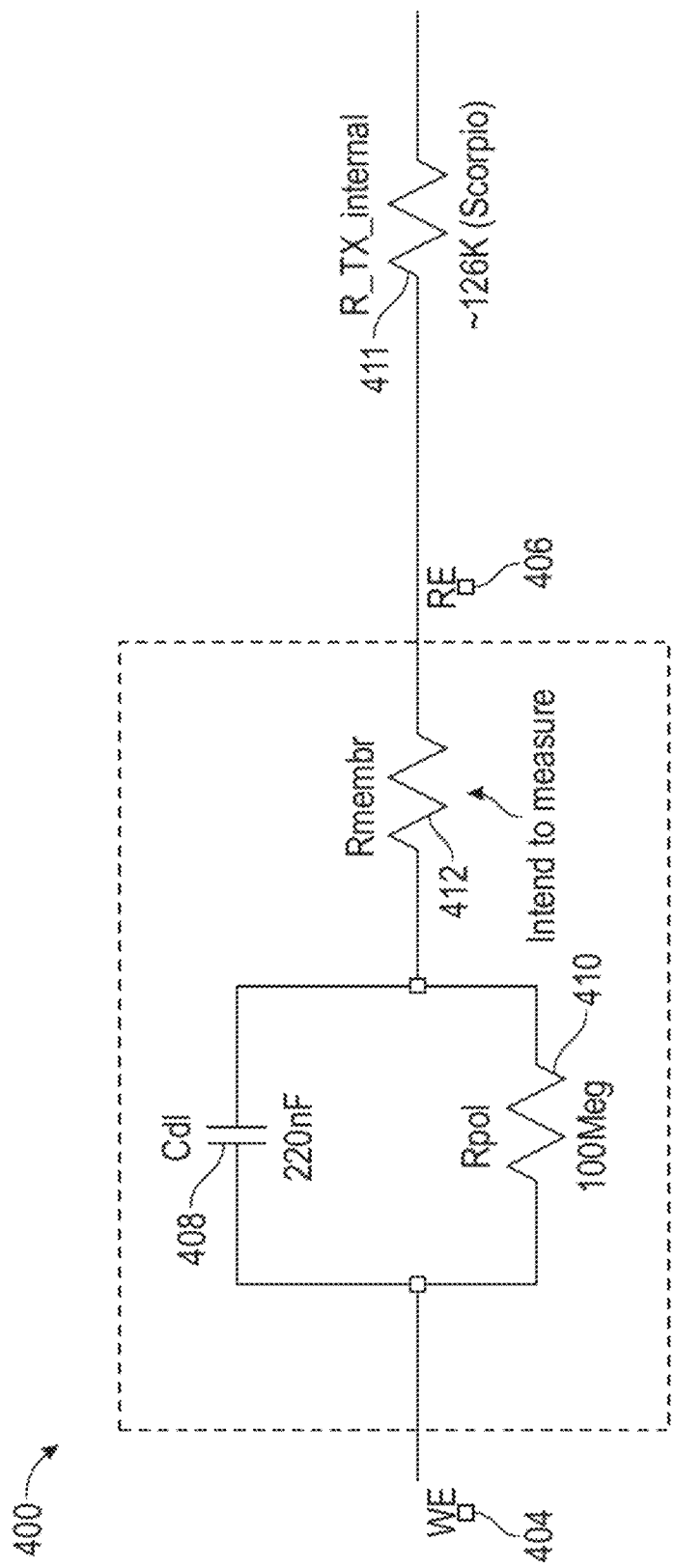
FIG. 4 is a schematic illustration of a circuit that represents the behavior of an analyte sensor.

FIG. 4 is a schematic illustration of a circuit 400 that represents the behavior of an analyte sensor, such as the sensor 34 shown in FIGS. 3A-3C. As described above, the interaction of hydrogen peroxide (generated from the interaction between glucose analyte and glucose oxidase) and working electrode (WE) 404 produces a voltage differential between the working electrode (WE) 404 and reference electrode (RE) 406, which drives a current that may be measured by sensor electronics 106 and used to estimate a glucose concentration level. The circuit 400 also includes a double-layer capacitance (Cdl) 408, which occurs at an interface between the working electrode (WE) 404 and the adjacent membrane (not shown, see description above).

In a typical in vivo analyte sensor, a double-layer capacitance (Cdl) may occur at the interface between the working electrode 404 and the adjacent membrane due to the presence (e.g., during application of an applied voltage between the working electrode 404 and reference electrode) of two layers of ions with opposing polarity. The equivalent circuit 400 may also include a polarization resistance (Rpol) 410, which may be relatively large, and may be modeled, for example, as a static value (e.g., 100 mega-Ohms), or as a variable quantity that varies as a function of glucose concentration level.

An estimated analyte concentration level may be determined based upon A) a measured current (charge) flow through the analyte sensor membrane 412 when a voltage is applied to the sensor circuit and B) a glucose sensitivity of the sensor, which correlates a detected current flow to a glucose concentration level.

The change in glucose diffusivity over time presents a problem, in that two unknown variables (glucose concentration around the membrane 412 and glucose diffusivity in the membrane 412) are present in the system. For example, frequent blood glucose meter calibrations may be used to account for the drift, but this need for meter calibrations may be undesirable for a variety of reasons (e.g., inconvenience to the patient, cost, the potential for inaccurate blood glucose meter data, etc.).

With reference to the equivalent circuit 400, when a voltage is applied across the working and reference electrodes 404 and 406, a current may be considered to flow (forward or backward depending on polarity) through the internal electronics of transmitter (represented by R_Tx_internal) 411; through the reference electrode (RE) 406 and working electrode (WE) 404, which may be designed to have a relatively low resistance; and through the sensor membrane 412 (Rmembr, which is relatively small). Depending on the state of the circuit, current may also flow through, or into, the relatively large polarization resistance 410 (which is indicated as a fixed resistance, but may also be a variable resistance that varies with the body's glucose level, where a higher glucose level provides a smaller polarization resistance), or into the double-layer capacitance 408 (i.e., to charge the double-layer membrane capacitor formed at the working electrode 404), or both.

The impedance (or conductance) of the membrane (Rmembr) 412 is related to electrolyte mobility in the membrane, which is in turn related to glucose diffusivity in the membrane. As the impedance goes down (i.e., conductance goes up, as electrolyte mobility in the membrane 412 goes up), the glucose sensitivity goes up (i.e., a higher glucose sensitivity means that a particular glucose concentration will produce a larger signal in the form of more current or charge flow). Impedance, glucose diffusivity, and glucose sensitivity are further described in U.S. Patent Publication No. US2012/0262298, which is incorporated by reference in its entirety.

Determination of Impedance by Measuring Current or Charge Count.

The relationship between impedance (or conductance) of an analyte sensor circuit and analyte diffusivity (e.g., glucose diffusivity) may allow for determination of an accurate glucose sensitivity based upon a determined impedance value of the sensor circuit. In a situation (e.g., in vivo implantation) where the sensor sensitivity is not precisely known, but impedance can be determined from measurements (e.g., using Ohm's law), a predicted sensitivity may be determined based on a correlation between impedance (or conductivity) and glucose sensitivity.

Figure 5A:
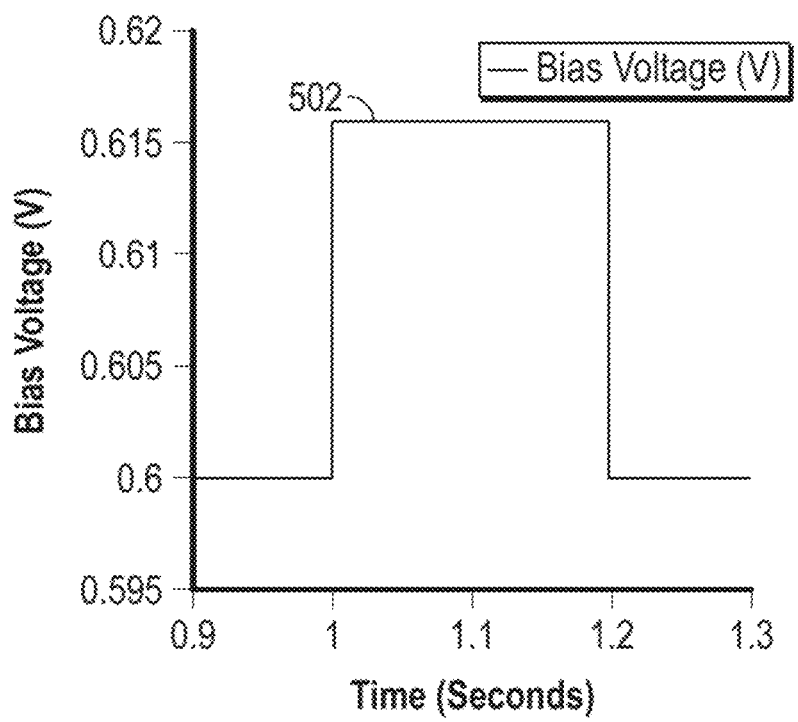
FIG. 5A is a graph that shows a bias voltage step.
Figure 5B:
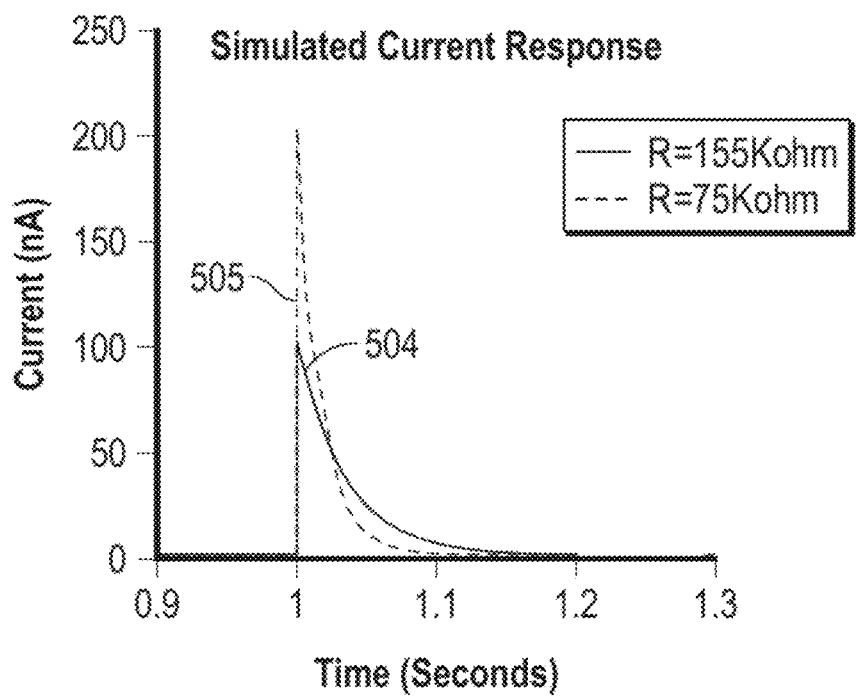
FIG. 5B is a graph that shows a simulated current response to the voltage step shown in FIG. 5A.

In some examples, impedance may be determined based upon application of a known voltage (or voltage step) and measurement of current flow (e.g., integrating charge count over time). In a typical analyte sensor, a sensor bias voltage is applied to a sensor circuit to enable accurate sensing using a sense amplifier. FIG. 5A is a chart that shows a bias voltage 502 stepped up from 0.600 Volts to 0.616 Volts. FIG. 5B shows the corresponding simulated response 504, 505 for a circuit having a 155 kiloohm impedance and a circuit having a 75 kiloohm impedance. As shown in FIG. 5B, the current for the 75 kiloohm circuit rises to a peak current value of over 200 nanoamps, and the response current for the 155 kiloohm circuit rises to about 100 nanoamps. The response current for both circuits then decays as the double-layer capacitance adjusts to the change in applied bias (e.g., as the Cdl in FIG. 4 charges). It should be noted that both FIGS. 5A and 5B illustrate the change in sensor current in response to the transient voltage step. Accordingly, what is shown is the incremental delta current riding on top of an already-existing non-zero glucose current under 0.6V bias.

In a sensor system, a circuit with 155 kiloohm impedance may be differentiated from a circuit with 75 kiloohm impedance based on the magnitude of the current response. In some examples, the impedance may be determined based on the current response, and the resistance attributable to the membrane (Rmembr 412 in FIG. 4) may be determined based upon knowledge (or estimates) of the other impedances in the circuit (e.g., R_TX_internal may be estimated) and Kirchoff's law.

Figure 5C:
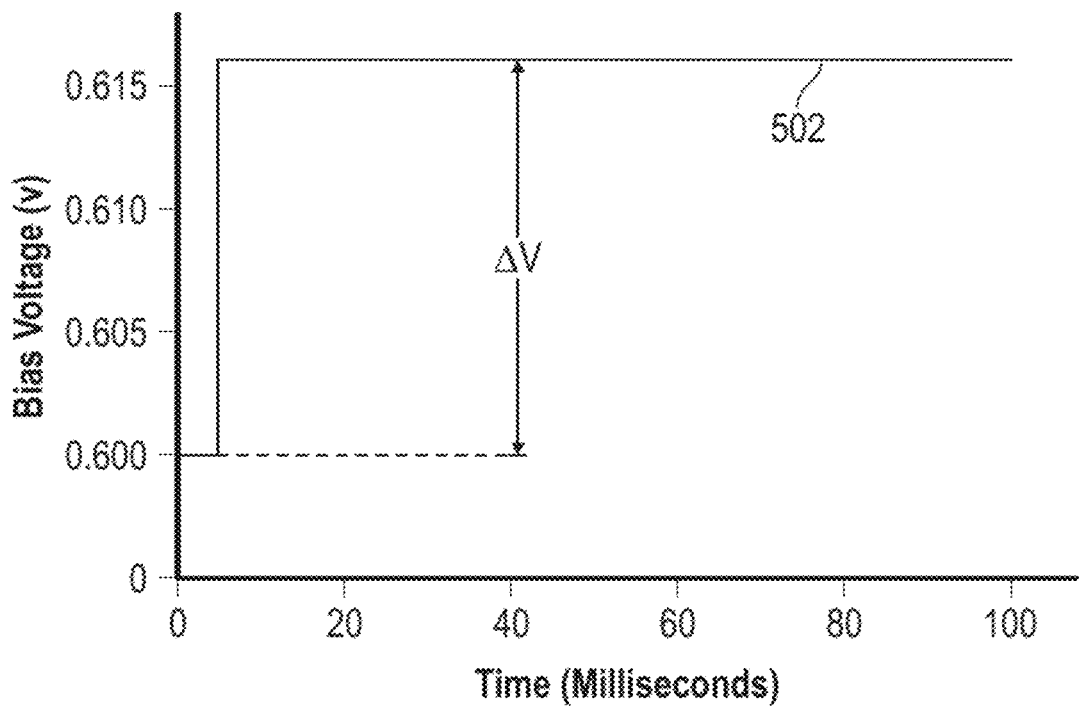
FIG. 5C is a graph that shows the voltage step of FIG. 5A with a time axis in milliseconds.
Figure 5D:
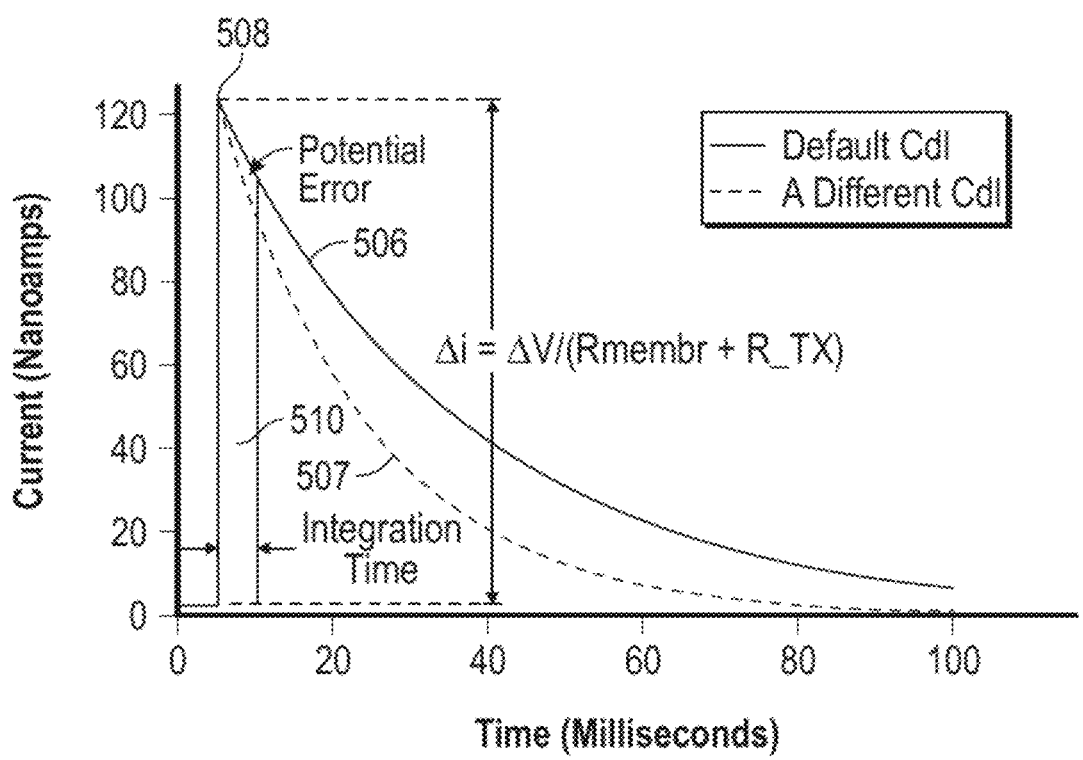
FIG. 5D is a graph that shows the current response to the step of FIG. 5C, with a time axis in milliseconds.

FIG. 5C is a chart that shows a bias voltage 502 stepped up from 0.600 Volts to 0.616 Volts. FIG. 5D shows the current response 506 to the step-up in voltage plotted against time in milliseconds. As shown in FIG. 5D, the sensed current quickly rises to a peak current value 508 (e.g., 120 nA), and then decays as the double-layer capacitance adjusts to the change in applied bias (e.g., as the Cdl 408 in FIG. 4 charges). FIG. 5D also shows a response current 507 for a second sensor with a different double-layer capacitance value, which is described below.

In an analyte sensor, the peak current value 508 may not be measurable directly, but it may be determined by measuring the accumulated charge over an Integration Time 510 (which may, for example, be e.g., 3.9 ms, or a value between 3-5 ms, or a value between 2 and 20 ms, or a value between 2 and 40 ms) after the step-up of the bias voltage, which is the equivalent of integrating under the current response curve for the area A indicated in FIG. 5D.

Simply dividing the integrated current by the specified period of time yields an average current over the integration time, which may be used as an approximation of the peak current, but this approximation is less than the actual peak due to the current decay caused by the double-layer capacitance. A more accurate determination of the peak current may be obtained by assuming a value (e.g., an experimentally determined value) for the double-layer capacitance (Cdl), which allows for derivation of a peak value based upon the integrated current (PI) and the assumed value for Cdl.

Because the capacitance of the membrane (not shown in FIG. 4) may be much smaller than the double-layer capacitance (Cdl), the polarization resistance (Rpol) may be very high (>1 megaOhm), and the capacitive resistance of the membrane is initially very large after the voltage step, substantially all of the current flows through Rmembr 412 and Cdl 408. In a short period (e.g., 5 ms) after the voltage step, the total sensor resistance may be estimated as the membrane resistance (Rmembr 412). The membrane resistance (Rmembr 412) may thus be estimated using Ohm's law: $\Delta i=\Delta V/(Rmembr+R\_TX)$. After the peak current is determined (e.g., based up integrated charge for a short period after the voltage step), this equation may be solved for the resistance of the membrane (Rmembr 412).

An estimate of the integrated pulse current may be obtained by integrating over a small portion of the current decay curve, as shown for example, in FIG. 5D. An integration over a short integration time after the voltage step may be used to estimate peak current. The integration time may be relatively short compared to the time it takes the current response to a step voltage to decay (i.e., compared to the capacitor charge time for the double-layer capacitor after application of the step in bias voltage). For example, an integration time of four milliseconds (4 ms) may be used to estimate peak current. Other important parameters may include the rise time of the voltage step (or bias pulse), the impedance of sensor electronics (which may be measured and consistently controlled in manufacturing), the pulse potential (e.g., a 16 mV step may be applied), and alignment of the current integration with the rising edge of the voltage step (which may be controlled by a clock in the sensor electronics, e.g., the start of the current integration may be one clock cycle after the beginning of a voltage step), and duty cycle (e.g., a five percent duty cycle may be used to allow a sensor membrane capacitance to discharge to a consistent pre-pulse state). In some examples, a voltage step may be applied before each glucose measurement, or recurrently (e.g., before every second glucose measurement, or every third, fourth, or fifth glucose measurement, or once an hour, or once or twice or more times per day).

Figure 5E:
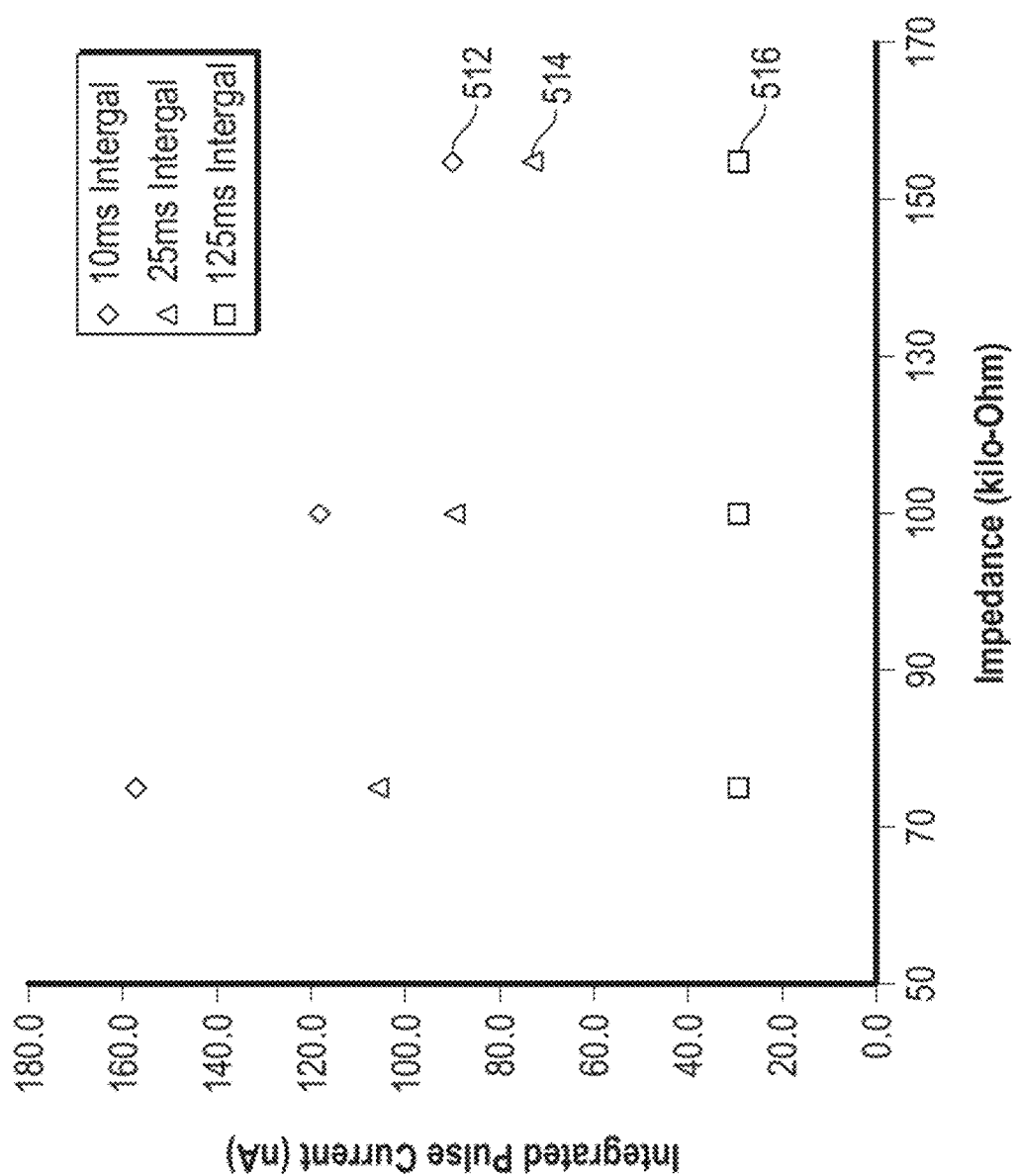
FIG. 5E is a graph that shows integrated pulse current plotted against impedance for three different integration times.

FIG. 5E shows integrated pulse current 512, 514, 516 plotted against impedance for three different integration times (10 milliseconds, 25 milliseconds, and 125 milliseconds). For the 125 millisecond integration time, the integrated pulse current is approximately the same for three different impedance values (75 kOhm, 110 kOhm, 155 kOhm). Because the current is averaged over all or most of the current decay curve (i.e., the current reaches or approaches zero (or a baseline current) within 125 ms), the sensor circuits with different impedances all result in an integrated pulse current of about 30 nanoamps. This approximate equivalence in integrated pulse current for the three different impedance values would prevent determination of an accurate impedance estimate from the integrated pulse currents. In contrast, an integration time of 25 milliseconds results in different values of integrated pulse current for the three different impedance values. As a result, a sensor that integrates over a 25 millisecond integration time would allow for differentiation between sensor circuits having 75 kOhm, 110 kOhm, 155 kOhm impedance values or estimation of an impedance based on integrated pulse current. Using a 10 millisecond integration time provides even greater variation in integrated pulse current for different impedance values, which would improve performance in determining an impedance estimate.

While the description above in some instances discloses absolute current and absolute voltage, it is understood that the methods may also be used with respect to a change in current ($\Delta i$), change in voltage ($\Delta V$), or change in impedance ($\Delta R$). For example, in some analyte sensors, the baseline current may not be zero, because of the presence of a steady bias voltage.

Figure 5F:
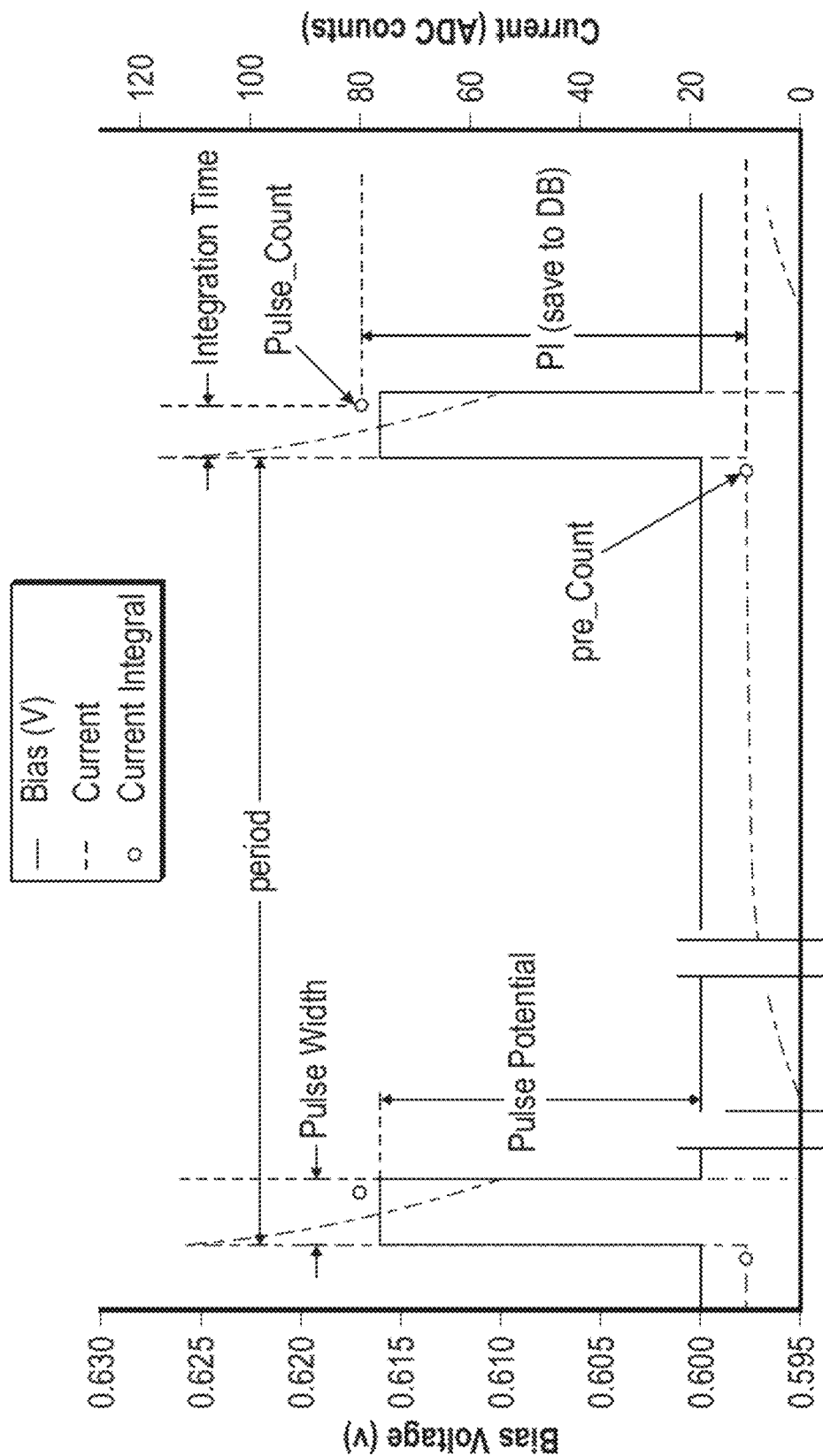
FIG. 5F is a graph that shows bias voltage overlaid onto the current response to a voltage step.

In some examples, a step voltage may be recurrently (e.g., periodically) applied to a sensor circuit. The step voltage may be maintained for a period that is as long or longer than the entire current decay curve, as shown in FIG. 5C, or the step voltage may be returned to a baseline value before the current has decayed to a steady state value, as shown in FIG. 5F. FIG. 5F shows bias voltage overlaid onto the current response to a voltage step ("Pulse Potential"). The step voltage step (e.g., increased from 0.600 Volts to 0.616) may be applied and maintained for a segment of time (Integration Time), and the bias voltage may then be returned to the level it was at prior to the step (e.g., returned to 0.600 Volts). A Current Integral for the Integration Time may be determined based on a difference in a charge count (e.g., obtained using a Coulomb counter) between a count value (Pulse_Count) at the end of the Integration Time and a count value (Pre_Count) at the beginning of the Integration Time. The Current Integral amounts to an accumulated charge for the pulse (PI), which may be stored in a database (DB) for comparison with past or future impedance values or may be used in a compensation algorithm to provide a more accurate estimated analyte concentration value.

When the bias voltage returns to its normal baseline level (e.g., when the Integration Time period expires and the bias voltage drops from 0.616 Volts back to 0.600 Volts), the capacitor begins to discharge (to move back to a 0.6 Volt charge state), and the observed current drops below the baseline value (because the capacitor is supplying some of the potential to maintain the bias voltage). Eventually, the current transitions back to its baseline (steady state) value.

After a period of time has expired, a second voltage step may be applied, and a second PI value may be determined in the manner described above.

Averaging of charge count values over multiple sampling periods.

Figure 6A:
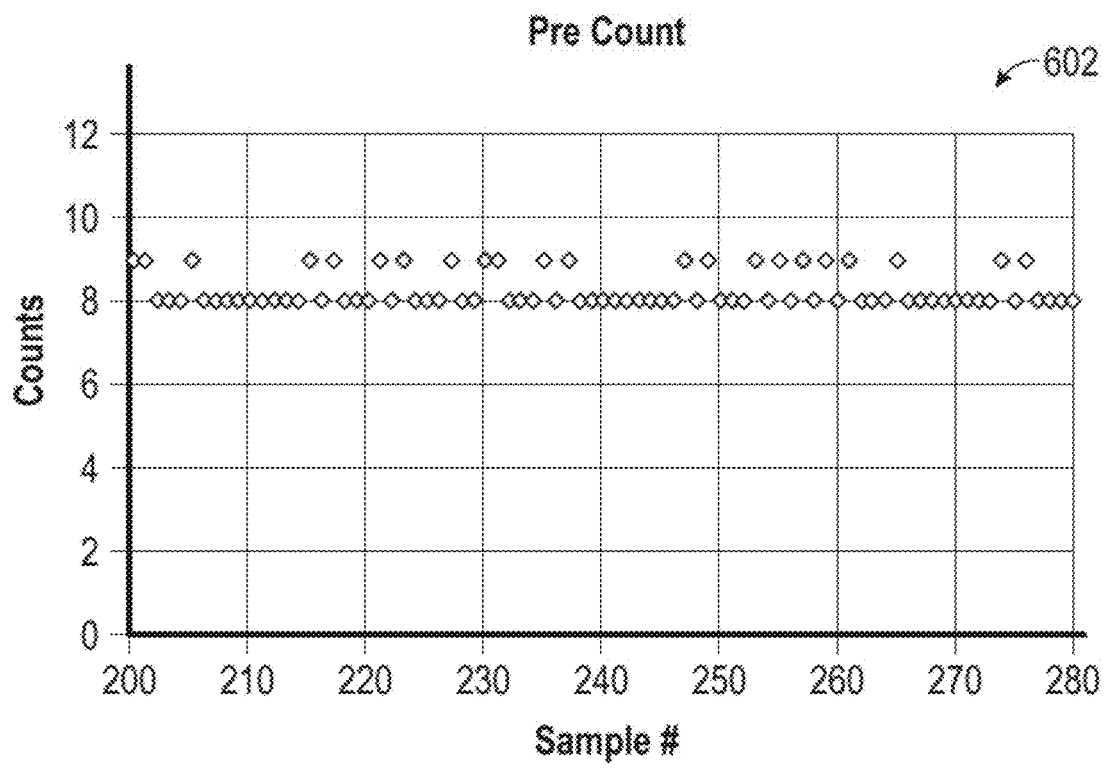
FIG. 6A is a graph that shows count values at the beginning of the Integration Time (Pre_Count) and at the end of the Integration Time (Pulse_Count) for a plurality of samples by a sensor.
Figure 6B:
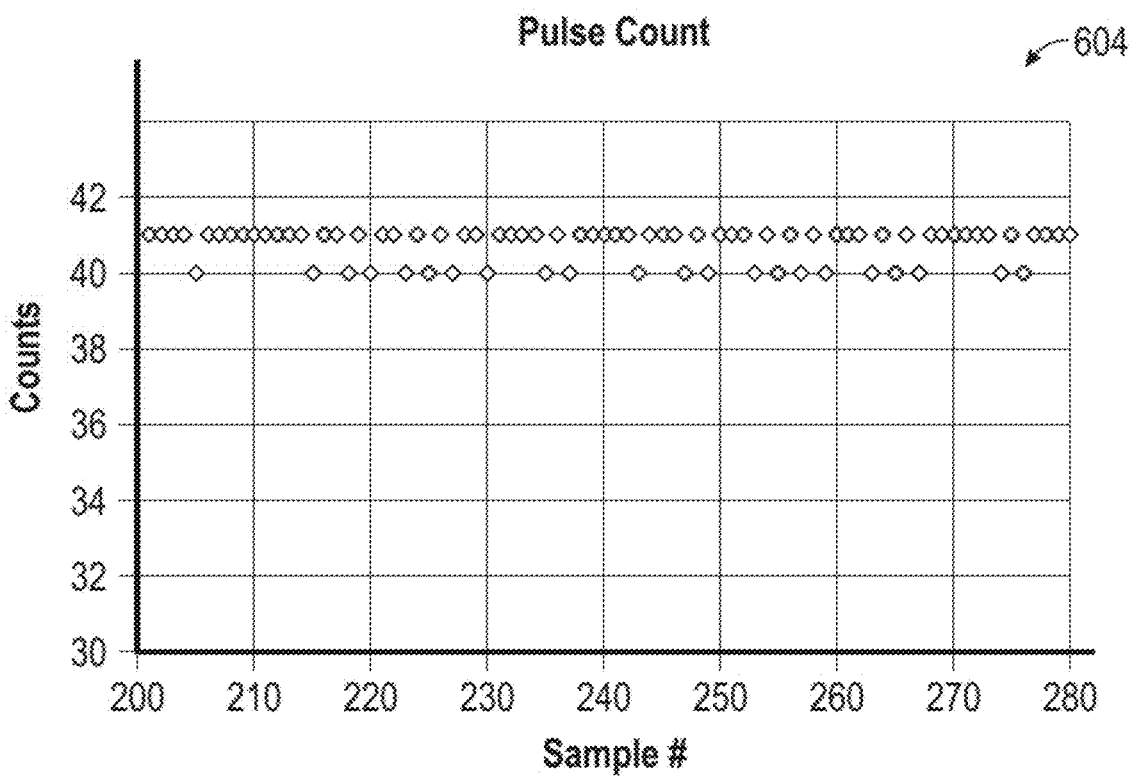
FIG. 6B is a graph that shows count values at the beginning of the Integration Time (Pre_Count) and at the end of the Integration Time (Pulse_Count) for the plurality of sensor samples of FIG. 6A.
Figure 6C:
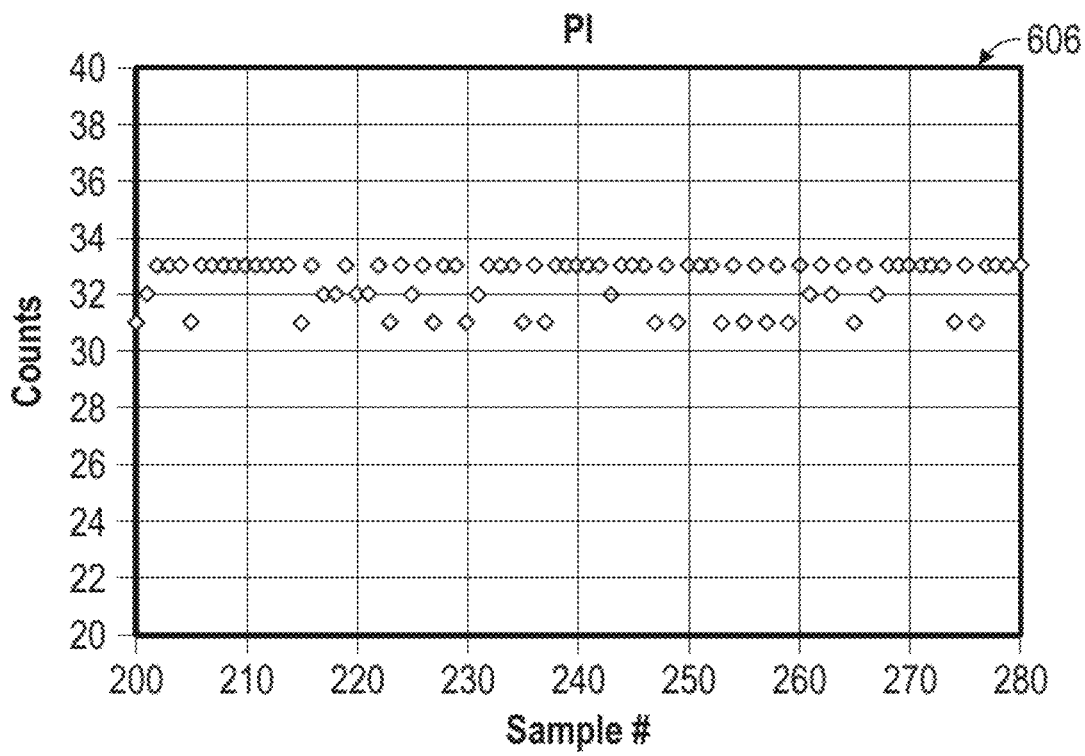
FIG. 6C is a graph that shows integrated charge count (PI) for the samples of FIGS. 6A and 6B.
Figure 6D:
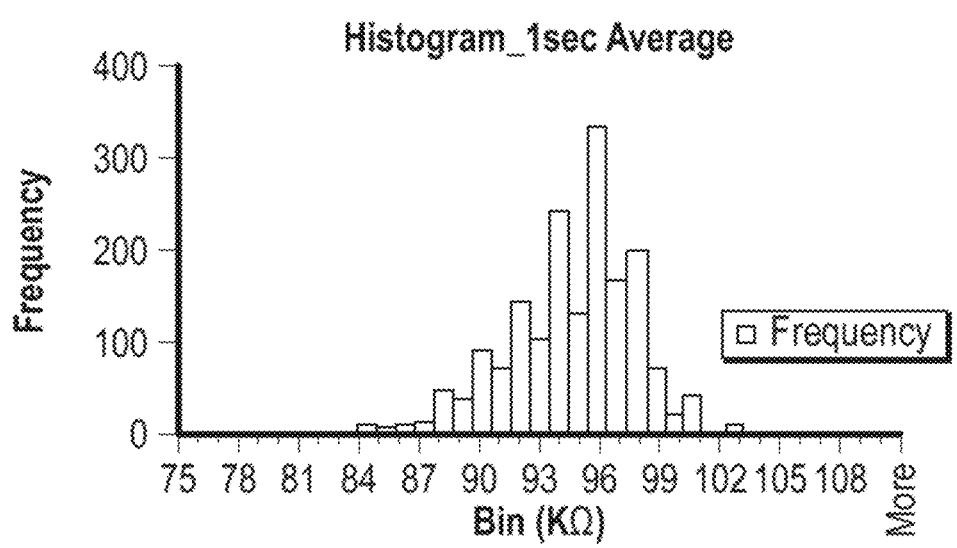
FIG. 6D is a histogram plot of determined impedance for a sensor, where charge count was averaged over a plurality of one-second sampling periods.
Figure 6E:
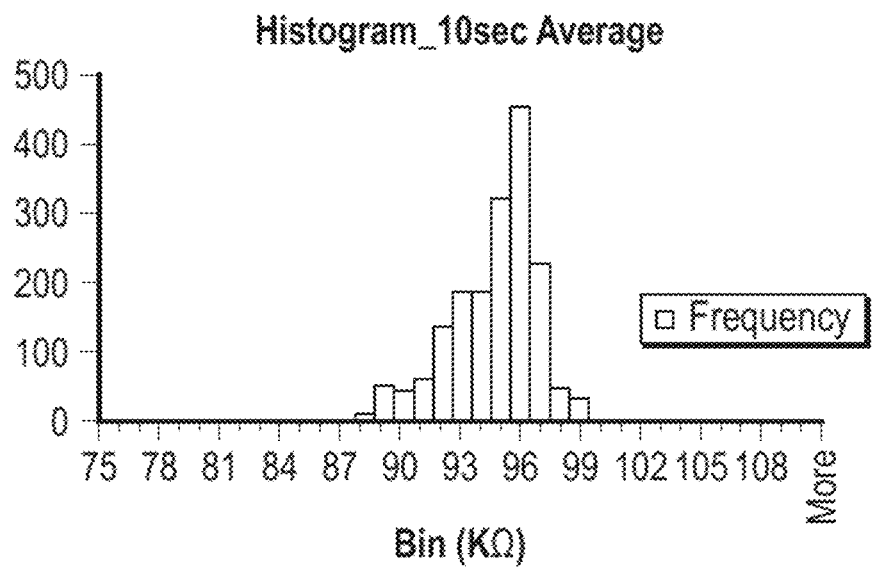
FIG. 6E is a histogram plot of determined impedance for a plurality of ten-second sampling periods.
Figure 6F:
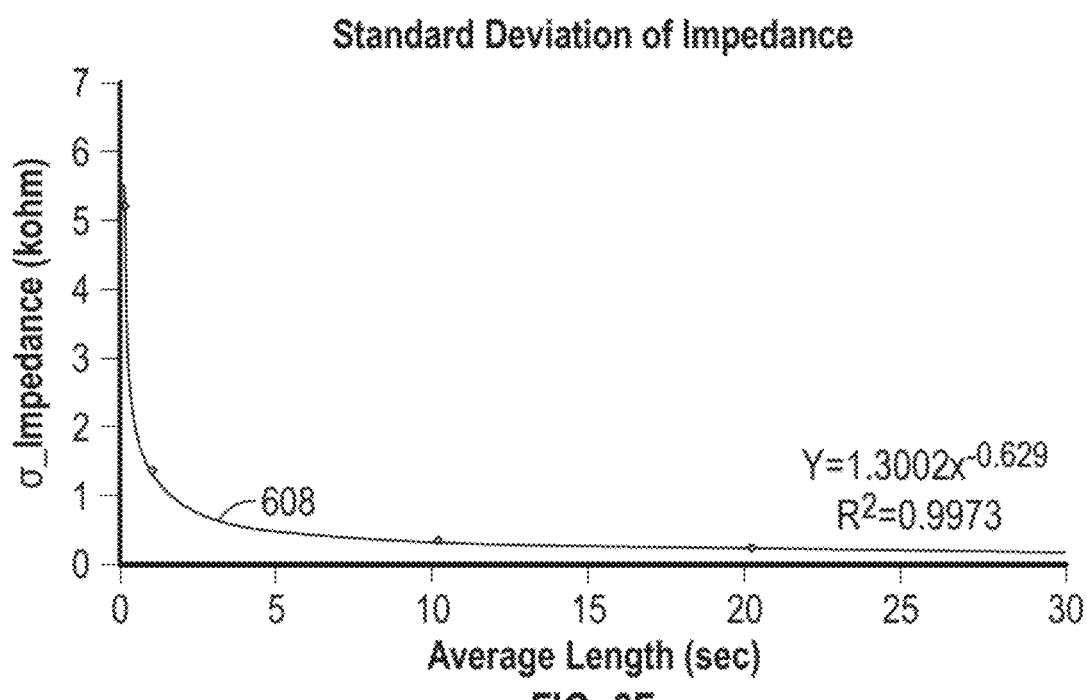
FIG. 6F is a graph that shows the standard deviation of determined impedance values for a sensor plotted against a length of time over which current (e.g., integrated charge count) was measured or determined.

FIGS. 6A and 6B show respective count values 602, 604 at the beginning of the Integration Time (Pre_Count) and at the end of the Integration Time (Pulse_Count) for a plurality of samples by a sensor. FIG. 6C shows the integrated charge count (PI) 606 for the Integration Time (Pulse_Count-Pre_Count.) The counts for multiple Integration Times in a sampling interval (e.g., 1 second, 10 seconds, 12 seconds, or 20 seconds) maybe be averaged to determine an average (e.g., mean or median) integrated charge count (PI), which may increase the accuracy of the charge count (PI) or increase the accuracy of an impedance or sensitivity derived therefrom. FIG. 6D shows a histogram plot of determined impedance for a sensor, where charge count was averaged over a plurality of one-second sampling periods (e.g., at a rate of one sample every 5 milliseconds during the sampling period). FIG. 6E is a histogram plot of determined impedance for a plurality of ten-second sampling periods. The histogram based on ten-second sampling periods provides a tighter distribution (e.g., more clustering around 96 k$\Omega$ and a tighter standard deviation). While using an average value from a plurality of Integration Times may improve the accuracy of the integrated charge count (PI) and impedance or sensitivity derived therefrom, obtaining a large data set may have an adverse impact on battery life due to energy consumed in applying the voltage step and processing the resulting current. FIG. 6F shows the standard deviation of determined impedance values 608 for a sensor plotted against a length of time over which current (e.g., integrated charge count) was measured or determined. In some examples, an averaging time of about 1 second (e.g., 0.5 to 1.5 seconds, or 0.5 to 3 seconds) is used, to provide a set of determined impedance values having a standard deviation of less than 2 Ohms. In some examples, an averaging time of about 10 seconds or 12 seconds (e.g., 5 to 15 seconds, or 8 to 12 seconds, or 10 to 14 seconds) is used to collect current (e.g., integrated charge count) values, which may provide a set of determined impedance values with a standard deviation of less than 1 Ohm.

The Relationship Between Impedance and Sensitivity.

Figure 7A:
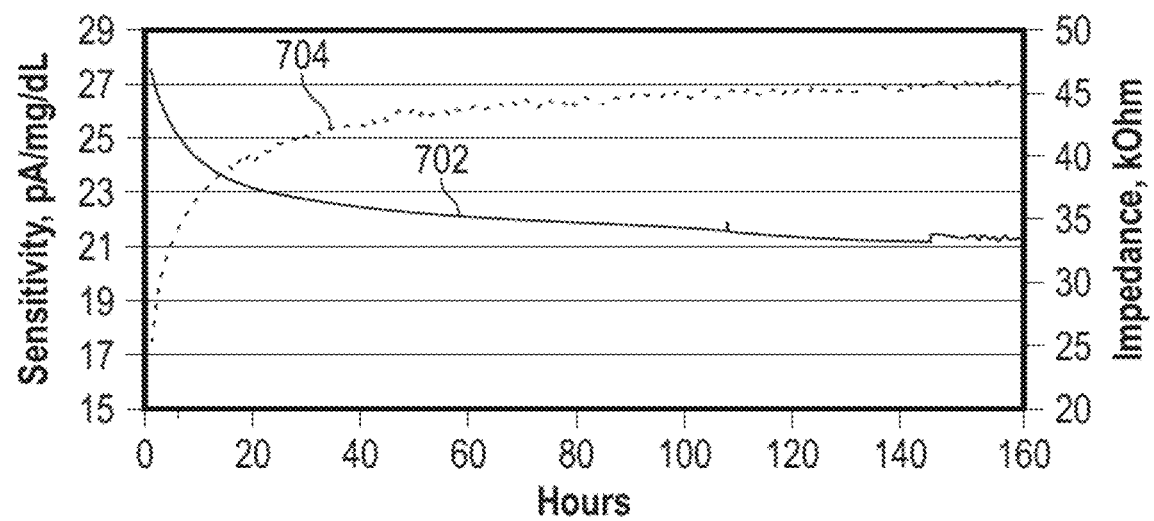
FIG. 7A is a graph that shows experimental data plotted against time, where impedance was measured from a tested sensor, and sensitivity was determined by placing the tested sensor in a solution having a known glucose concentration (e.g., a known mg/dL of glucose) and measuring a current.
Figure 7B:
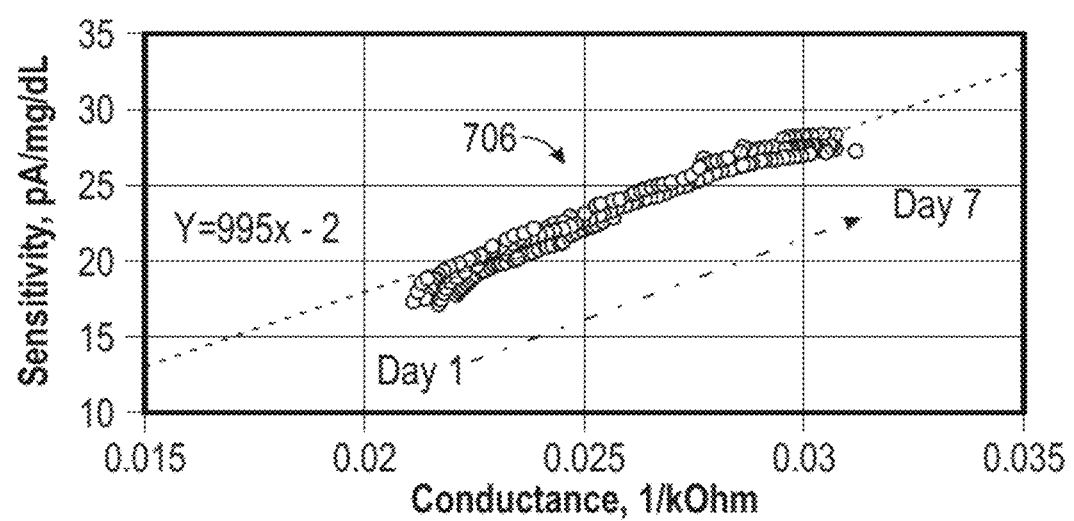
FIG. 7B is a graph that shows sensitivity plotted against conductance.

A correlation has been observed between the estimated impedance (e.g., resistance in a DC circuit) and the glucose sensitivity of a sensor. FIG. 7A shows experimental data plotted against time, where impedance 702 was measured from a tested sensor, and sensitivity 704 was determined by placing the tested sensor in a solution having a known glucose concentration (e.g., a known mg/dL of glucose) and measuring a current (e.g., in pA) in the tested sensor circuit (e.g., using sensor electronics). As can be seen from the graph, impedance 702 falls over time and glucose sensitivity 704 rises. FIG. 7B shows sensitivity 706 plotted against conductance (which is the inverse of impedance) for a number of sensors. A linear relationship between sensitivity and conductance (e.g., y=995x-2, or Sensitivity=995(Conductance)−2) may be observed from the data in FIG. 7B. The relationship between sensitivity and conductance may be used to determine a sensitivity in a sensor (e.g., an implanted sensor) having an unknown sensitivity and a conductance determined from a sensor measurement (e.g., the inverse of a measured impedance as described above). In some examples a functional range of the relationship may be defined. For example, a function range may be defined as in which the relationship between conductance and sensitivity is linear or approximately linear, such as 0.023 to 0.030 in FIG. 7B.

Assessment of Membrane Integrity

Measurements by sensor electronics may be used to assess the integrity of a sensor membrane. An analyte sensor may deviate from a performance standard (e.g., deviate from a default sensitivity curve) due to manufacturing variability, damage, or both. In some examples, such a performance variance may be detected or quantified using a determined impedance for a sensor. For simplicity of explanation, in the examples described in this present application a sensor may be referred to as "damaged" to indicate an abnormality in the sensor membrane composition, but references to a "damaged" sensor should be interpreted as also applying to a sensor that has an abnormality (e.g., an abnormality that is a result of a manufacturing process or damage inflicted by handling of the sensor).

An analyte sensor (such as a CGM sensor) typically includes one or more functional membranes, which may include abnormalities or suffer damage during sensor assembly, deployment, or other handling of the sensor. Membrane damage may, for example, include a scratch, puncture, or delamination. When a membrane is damaged, it may produce extra passages for an analyte (such as glucose for a CGM sensor) to reach an underlying electrode surface, which may inflate a sensor's output signal (e.g., increase the sensitivity to glucose), or produce a signal that is noisier or less consistent than normal.

It may be desirable to detect a sensor with a damaged or abnormal membrane, so the sensor can be rejected (e.g., during manufacturing), replaced (e.g., by an end user), or compensated (e.g., a compensation factor may be applied to address minor damage or abnormality). In varying examples, an impedance measurement based on electronic measurements may be used to detect a damage or abnormality early in a manufacturing process to avoid further processing of non-viable sensors, or late in a manufacturing process as a final check to assure that the sensor was not damaged during handling, or prior to or concurrent with insertion into a host, to avoid inconvenience for the user or potential reliance on an inaccurate sensor output.

Damage or an abnormality in a sensor may be identified or quantified using an estimated impedance, such as a membrane impedance as described above. One or more membranes on an analyte sensor are designed to restrict the mobility of molecules and ions. If a membrane is damaged by scratch, puncture, or delamination, ions can move relatively freely in those areas/sections compared to inside the membrane. Therefore, membrane damage may correspond to decrease of impedance (increase of admittance, or conductance).

Membrane damage or abnormalities may take a variety of forms. For example, one or more sensor coating layers may be thinner or different than a surrounding area on the membrane, or a coating layer may be damaged or missing, or, when a sensor coating is badly damaged, an electrode may be exposed.

Figure 8A:
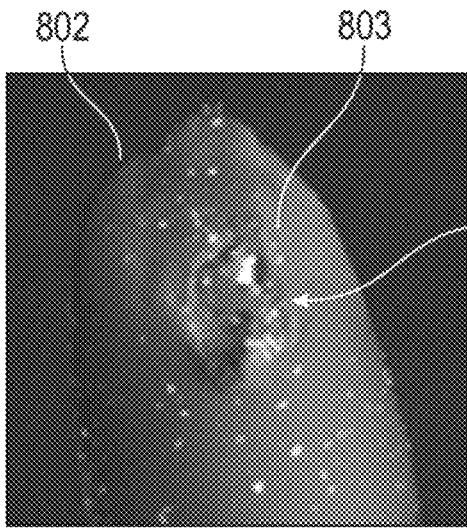
FIG. 8A is an image of an example sensor that has a damaged or abnormal portion.
Figure 8B:
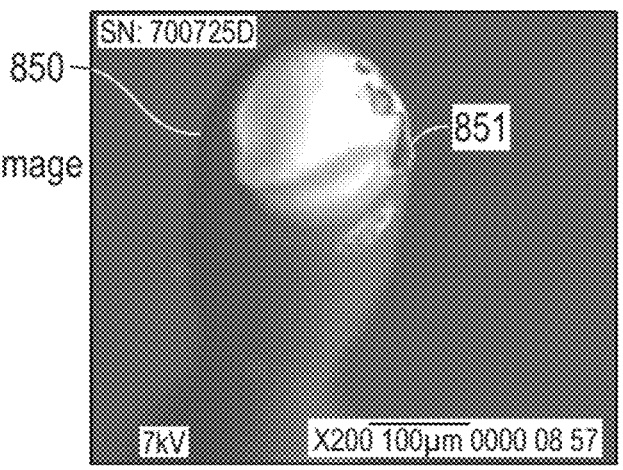
FIGS. 8B and 8C show other examples of damage or abnormality.
Figure 8C:
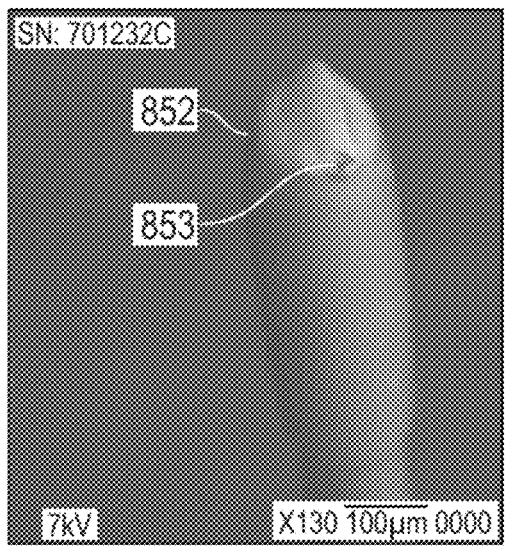

FIG. 8A is an image of an example sensor 802 that has a damaged or abnormal portion 803 on the membrane. The imperfection in the sensor membrane may affect the electrical behavior of the sensor 802 in response to changes in glucose concentration. For example, the sensor 802 may exhibit a higher sensitivity to glucose (compared to a sensor without the imperfection) due to increased glucose diffusivity through the sensor coating layers. FIGS. 8B and 8C show other examples of damage or abnormality 851, 853 from manufacturing of the sensors 850, 852.

The determination of whether a membrane is healthy or excessively damaged or abnormal is necessarily a matter of degree, as all sensor membranes will have some degree of variation in membrane thickness or composition. For example, damage to a sensor coating may range from a slight abnormality (e.g., a thin or missing layer in a small portion of the sensor) to severe damage that exposes the working electrode. A sensor with minor coating damage may function properly, but the sensitivity of the sensor may be slightly increased. In some examples, a sensor may have a relatively large area of damage, but the damage may be relatively shallow, so that the sensor performs acceptably well. In other examples, a sensor may have a relatively small area of damage, but the damage may be relatively deep, e.g., the damage may extend most or all of the way to the electrode, in which case the sensor performance may be excessively compromised even though the damage affects a relatively small portion of the surface area of the sensor.

Figure 8D:
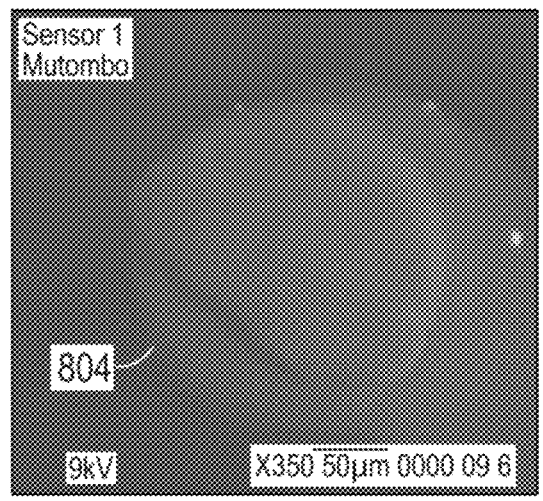
FIGS. 8D through 8H show sensors with damage ranging from none to heavy damage.
Figure 8E:
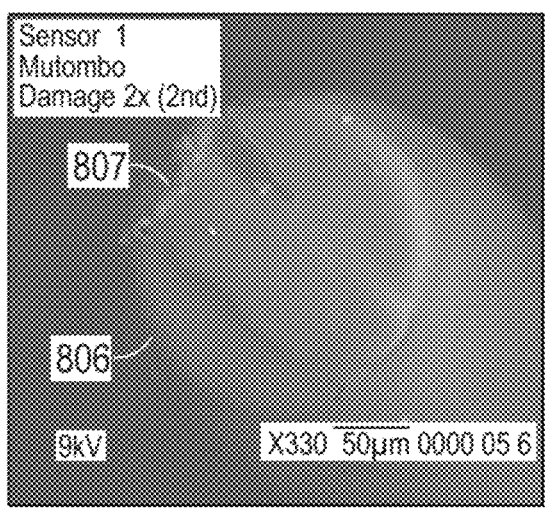
Figure 8F:
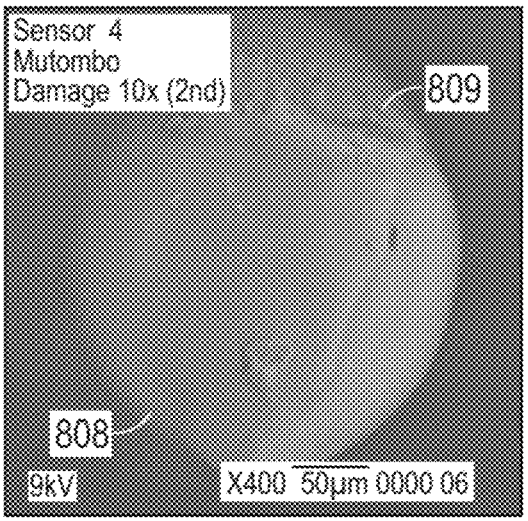
Figure 8G:
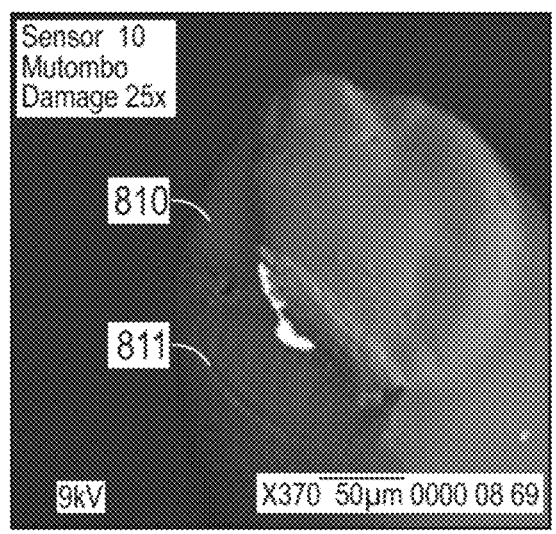
Figure 8H:
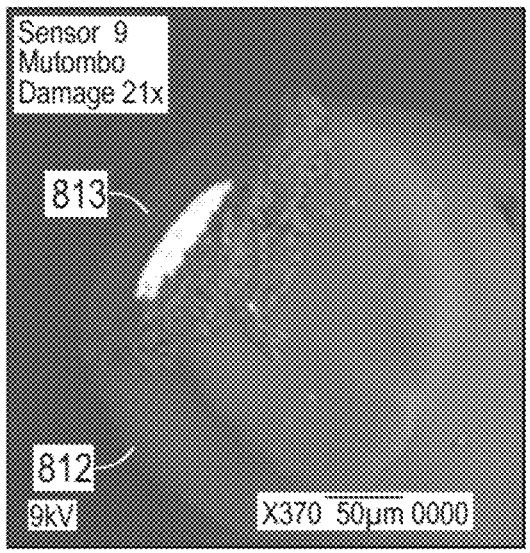

Sensors may be categorized according to a membrane damage scale to quantify the extent of damage. For example, a numerical scale may be developed, where 0 indicates no damage (i.e., a healthy sensor), 1 indicates very minor damage, 4 indicates a moderately damaged sensor, and 8 indicates a heavily damaged sensor (with numbers in between correlated to a continuous scale of damage). FIGS. 8D through 8H show sensors with damage ranging from none to heavy damage. The damage was created by rubbing the sensors on sandpaper to create a spectrum of damaged sensors (with minor to heavy damage) to enable testing of impedance and other characteristics. FIG. 8D shows a microscope image of a healthy sensor 804, with no damage. FIG. 8E shows a sensor 806 that has a portion 807 with minor damage. FIG. 8F shows a sensor 808 that has a portion 809 with moderate damage. FIG. 8G shows a sensor 810 with a portion 811 that has moderately severe damage. FIG. 8H shows a sensor 812 that has a portion 813 with severe damage.

Figure 9:
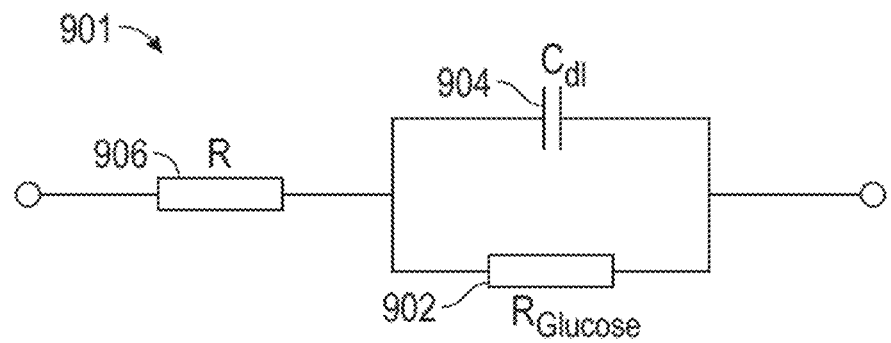
FIG. 9 is a schematic illustration of a simplified equivalent circuit of an analyte sensor.

The presence or extent of damage in a sensor may be evaluated using electrical measurement, such as a determination of impedance. FIG. 9 is a schematic illustration of a simplified equivalent circuit 901 of an analyte sensor. The circuit 400 shown in FIG. 4 (or other variants) may also be used for sensor analysis, but for simplicity reference will be made to the circuit 901 shown in FIG. 9. The resistor 902 represents the polarization resistance (RGlucose, labeled Rpol in FIG. 4) and capacitor 904 represents the double-layer capacitance (Cdl). The resistor (R) 906 represents the combined resistance of the membrane (Rmembr in FIG. 4), the electrodes, and the internal resistance in sensor electronics (R_Tx_internal in FIG. 4). Using Ohm's law (I=V/R), impedance of the resistor (R) may be measured, which can indicate the presence or extent of membrane damage or abnormality.

A sensor with excessive damage or abnormality (as determined using impedance, for example), may be identified and excluded from use in a host. For example, an excessively damaged sensor may be identified after implantation in a host, in which case an alert may be delivered to a user to notify the user of the damage (e.g., "Damaged sensor detected. Please replace sensor."). In some examples, a sensor system may apply compensation to account for the minor damage to the sensor. For example, a sensitivity for the sensor may be adjusted (e.g., based on a determined impedance) to provide an accurate estimated analyte concentration level despite the abnormality or damage in a sensor coating.

Figure 10:
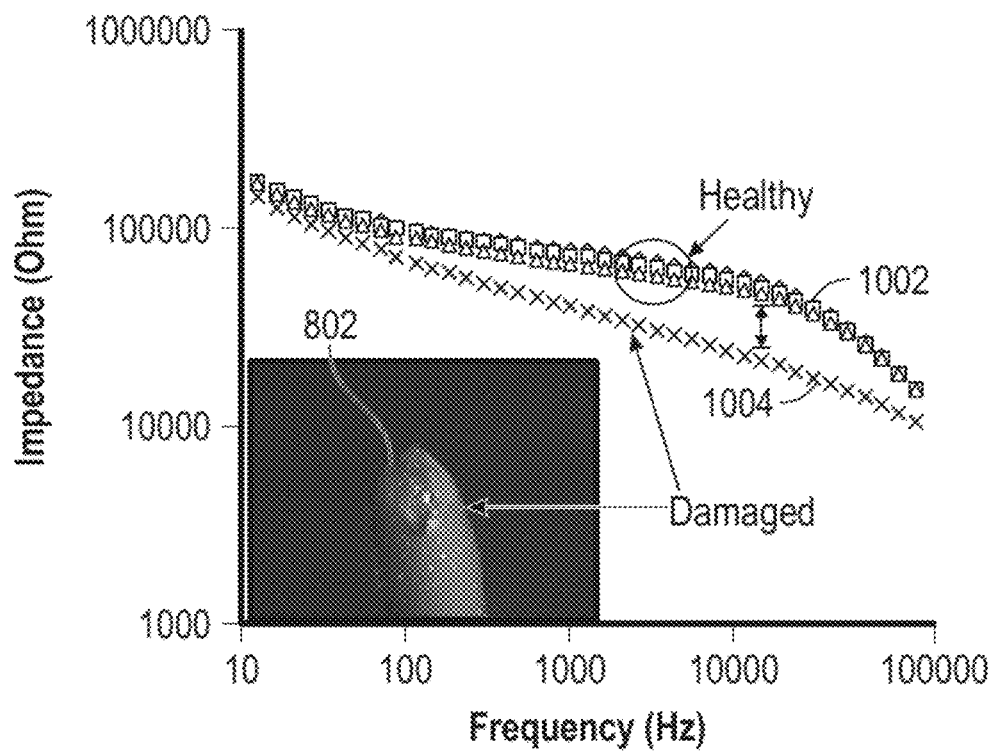
FIG. 10 is a graph that shows impedance plotted against frequency (Hz) for a damaged or abnormal sensor and healthy (non-damaged) sensors.

In some examples, a sensor with damage or an abnormality in the sensor membrane may be more easily differentiated from a healthy sensor by comparing the impedance at a frequency that accentuates the difference in impedance. FIG. 10 is a plot of impedance (Ohms) vs. frequency (Hz) for a damaged or abnormal sensor (such as sensor 802) and healthy (non-damaged) sensors. Both the X and Y axes are logarithmic scales. It can be seen from the plot that the difference between impedance of a damaged sensor 1004 and the impedance of healthy sensors 1002 varies with frequency. For example, at 100 Hz and 100 kHz the impedance of a damaged sensor 1004 is relatively close to the impedance of healthy sensors 1002. In comparison, at 10 kHz the difference in impedance between a damaged sensor 1004 and healthy sensors 1002 is relatively large, as indicated by the arrow in FIG. 10.

In an example, a sensor with damage or an abnormality may be identified by measuring impedance at a frequency (e.g., 5,000 Hz or 10,000 Hz, or somewhere in the range of 1000 to 30000 Hz) where there is a relatively large gap between impedance of a damaged sensor and that of a healthy sensor.

In another example, a plurality of impedance measurements may be taken over a range of frequencies, and a damaged or abnormal sensor may be differentiated from a healthy sensor using impedance spectroscopy. For example, a damaged sensor may be differentiated from a healthy sensor, or an extent of damage (or abnormality) may be determined or estimated based on attributes of the impedance-frequency curve, such as shape, impedance value, derivative (slope), or second derivative (curvature). In some examples, the impedance or estimated damage/abnormality level may be used to compensate for the slight damage or abnormality.

Figure 11A:
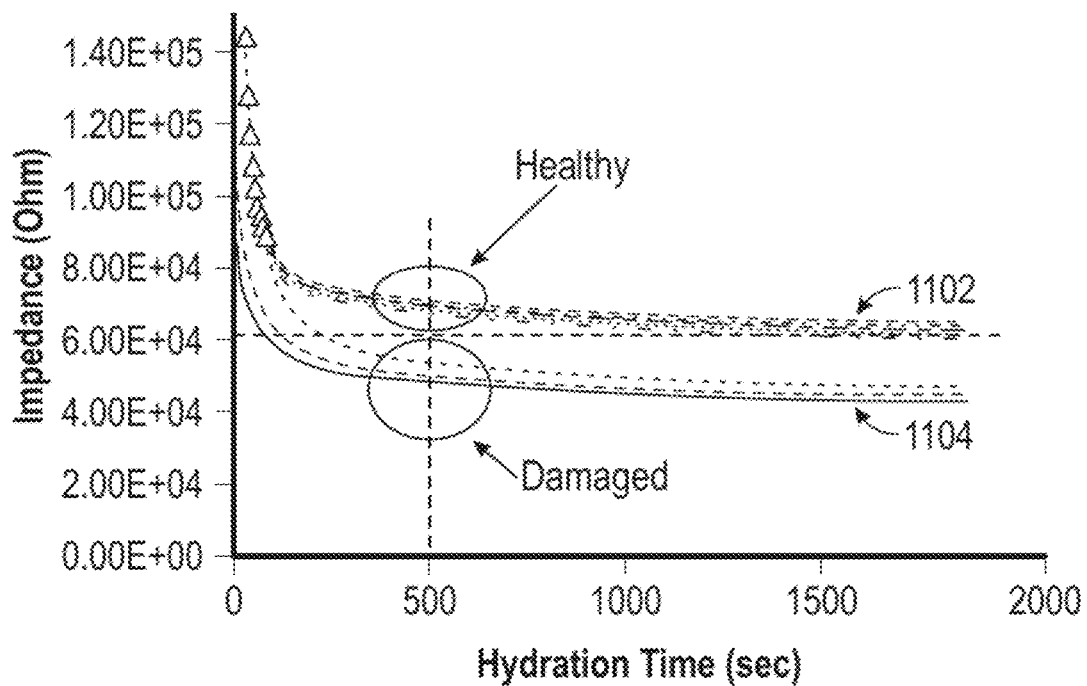
FIG. 11A is a plot of impedance vs. hydration time for a number of sensors.

FIG. 11A is a plot of impedance vs. hydration time for a number of sensors, at 5000 Hz. After sufficient hydration time (e.g., 400 seconds), the damaged sensors produce an impedance 1104 that is significantly smaller than the impedance 1102 of healthy sensors. This impedance difference for healthy vs. damaged sensors may be used to identify damaged or abnormal sensors. For example, a sensor that has an impedance lower than 60000 Ohm after 400 seconds may be deemed abnormal or damaged, or may require compensation, depending on the amount of damage or abnormality, which may be inferred from the impedance. For example, a first threshold may identify sensors that require compensation, and a second threshold may identify sensors that are deemed excessively damaged and excluded from a population of usable sensors. FIG. 11A illustrates an example in which a threshold has been set at 60 kiloohms at 500 seconds of hydration time, which clearly differentiates excessively damaged sensors from healthy sensors.

Figure 11B:
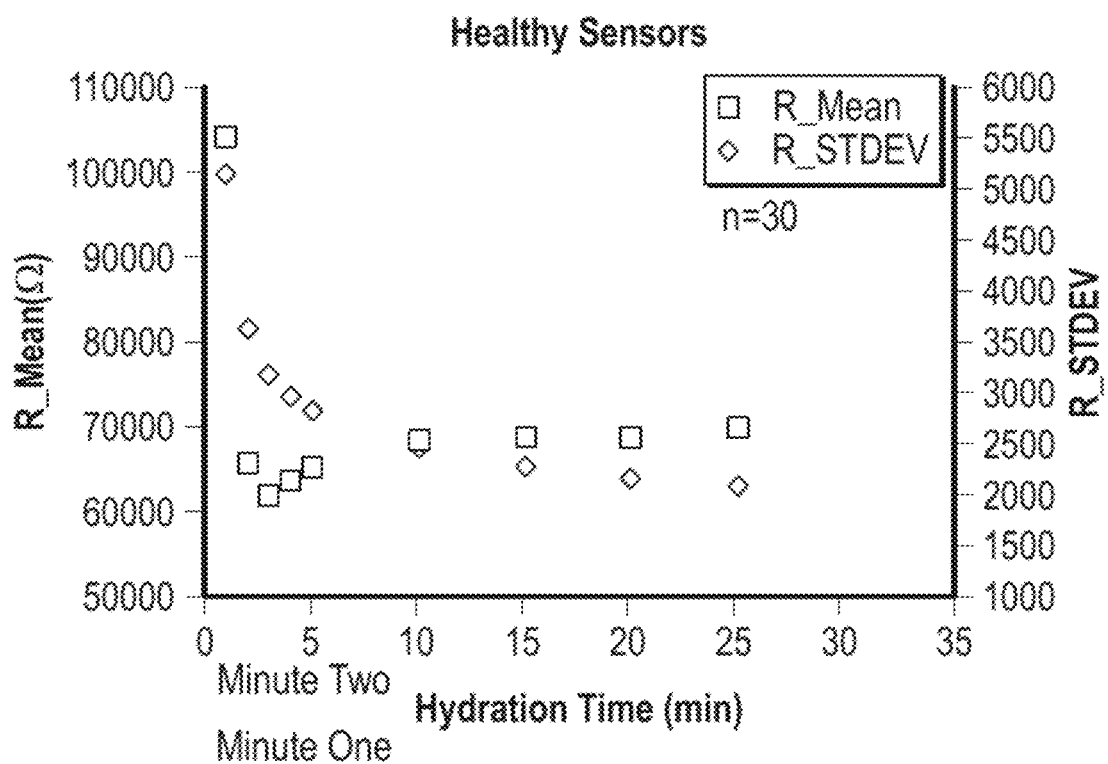
FIG. 11B is a plot of the mean impedance and standard deviation of impedance against hydration time.

FIG. 11B is a plot of the mean impedance (R_mean, indicated by a diamond) and standard deviation (R_STDEV, indicated by a square) of impedance (R_mean) for a number of hydration times. It can be seen from the plot that the standard deviation drops significantly from minute one (R_STDEV over 5000) to minute two (R_STDEV under 2500) and stays below 3000 through minute 30. A damage determination may be made based on an impedance value that is measured after the standard deviation has dropped, e.g., to more effectively assure that a particular sensor is healthy, as opposed to damaged or abnormal.

Figure 12A:
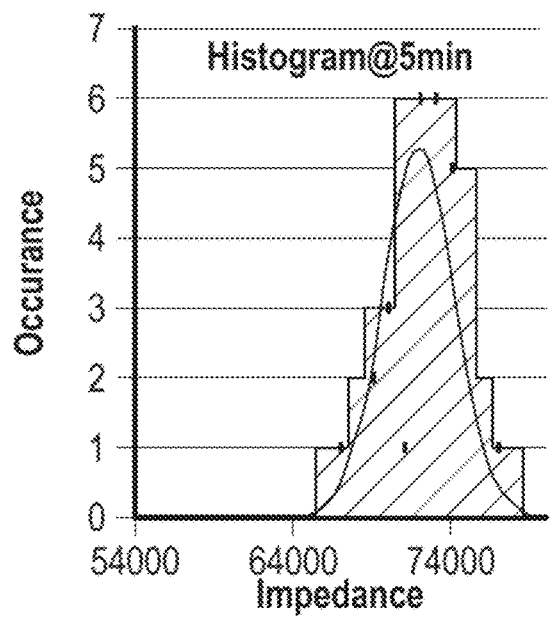
FIGS. 12A-C are graphs that show impedance distributions of sensors at 5 minutes, 10 minutes, and 30 minutes of hydration, respectively.
Figure 12B:
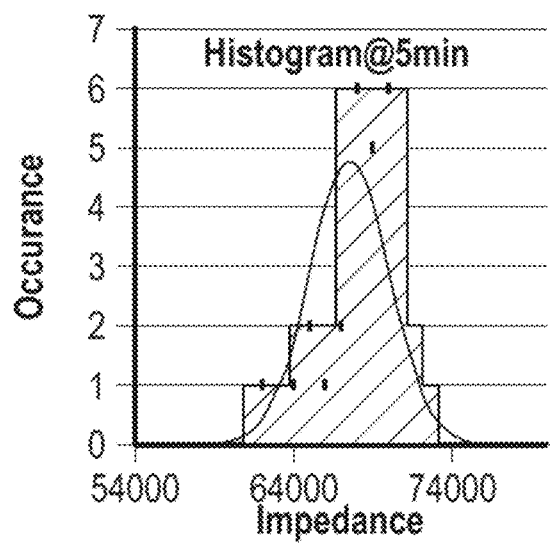
Figure 12C:
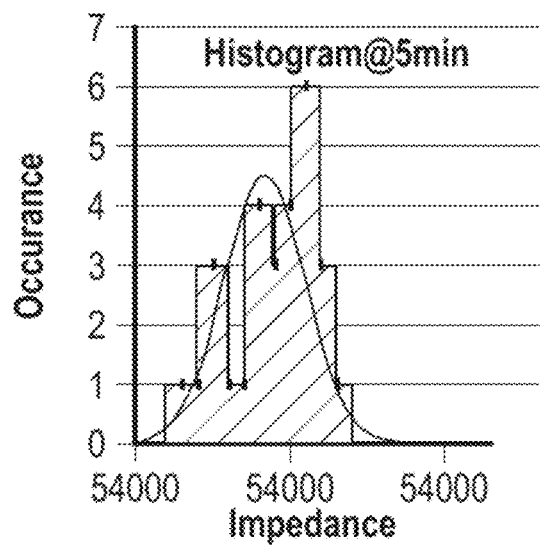

FIGS. 12A-C are histogram plots of determined sensor impedance for healthy sensors at 25 kHz. FIG. 12A shows the impedance distribution at 5 minutes, FIG. 12B shows the impedance distribution at 10 minutes, and FIG. 12C shows the impedance distribution at 30 minutes. The standard deviation of impedance at five minutes is 2.3 kiloohms. The standard deviation of impedance at thirty minutes is 2.7 kiloohms. It may be desirable to measure impedance early (e.g., five minutes of hydration time, or less), as waiting until the 30 minute point does not improve the standard deviation of the impedance distribution. In some examples, an impedance accuracy of one kiloohm is sufficient to identify healthy sensors (e.g., an impedance that deviates from a defined value (e.g., the mean, or a specified value that approximates the mean) may be taken as an indication that a sensor has damage or an abnormality).

Figure 13A:
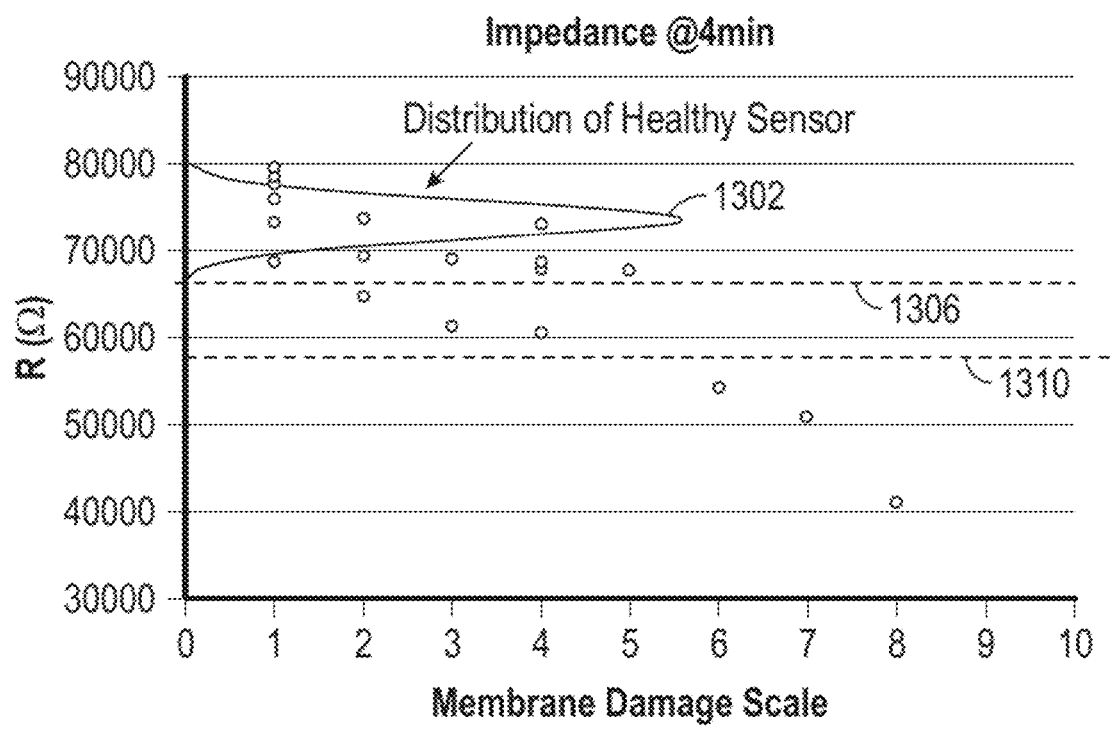
FIGS. 13A and 13B are graphs that shows impedance plotted against the membrane damage scale used to classify the damage on the sensor membranes shown in FIGS. 8B through 8H. The impedance values in FIG. 13A are based on measurements 4 minutes after hydration and the impedance values in 13B are based on measurements 10 minutes after hydration.
Figure 13B:
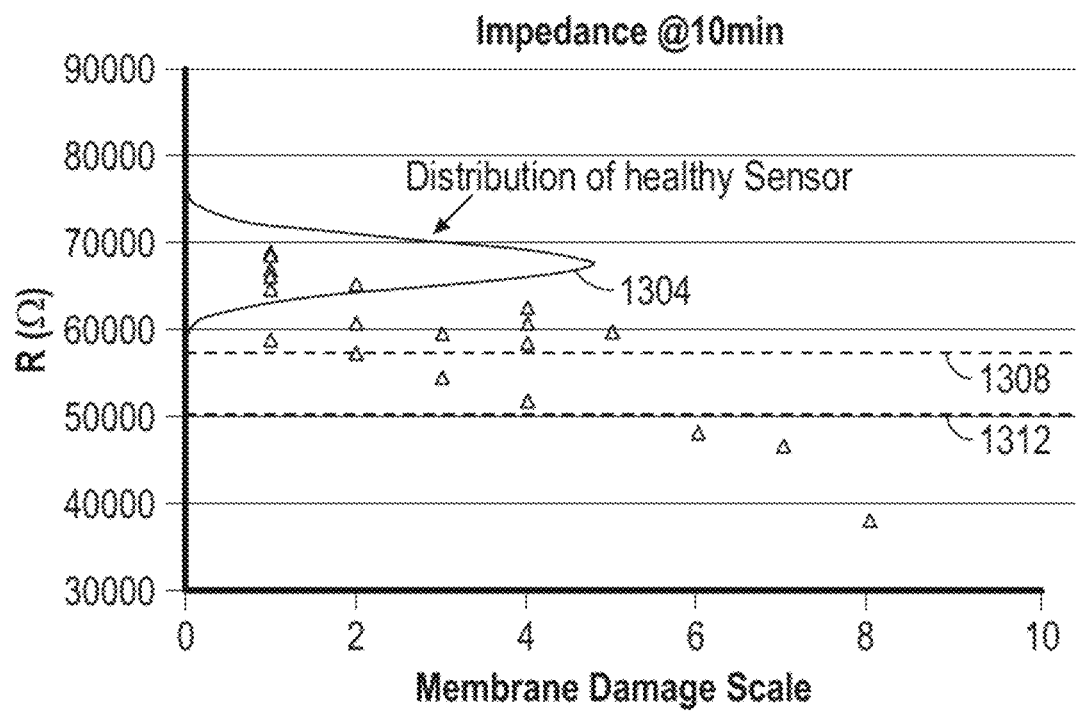

FIGS. 13A and 13B show impedance plotted against the membrane damage scale used to classify the damage on the sensor membranes shown in FIGS. 8B through 8H. For FIG. 13A, the impedance measurements were taken at four minutes of hydration time, and for FIG. 13B, the impedance measurements were taken at 10 minutes of hydration time. The impedance measurements were taken at 25 kHz. The distributions of healthy sensors 1302, 1304 from FIGS. 13A and 13B have also been overlaid onto the figures (with the X-axis indicating frequency of occurrence for the healthy sensor distribution). Sensors with damage of greater than five on the damage scale may be identified based upon the lower impedance values associated with those heavily-damaged sensors (e.g., data points with a damage rating 6, 7, and 8 are far below the impedance of the healthy sensors). Sensors with slight to moderate damage had a measured impedance that overlapped with healthy sensors, but the impedance generally tended to be lower than the impedance range for healthy sensors. In some examples, an impedance threshold may be used to differentiate healthy sensors from excessively damaged sensors. For example, a threshold 1306 of 67 kiloohms may be used to identify damaged sensors (that have an impedance below 67 kHz) at four minutes as shown in FIG. 13A, or a threshold 1308 of 58 kiloohms may be used to identify damaged sensors at ten minutes, as shown in FIG. 13B. In another example, a threshold 1310 (e.g., 58 kiloohms in FIG. 13A) or 1312 (e.g., 50 kiloohms in FIG. 13B) may be used to identify heavily-damaged sensors (e.g., sensors that have a rating of greater than five on the damage scale referenced above). In some examples, a first threshold 1306 or 1308 may be used to identify sensors that should be compensated, and a second threshold 1310 or 1312 may be used to identify a sensor in which the damage or abnormality is large enough that the sensor should not be used.

It may be desirable to quickly identify a sensor that has excessive damage or abnormality. For example, after a sensor is implanted in a host, it may be desirable to make a sensor damage assessment within a minute or within a few minutes, so that a damaged sensor may be replaced. A rapid sensor damage assessment may be more convenient for the wearer of the sensor. For example, making a quick assessment increases the likelihood that the wearer is still in a location or situation where a sensor can be replaced if needed. A long assessment delay may increase the likelihood that the wearer has departed for work, gone to school, left the company of a caregiver, or otherwise experienced an environmental change that makes it more difficult to access a sensor or replace a sensor. It thus may be desirable to base a sensor damage or abnormality assessment upon an impedance determination that provides sufficient spread between healthy and excessively damaged sensors to enable differentiation and is also made reasonably early after sensor hydration (e.g., implantation in subcutaneous fluid). For example, with reference to FIG. 11A-B, impedance values at or before 500 seconds, 400 seconds, or 300 seconds (five minutes) may be used to differentiate excessively damaged or abnormal sensors from healthy sensors. The data shown in FIGS. 12A-C also suggests that a hydration time of about four or five minutes is sufficient to differentiate sensors based on impedance.

Figure 14A:
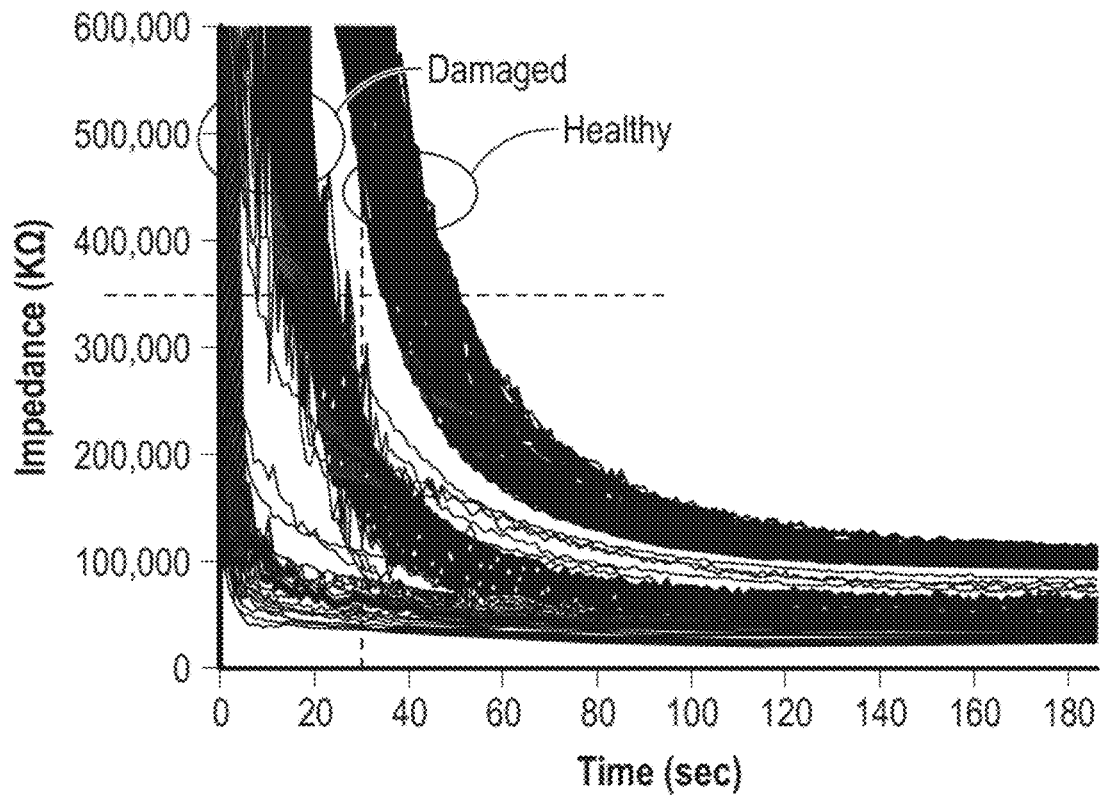
FIG. 14A is a graph that shows impedance plotted against time for a number of sensors.

It may be desirable to differentiate damaged or abnormal from healthy sensors even more quickly. FIG. 14A shows impedance plotted against time for 180 seconds (1.5 minutes) for a number of sensors. Due to membrane hydration, impedance drops quickly during the first minute, and then continues to drift down at a slower rate. The impedance for damaged sensors drops more quickly than the impedance for healthy sensors.

In some examples, in situations where the hydration time is known with sufficient precision (e.g., in systems that control sensor insertion or have a way to capture a time stamp when insertion occurs), a threshold time may be defined for a sensor to reach a particular impedance level. For example, a sensor may be deemed healthy if the impedance is above a threshold (e.g., 350 kiloohms) at a specified time (e.g., 30 seconds) after insertion. In another example, a plurality of impedance determinations may be made (e.g., one per second), and a sensor may be deemed to be healthy if none of the sensor readings falls below a threshold (e.g., none falls below 350 kiloohms in the first 30 seconds after implantation).

Figure 14B:
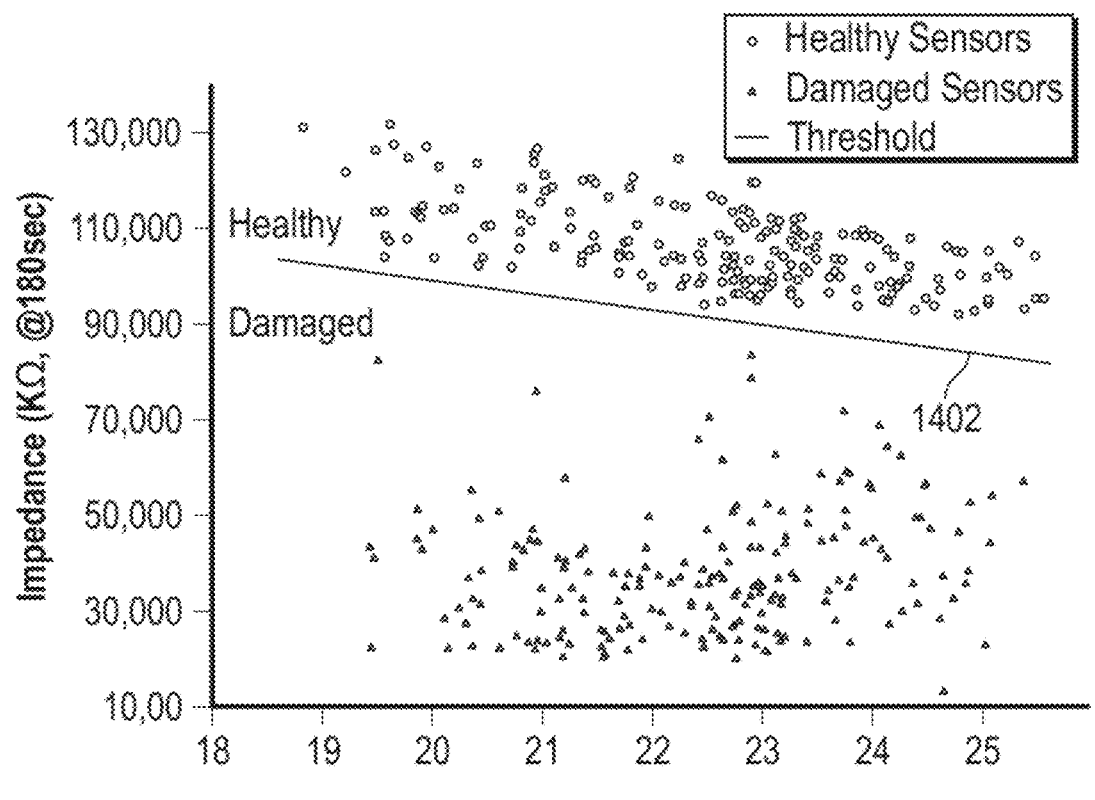
FIG. 14B is a graph of impedance plotted against sensor sensitivity to glucose concentration.

FIG. 14B is a graph of impedance plotted against sensor sensitivity to glucose concentration (in picoamps per milligram per deciliter), which may be determined for example during a factory calibration step or may be predefined or may be based on user calibration. In an example, a threshold 1402 may vary based upon the sensitivity of the sensor. For example, the threshold may be defined to have a linear relationship with sensitivity, as shown in FIG. 14B. In other examples, a threshold may be defined to have a different (e.g., polynomial) relationship with sensitivity, or a single threshold (e.g., 90,000 kiloohms for the data shown in FIG. 14B) may be used for all sensor sensitivities.

Figure 15A:
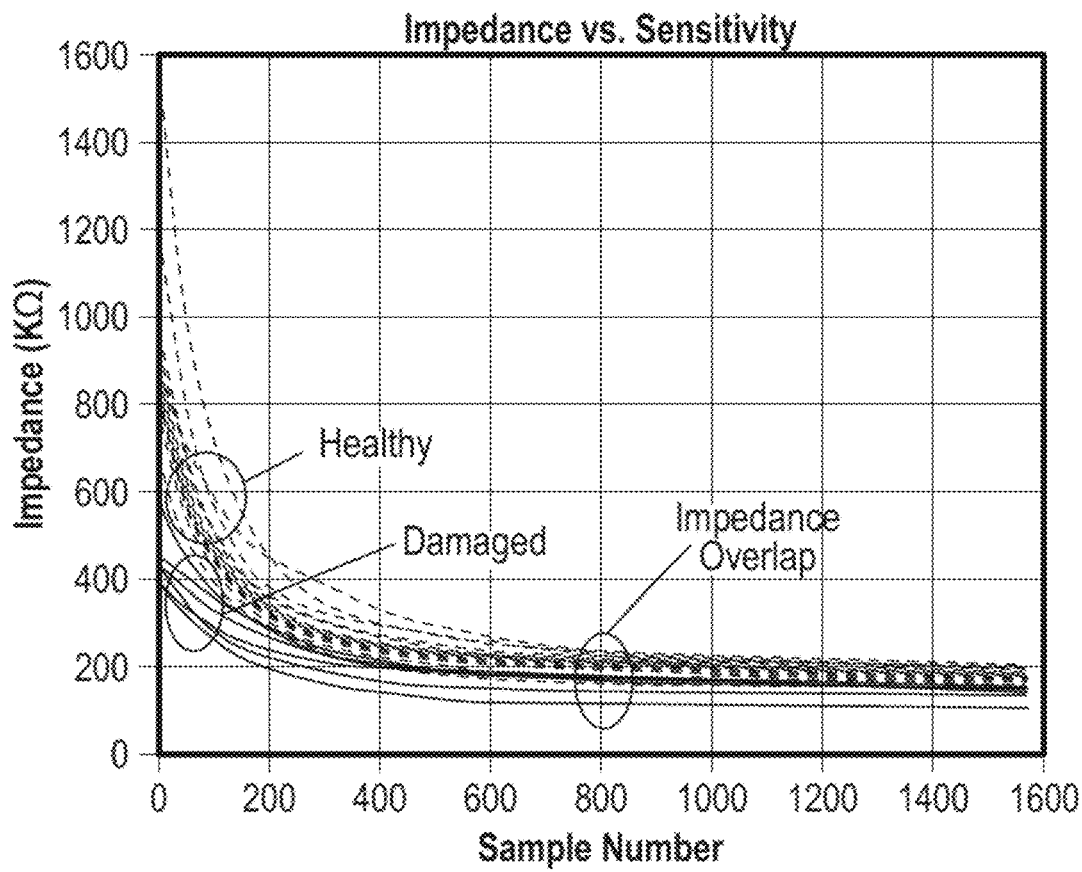
FIG. 15A is a graph that shows impedance plotted against sample number.

In some situations, the actual insertion time for a sensor may not be known. FIG. 15A is a plot of impedance against sample number. The samples are taken sequentially, but the time since insertion is not known, so zero point on the sample axis (X-axis) does not necessarily correspond to time zero. When a sensor is implanted into a wearer, there is typically a delay between sensor insertion into interstitial fluid and assembly of sensor electronics onto the sensor, at which point impedance determination and time measurement may begin. Because the delay is unknown, it may be difficult to differentiate a healthy sensor from an excessively damaged or abnormal sensor based solely on impedance values, because the values may overlap. Moreover, the full impedance trend shown in FIG. 15A may not be available: only a portion of the impedance trend may be captured, based upon timing of connection of the sensor electronics, or other factors.

Figure 15B:
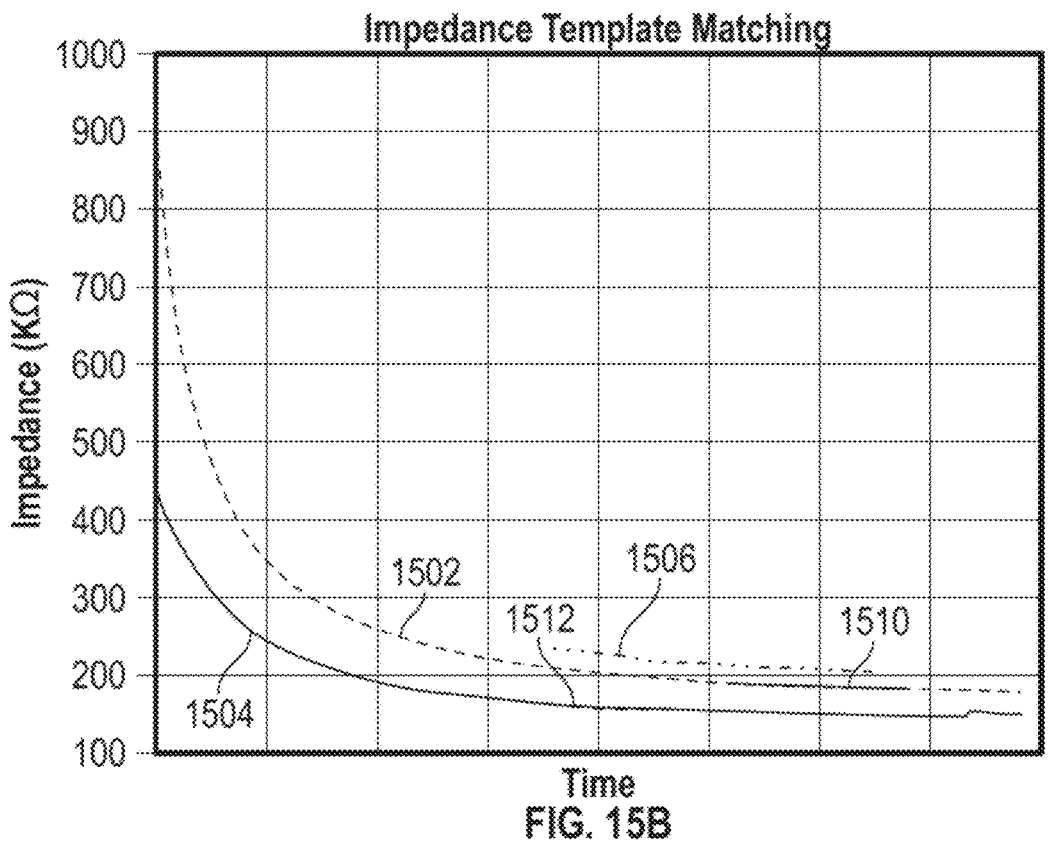
FIG. 15B shows a healthy sensor template, a damaged sensor template, and an impedance sample for a sensor-of-interest.

In some examples, to address these problems, impedance data for a sensor may be compared to one or more templates. For example, impedance may be compared to a healthy sensor template, or a damaged sensor template, or both. FIG. 15B shows a healthy sensor template 1502, a damaged sensor template 1504, and an impedance sample 1506 that is based on measurements of a sensor-of-interest. The impedance sample 1506 may be compared to a template to determine a template sequence (i.e., segment) that is most similar to the impedance sample (e.g., determine which part of the template curve best fits the impedance sample). In some examples, a template sequence match is identified for each template, and a determination is made as to which template sequence is more similar to the impedance sample. For examples, with reference to FIG. 15B, the impedance sample 1506 may be matched to sequence 1510 on healthy sensor template 1502 and matched to sequence 1512 on damaged sensor template 1504. If the impedance sequence is more similar to the sequence 1510 on the healthy sensor template 1502 than to the sequence on damaged sensor template 1504, the sensor corresponding to the impedance sample 1506 may be declared a healthy sensor.

In some examples, multiple reference templates may be used. For example, a plurality of reference templates may be used, where each reference template corresponds to a different damage level.

Dynamic Time Warping

A dynamic time warping (DTW) may be applied to address variations in the timing of impedance data. For example, an impedance sample may match the general shape or pattern of a template, but the time axis may be distorted, e.g., an impedance sample may show characteristics of a template that suggest a healthy (or damaged) sensor, but the rate of change of impedance may be different from the template. This issue may be addressed using a dynamic time warping technique. In some examples, a dynamic time warping (DTW) technique may be used to determine which template is most similar to an impedance sequence. Dynamic time warping may be particularly useful when the impedance sequence is discontinuous.

In an example, dynamic time warping may be applied to find similarities between a real-time measured sequence of impedance values and a reference template. For example, a DTW process may locally translate, compress, and expand the patterns so that similar features in the patterns are matched. In some examples, application of DTW may nonlinearly warp two trajectories in such a way that similar events are aligned and a minimum distance between them is obtained. Scaling may be performed prior to implementation of DTW to improve performance of DTW.

In an example, xa and xt may be the reference and test signal trajectories with data lengths and respectively. DTW may be applied to find a sequence F* of L points on an impedance vs. time (R×T) grid, e.g.:

$$F=[f(1), f(2), \ldots f(k), \ldots f(L)]$$

$$\text{Max}(ii, T) < L < R+T$$

where f(k)=[i(k), j(k)] is an ordered pair indicating a position on the grid, k is the number of the grid points along a path between two trajectories, i and j are the sample points (which go up to R and T for the reference and test trajectories, respectively). The sequence F* (among all possible F sequences) is a path on the grid that optimally matches each vector in both trajectories so that a normalized distance between them is minimized. DTW defines the Euclidean distance d between each point of the two trajectories as:

$$d(i(k), j(k)) = [x_r(i(K)) - x_T(J(k))]^2$$

The total distance between two trajectories is defined as $$D(R, T) = \sum_{\kappa=1}^{L} d(i(\kappa), j(\kappa))$$

The optimal path and minimum total distance is found as the solution of the following optimization problem:

$$F^* = \min_{F} D(R, T)$$

An elegant and effective solution to this problem is dynamic programming, which guarantees to find the optimum path without having to calculate the distance along all possible paths:

$$D_F(i, j) = d(i, j) + \min \begin{cases} D_F(i-1, j) \\ D_F(i-1, j-1) \\ D_F(i, j-1) \end{cases}$$

With respect to some local and global constraints $$D_F(b^*, T) = \min_{b \in [1:R]} D(b, T)$$

$$D_F(a^*, 1) = \max_{a \in [1:R]} a$$

$$i(\kappa + 1) \geq i(\kappa)$$

$$j(\kappa + 1) \geq j(\kappa)$$

In an experiment (using the data shown in FIG. 15A), the DTW method demonstrated good sensitivity and specificity. A population of sensors included nineteen healthy sensors and seven damaged sensors. The method identified 16 of the nineteen healthy sensors as healthy, and three of nineteen healthy sensors were identified as having damage. Six of seven damaged sensors were identified as damaged, and one of seven damaged sensors was identified as healthy. Application of DTW may improve the performance of a sensor system at differentiating between damaged and healthy sensors.

In some examples, derivative dynamic time warping may be used. A smooth derivative may be obtained, for example, using a Savitzky-Golay Filter.

Continuous Impedance Measurements

In another example, if continuous impedance measurements are available, matching may be accomplished using the equations:

$$V_d(k) = \sum_{i=k}^{k+N_{test}-1} (x_{test}(i - k + 1) - x_{damaged}(i))^2$$

$$k = 1, \ldots, N_{damaged} - N_{test}$$

$$V_h(k) = \sum_{i=k}^{k+N_{test}-1} (x_{test}(i - k + 1) - x_{healthy}(i))^2$$

$$k = 1, \ldots, N_{healthy} - N_{test}$$

$$\text{outcome} = \min(\min(V_d(k)) \min(V_h(k)))$$

where Ntest, Ndamaged, and Nhealthy are the size of real-time measured impedance sequence, reference damaged template, and reference healthy template, respectively.

Impedance—Frequency Characteristics

In some examples, the impedance of a sensor at a specified frequency, or at two or more frequencies, may be used to ascertain information about the sensor. For example, the difference between impedance at two different frequencies, or the shape (e.g., slope) of an impedance-frequency curve, may be used to determine information about a sensor, such as a damage state. Measuring impedance or sensor damage at higher frequencies (e.g., 1 kilohertz or above) may improve the accuracy of measurements, because the double membrane capacitance has less of an effect on the circuit behavior at higher frequencies (e.g., the sensor circuit acts like a high-pass filter).

Figure 16:
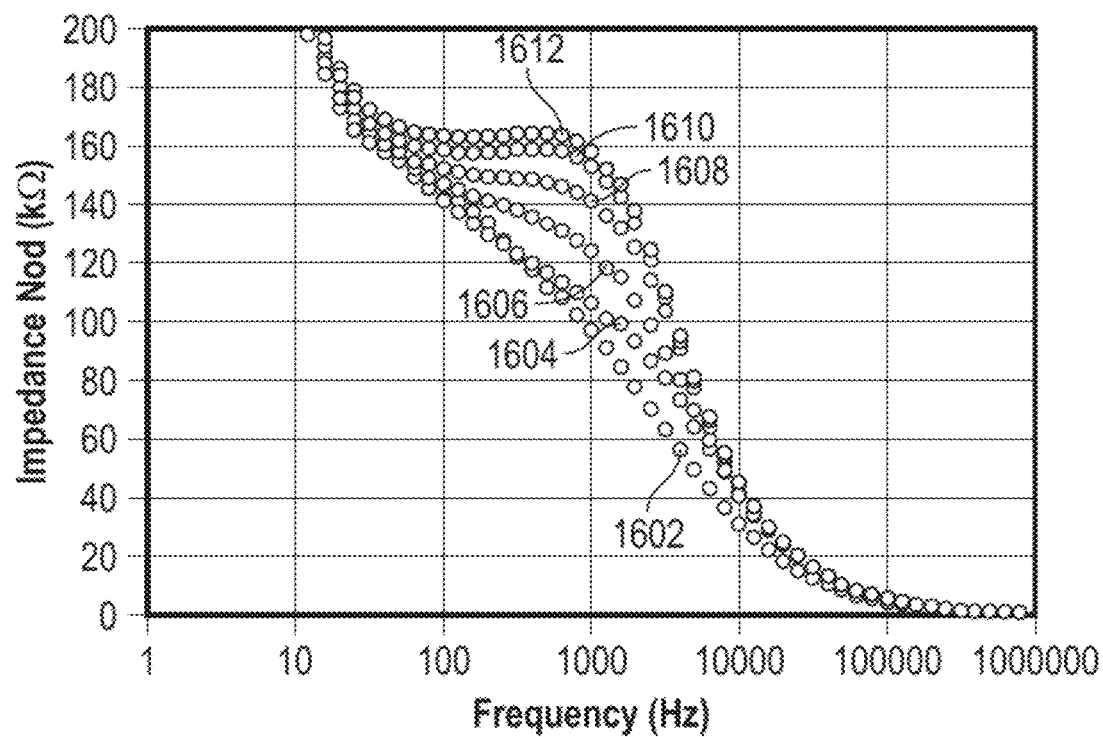
FIG. 16 is a graph that shows impedance plotted against frequency for six sensors.

FIG. 16 is an illustration of impedance plotted against frequency for six sensors. For each sensor, a plurality of impedance measurements were taken across a range of frequencies. To obtain a spectrum of damage levels, the sensors were subject to different levels of physical damage by scratching the sensor against sandpaper. The scratching involved dragging a sensor a distance across sand paper a number of times. The same grade of sandpaper was used for scratching each sensor. A first curve 1602 corresponds to a sensor that was scratched 20 times. A second curve 1604 corresponds to a sensor that was scratched 10 times. A third curve 1606 corresponds to a sensor that was scratched five times. A fourth curve 1608 corresponds to a sensor that was scratched one time. A fifth curve 1610 corresponds to a sensor that was dragged half way through the distance (i.e., subjected to "half a scratch" compared to the sensor that corresponds to the fourth curve). A sixth curve 1612 corresponds to a sensor that was not scratched (not damaged.)

The impedance curves 1602, 1604, 1606, 1608, 1610, 1612 have relatively closely-grouped impedance values below 100 kHz and above 10,000 Hz, but the impedance values spread out between 100 Hz and 10,000 Hz. For example, at 1000 Hz, the first curve 1602 (corresponding to the most damaged sensor) has an impedance value of about 100 kΩ, the second curve 1604 has an impedance value of about 105 kΩ, the third curve 1606 has an impedance value of about 122 kΩ, the fourth curve 1608 has an impedance value of about 140 kΩ, the fifth curve 1610 has impedance value of about 155 kΩ, and the sixth curve 1612 (corresponding to the undamaged sensor) has an impedance value of about 160 kΩ.

In some examples, measuring impedance at a portion of the impedance-frequency curve where the impedance spread is present may allow for characterization of an amount of damage to a sensor. For example, impedance may be determined for a sensor at above 250 Hz, e.g., at 1000 kHz, and the impedance may be compared to a reference value or look-up table to ascertain a damage state of the sensor or to determine a sensitivity of the sensor to an analyte (e.g., glucose). Determining impedance at a relatively high frequency (e.g., over 250 Hz, or at 1000 Hz) may avoid effects from the double-layer capacitance, because the membrane acts like a high-pass filter.

In some examples, a sensor may be characterized by a difference in impedance values at two different frequencies. For example, a difference between the impedance at 1000 Hz and the impedance at 100 Hz may be used to determine an extent of damage to a sensor membrane. This difference between impedance values for a sensor at two difference frequencies will be referred to as the "dual frequency impedance," to avoid confusion with the difference in impedance between healthy and damaged sensors (described above), or with the difference in impedance of a particular sensor at two points in time (described below).

Figure 17:
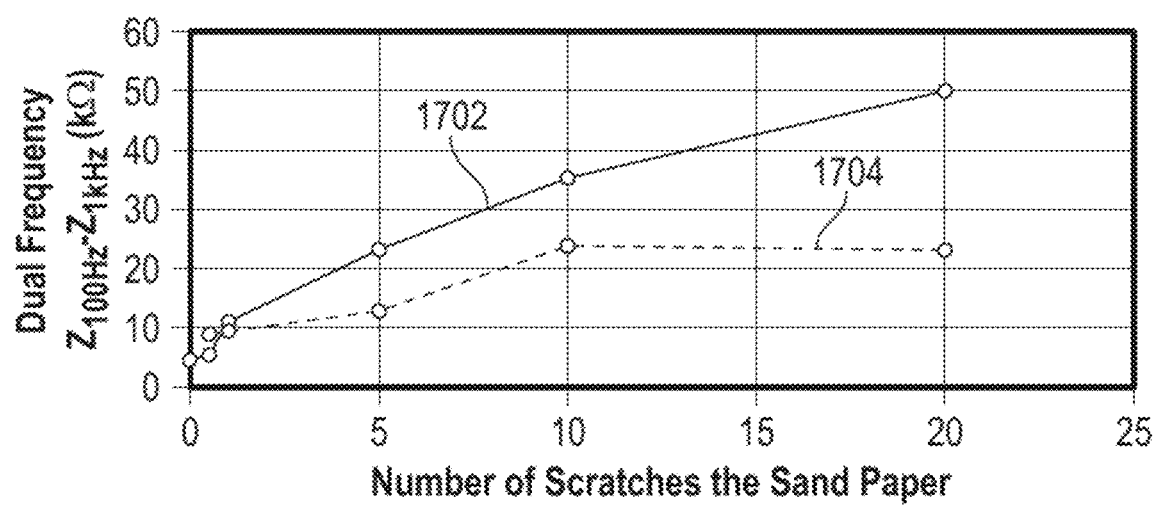
FIG. 17 is a graph that shows dual frequency impedance plotted against the number of scratches through sandpaper to which a sensor was exposed.

FIG. 17 is a graph that shows the dual frequency impedance (in this case, the impedance at 100 Hz minus the impedance at 1 kHz) plotted against the number of scratches through sandpaper to which a sensor was exposed, which correlates with the amount of damage to the sensor. A first curve 1702 indicates the dual frequency impedance measured immediately after the sensor was brought in contact with a solution. A second curve 1704 indicates the dual frequency impedance measured after soaking overnight in a solution. The dual-frequency impedance is larger immediately after the sensor is immersed in solution than after the overnight soak. This indicates that dual frequency impedance based on measurements taken during a manufacturing process, without an extending soaking period, may be used to identify abnormal or damaged sensors. It also indicates that a dual frequency impedance based on impedance measurements taken soon after insertion of a sensor into interstitial fluid in a host may be used to assess sensor health (e.g., quickly determine whether a sensor is damaged, so it may be replaced).

Figure 18A:
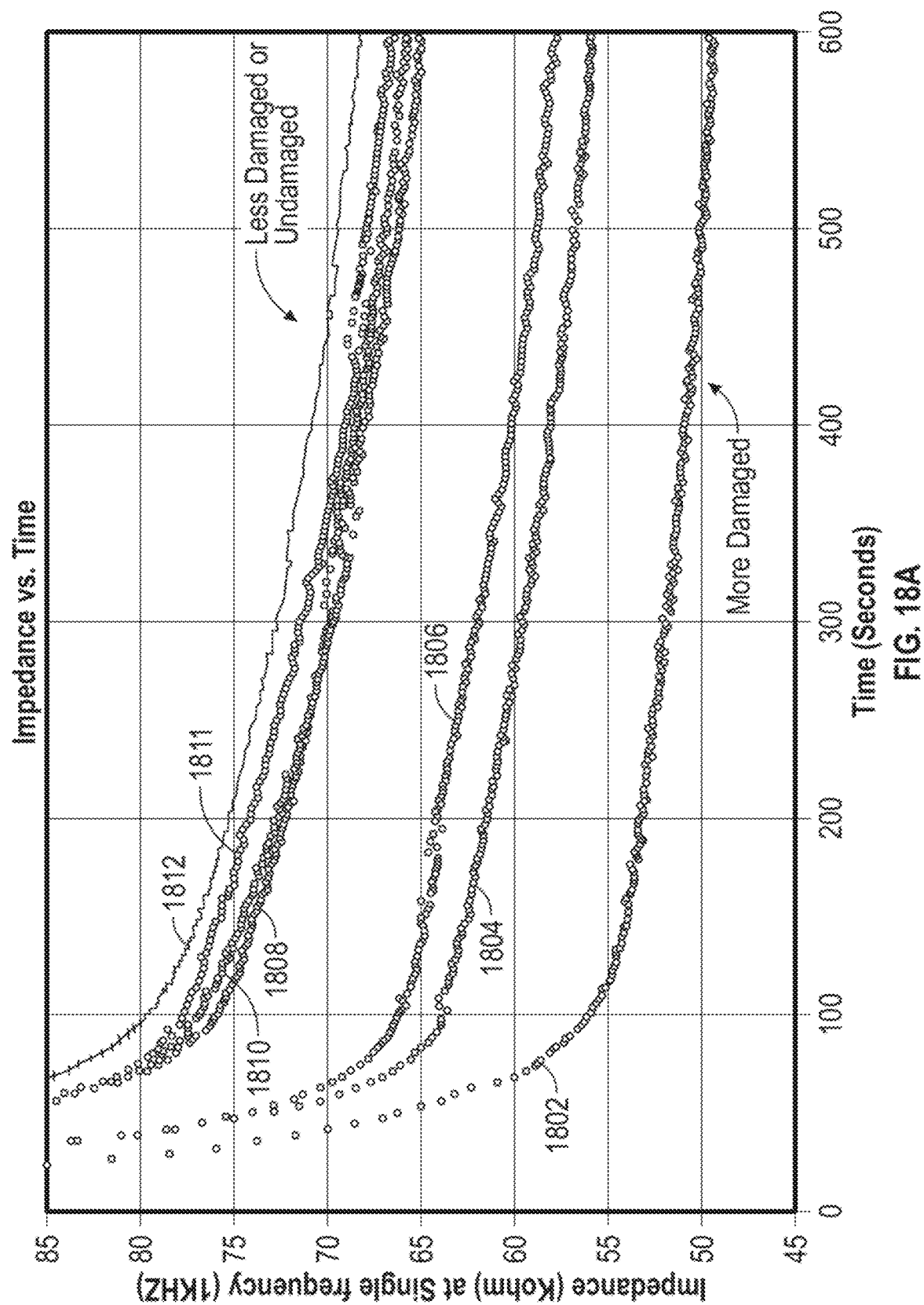
FIG. 18A is a graph that shows impedance at 1 kHz plotted against time for a number of sensors with varying degrees of damage.

FIG. 18A shows impedance at 1 kHz plotted against time for a number of sensors with varying degrees of damage. The impedance was determined using methods described above (e.g., based on current measurements and an applied voltage). The time indicates the amount of elapsed time after insertion in a hydrating solution. Curve 1802 corresponds to a sensor with a relatively large degree of damage. Curve 1812 corresponds to a sensor with no damage. The curves in between correspond to sensors with varying degrees of damage, with more-damaged sensors being closer to curve 1802. Curve 1802 corresponds to a sensor that was scratched 20 times (as described above). Curve 1804 corresponds to a sensor that was scratched 12 times. Curve 1806 corresponds to a sensor that was scratched 8 times. Curve 1808 corresponds to a sensor that was scratched 4 times. Curve 1810 corresponds to a sensor that was scratched 2 times. Curve 1811 corresponds to a sensor that was scratched one time. FIG. 18A shows that, for each sensor (damaged, slightly damaged, and undamaged) the impedance drops rapidly in the first 100 seconds after immersion, and then continues to drop at a slower rate for the next 500 seconds.

Figure 18B:
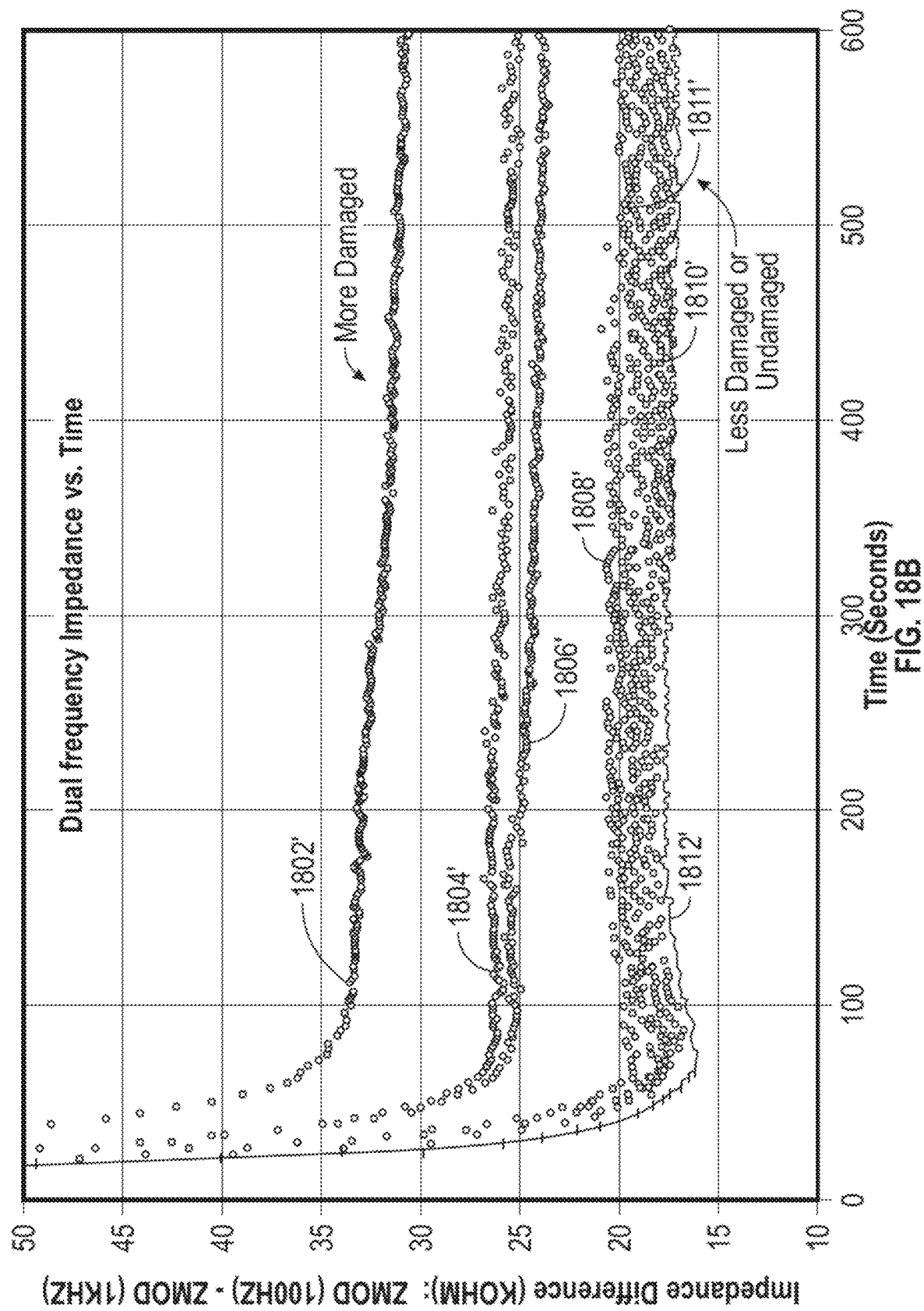
FIG. 18B is a graph that shows the dual frequency impedance for 100 Hz and 1000 Hz for the same sensors as shown in FIG. 18A.

FIG. 18B shows the dual frequency impedance for 100 Hz and 1000 Hz (i.e., the difference in impedance at 100 Hz and the impedance at 1000 Hz) for the same sensors as shown in FIG. 18A. Curve 1802', for example, represents the dual frequency impedance for the same sensor as curve 1800 in FIG. 18A, and curve 1812' represents the dual frequency impedance for the undamaged sensor corresponding to curve 1812. FIG. 18B shows that, for each sensor (damaged, slightly damaged, and undamaged), the dual frequency impedance drops rapidly in the first 100 seconds after immersion. The undamaged and slightly damaged sensors (e.g., as represented by curves 1812', 1810', 1811') reach a dual frequency impedance low point at about 75 seconds, after which the dual frequency impedance is relatively stable. The impedance values are relatively stable after 100 seconds, with more damaged sensors showing a slowly dropping dual frequency impedance over time. The relatively stable dual frequency impedance values over the 100 to 600 second time period may allow for differentiation or characterization of sensor damage based on the impedance value, with little sensitivity to the exact time of measurement or temporal variations in sensor response to immersion. The position of the dual frequency impedance value on a dual frequency impedance spectrum may be used to determine the presence or severity of damage. For example, with reference to FIG. 18B, a sensor with a dual frequency impedance of greater than 65 kOhm may be taken as severely damaged (or having a severe manufacturing abnormality), a sensor having an dual frequency impedance below 55 kOhm may be taken as undamaged, or very slightly damaged (and therefore usable, potentially with compensation), and sensors with an dual frequency impedance between 55 kOhm and 65 kOhm may be taken as moderately damaged (and potentially usable with compensation).

Because the dual frequency impedance stabilizes more quickly after contact with solution than simple impedance, the dual frequency impedance may be more preferred than impedance as measure of sensor damage. For example, a predictable steady state range may be determined more easily using dual frequency impedance, or a measurement may be taken over a shorter dwell time because dual frequency impedance stabilizes more quickly than impedance.

Dual frequency impedance may be particularly useful in evaluating sensor health after insertion in a host. When a sensor is inserted into a host, the exact insertion time may not be known if the sensor does not have its own clock or sensor electronics to track time. For example, sensor electronics may be coupled to an inserted sensor an unknown period of time after sensor insertion (i.e., the user may insert the sensor, but may not immediately couple sensor electronics (e.g., a transmitter) to the inserted sensor). As a result, the exact dwell time may not be known. The dwell time (after insertion) may be a few seconds, or a minute, or a few minutes, or longer, depending on the habits or behavior of the user. The sensor impedance data may eventually become available when the sensor electronics are attached, but the length of time since insertion may be unknown, which means that impedance may not be indicative of the amount of sensor damage. For example, with reference to FIG. 18A, an impedance value of 70 kOhm at 1 kHz could correspond to any of the plotted sensors (e.g., heavily damaged sensor curve 1802 has a value of about 70 kOhm at about 60 seconds, and undamaged sensor curve 1812 has a value of 70 kOhm at about 450 seconds).

Because the precise dwell time may not be known, it may be desirable to detect a failed or damaged sensor without using a precise time-since-insertion value as an input. For example, it may be desirable to use a steady-state parameter that is reliably steady a short time after sensor insertion. In some examples, it may be preferable to determine sensor health based on dual frequency impedance (shown in FIG. 18B) as opposed to impedance (shown in FIG. 18A) to take advantage of the relatively stable values after a short period of time. In an example, a sensor system may use a dual frequency impedance value determined a specified period of time (e.g., 72 seconds or 100 seconds) after connection of a sensor to sensor electronics (which may start a clock) to assure that the sensor has reached a stable point in the dual impedance curve.

Figure 19A:
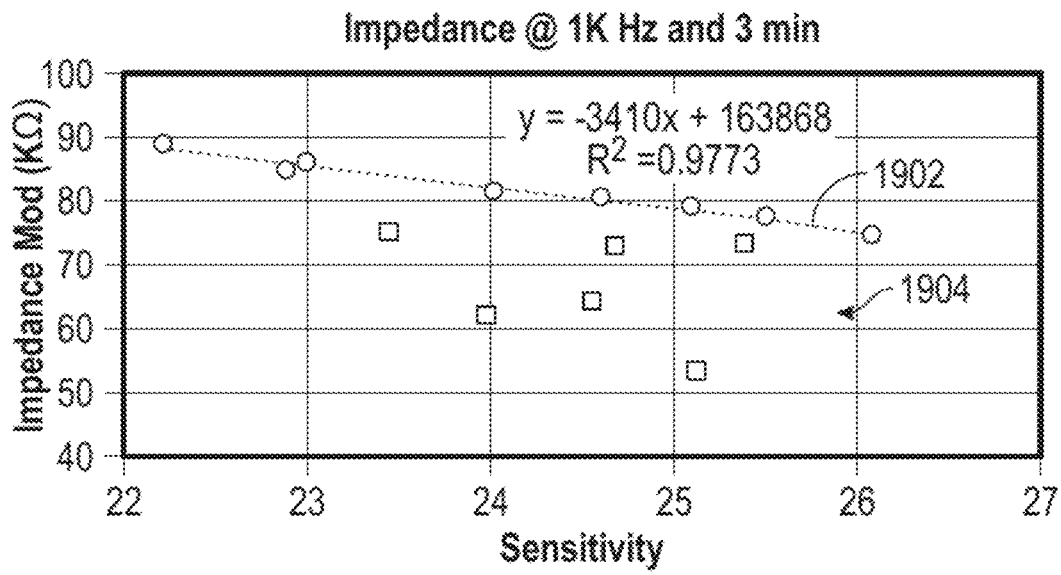
FIG. 19A is a graph that shows sensor impedance at 1000 Hz plotted against a sensitivity for a number of sensors, with measurements taken three minutes after sensor insertion.

FIG. 19A shows sensor impedance at 1000 Hz plotted against a sensitivity (e.g., nA/mg/dL) for a number of sensors, with measurements taken three minutes after sensor insertion. Healthy sensors, which have little or no damage, are indicted by circles, and unhealthy (e.g., significantly damaged) sensors are indicated by squares. The healthy sensors 1902 fall near a line determined by a linear function. The unhealthy sensors 1904 fall below the line. The relative placement of a particular sensor impedance on the chart shown in FIG. 19A may be used to identify unhealthy sensors. For example, damaged sensors may be identified based upon the distance from the healthy sensor line.

Figure 19B:
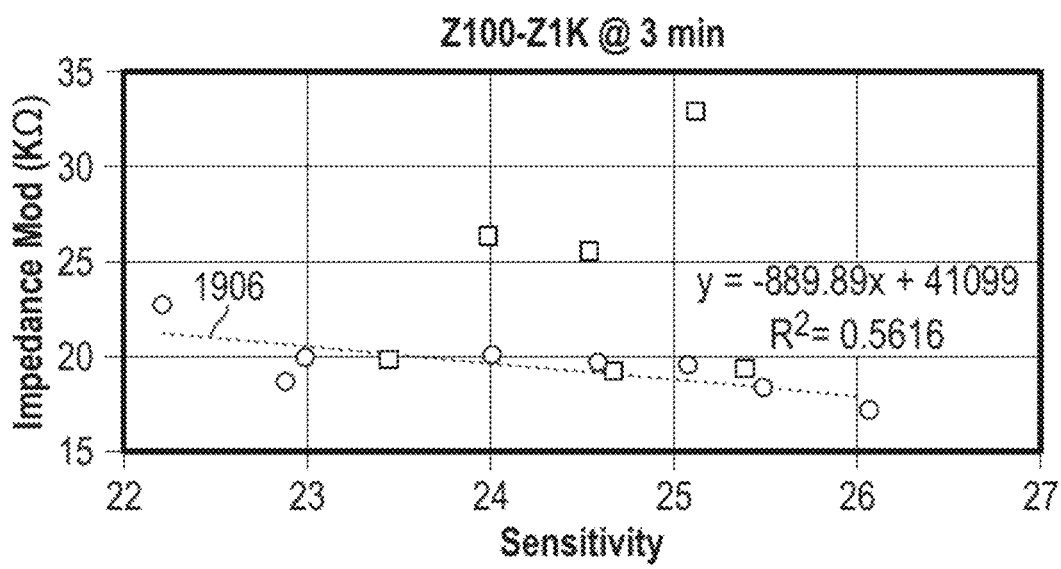
FIG. 19B is a graph that shows dual frequency impedance plotted against sensitivity, for measurements taken three minutes after immersion in fluid.

FIG. 19B shows dual frequency impedance plotted against sensitivity, for measurements taken three minutes after immersion in fluid. Sensors that are displaced from a healthy sensor line 1906 (e.g., above a defined range) may be identified as damaged or abnormal. FIG. 19B suggests that a damage assessment based on the position of a sensor on a dual-frequency impedance vs. sensitivity has good specificity (all three sensors that are spaced from the healthy sensor line are damaged or abnormal) but moderate sensitivity (only three out of six damaged sensors were identified). Dual frequency and impedance and sensitivity may be used alone to identify damaged sensors, or in combination with one or more other techniques, which may identify the other three abnormal sensors that are "missed" (not clearly identifiable as abnormal) in the FIG. 19B plot.

Figure 20A:
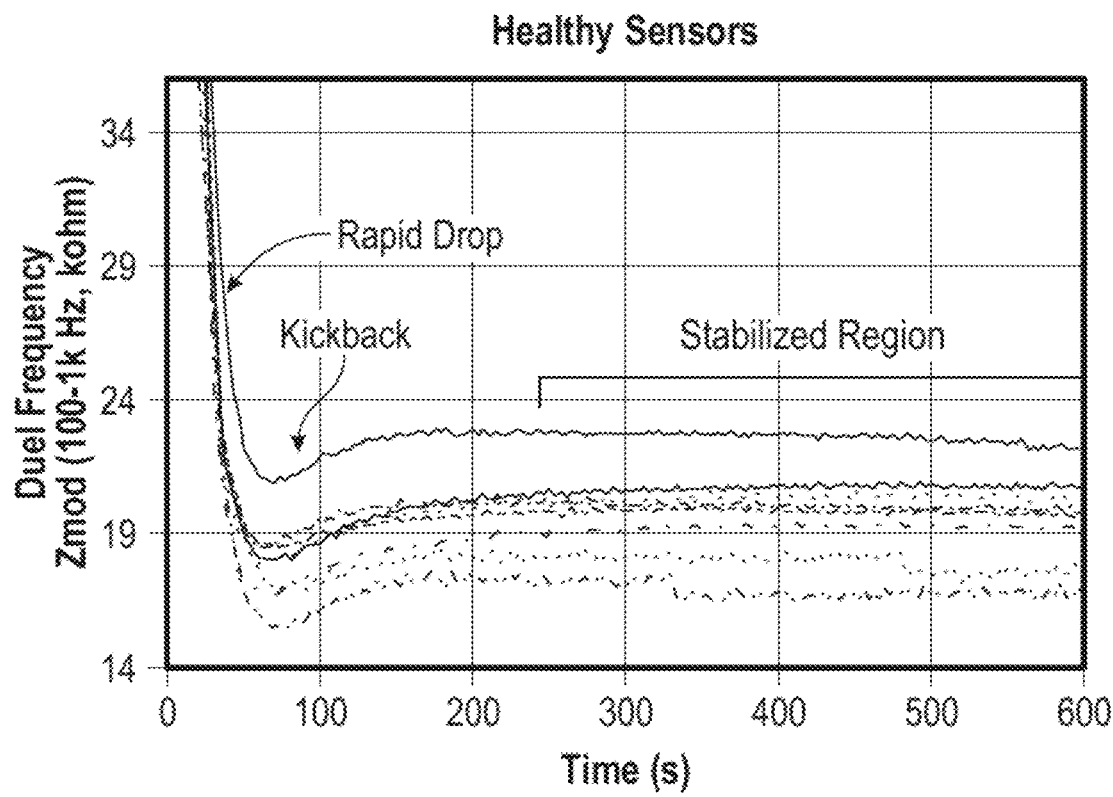
FIG. 20A is a graph that shows dual frequency impedance plotted against time for a number of healthy sensors.

FIG. 20A shows dual frequency impedance plotted against time for a number of healthy sensors. As with the previous disclosure, the dual frequency impedance is the impedance at 100 Hz minus the impedance at 1000 Hz. Other frequencies may also be used, as described in reference to FIG. 16. FIG. 20A shows that the dual frequency impedance drops quickly in the first 50 seconds and then increases slightly ("kickback") before reaching a stabilized state.

Figure 20B:
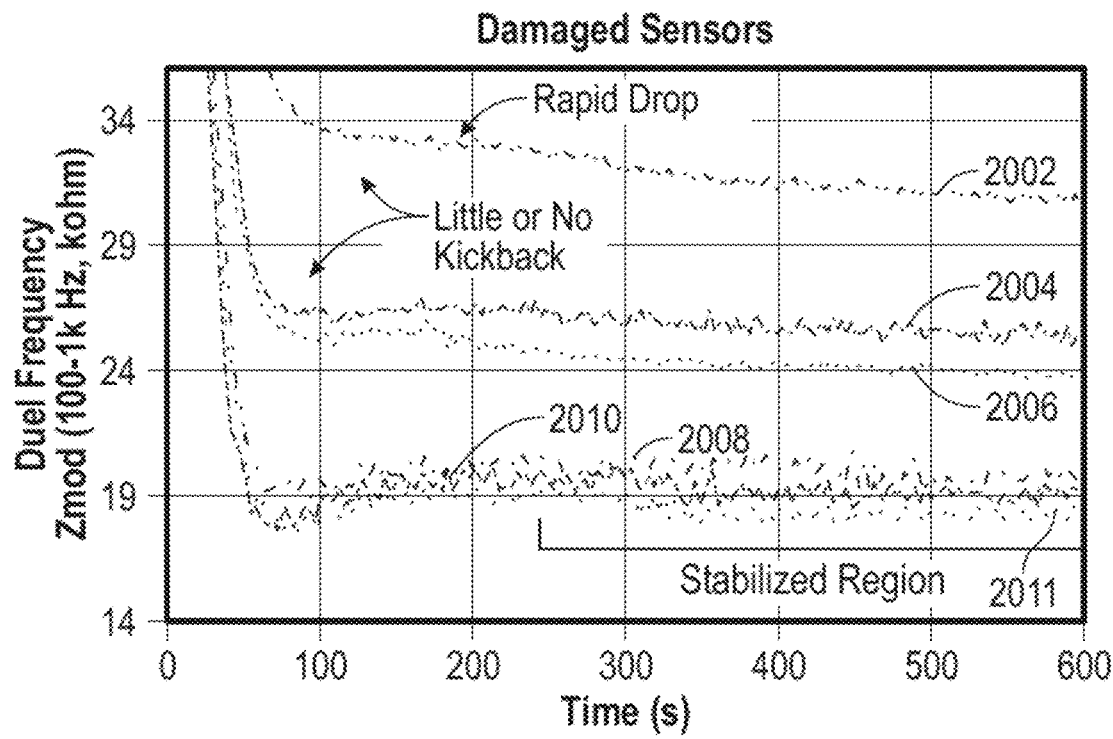
FIG. 20B is a graph that shows dual frequency impedance plotted against time since immersion for a number of damaged sensors.

FIG. 20B shows dual frequency impedance plotted against time since immersion for a number of damaged sensors. The moderately damaged sensors (indicated by curves 2006, 2008, 2010, 2011) show less pronounced kickback, and heavily damaged sensors (indicated by curves 2002, 2004) show little to no kickback. In some examples, the presence or amount of damage in a sensor may be determined based at least in part on the presence or amount of kickback present in a dual frequency impedance curve. For example, a difference between a dual frequency impedance at a specified time after insertion (which may be selected for example based upon the typical low point in the curve shown in FIGS. 20A and 20B) may be compared to a dual frequency impedance at a later time (or earlier time). In some examples, a plurality of impedance values may be measured at two or more frequencies and sequential times, so that a low point on a dual frequency impedance curve may be identified or estimated for a specific sensor being assessed, and a later dual frequency impedance may be compared to a low point to assess the amount or presence of kickback, from which an amount or presence of damage may be inferred.

Figure 20C:
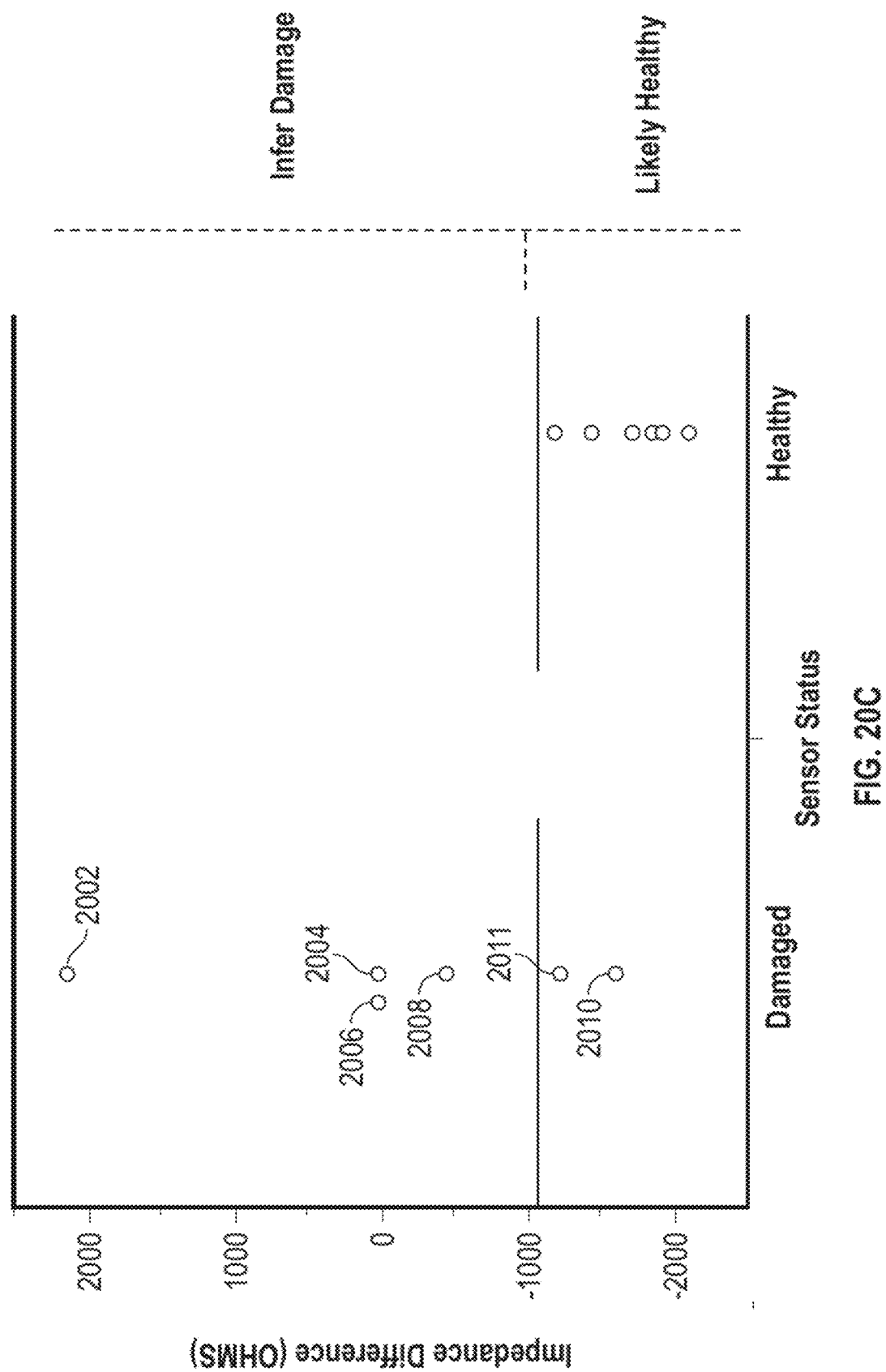
FIG. 20C is a graph that shows the difference between dual-frequency impedance at 72 seconds after immersion and at 180 seconds after immersion, for the healthy sensors of FIG. 20A and the damaged sensors of FIG. 20B.

FIG. 20C shows the difference between dual-frequency impedance at 72 seconds after immersion and at 180 seconds after immersion, for the healthy sensors of FIG. 20A and the damaged sensors of FIG. 20B. The low-point of dual-frequency impedance for both groups of sensors (healthy and damaged) is approximately 72 seconds after immersion. At 180 seconds, the dual frequency impedance has stabilized in both groups. Sensor data points for damaged sensors in FIG. 20C are labeled with reference numbers to indicate the respective corresponding curves on FIG. 20B.

FIG. 20C shows that a difference between dual frequency impedance at a low point (e.g., 72 seconds) and a dual frequency impedance at a steady state (e.g., 180 seconds) may be used to identify damaged sensors. For example, a threshold may be defined, and sensors having a difference in dual-frequency impedance for specified measurement times (e.g., 72 seconds and 180 seconds for the illustrated data) that exceeds the threshold may be deemed damaged (or excessively damaged). In various examples, sensors having an difference in dual-frequency impedance that is below (less than) the threshold may be deemed healthy, or likely healthy (e.g., not damaged, or having minimal damage or abnormality that does not prevent use of the sensor), or in need of further evaluation to ascertain status (e.g., a second technique may be used to identify the sensors corresponding to curves 2010, 2011 that were not identified as damaged).

With reference to FIG. 20C, the threshold may, for example, be negative one-thousand ohms (−1050Ω). The specific impedance-difference threshold may be determined experimentally using a group of sensors with known damaged states (e.g., as determined by a microscope inspection or deliberate damage to the sensors). The threshold may depend at least in part on the design of the sensor (e.g., sensor size), the membrane (e.g., membrane thickness or composition), the specified measurement times (e.g., 72 seconds and 180 seconds were selected for the example data). The precise measurement time may differ, or may be a range, or may be determined from sensor data. For example, the measurement time may be an estimated low point in a dual-frequency impedance curve, and a specified amount of time later (e.g., 108 seconds after the low point).

The chart in FIG. 20C shows good specificity for identifying damaged sensors and reasonably good sensitivity (four out of six) for damaged sensors. In some examples, additional information may be combined with the dual frequency impedance to improve the performance, e.g., to increase the sensitivity of a system to identification of an excessively damaged sensor. For example, a sensor assessment may be based on two or more of: sensor impedance at one or more specified times after a specified event; an impedance difference at two different times; a dual frequency impedance; a difference in dual frequency impedance at two different times; a first derivative of impedance, impedance difference, or dual-frequency impedance; a second derivative of impedance, impedance difference or frequency impedance; a higher order derivative of impedance or impedance difference; or a variability in a signal or variability in a derivative of a signal. A sensor assessment also be based on more than two frequencies, or more than two measurement times.

Figure 21A:
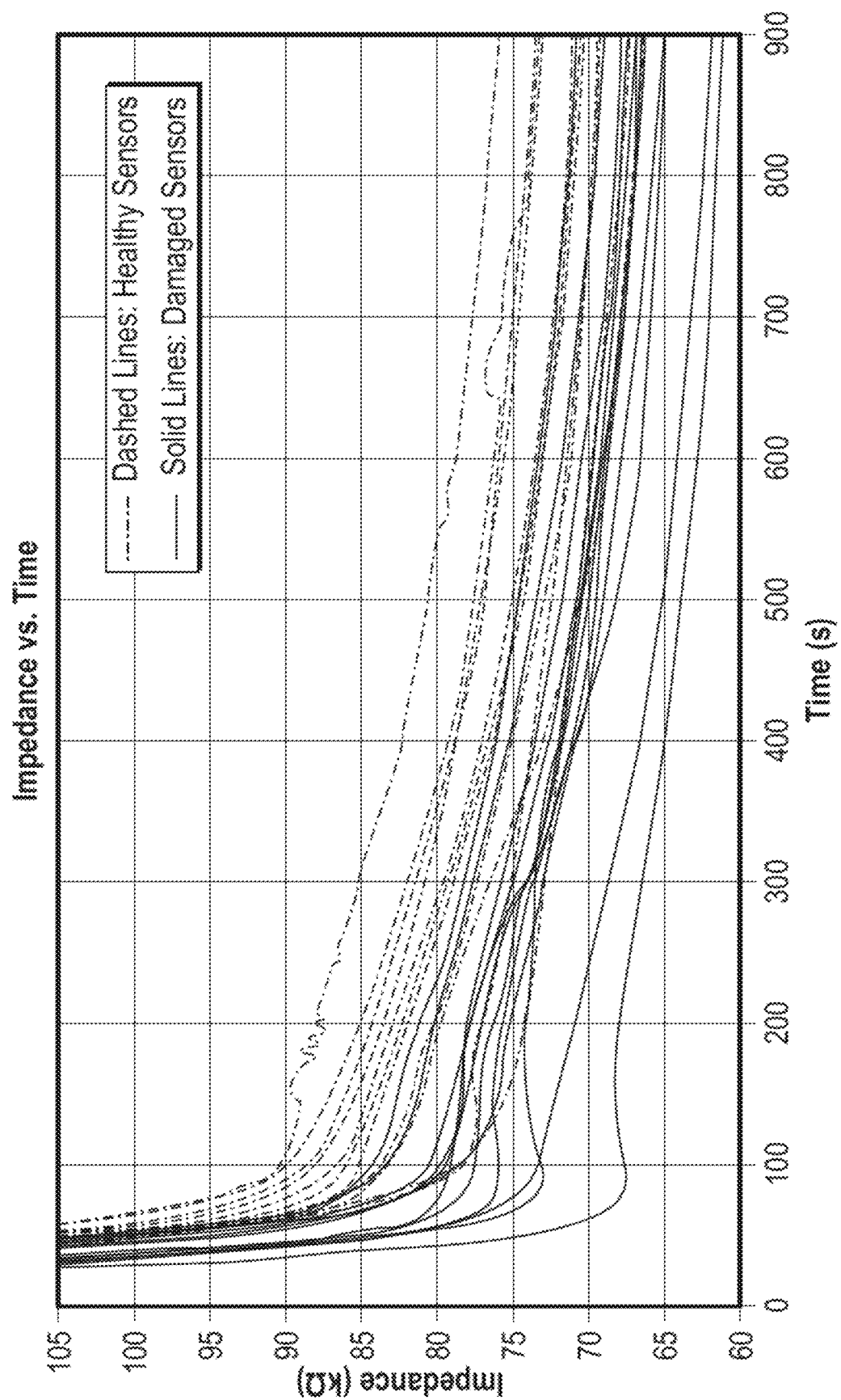
FIG. 21A is a graph that shows impedance plotted against time for healthy sensors (indicated by dashed lines) and damaged sensors (indicated by solid lines).

FIG. 21A shows impedance plotted against time for healthy sensors (indicated by dashed lines) and damaged sensors (indicated by solid lines.) The data in FIGS. 21A-21H was obtained using sensors that were damaged by scraping across sandpaper, as described above. FIG. 21A shows that impedance tends to be lower for damaged sensors, with some overlap at the outer bounds of the impedance distribution. Between 100 seconds and 900 seconds after immersion in fluid, some damaged sensors have an impedance that is higher than some of the healthy sensors.

Figure 21B:
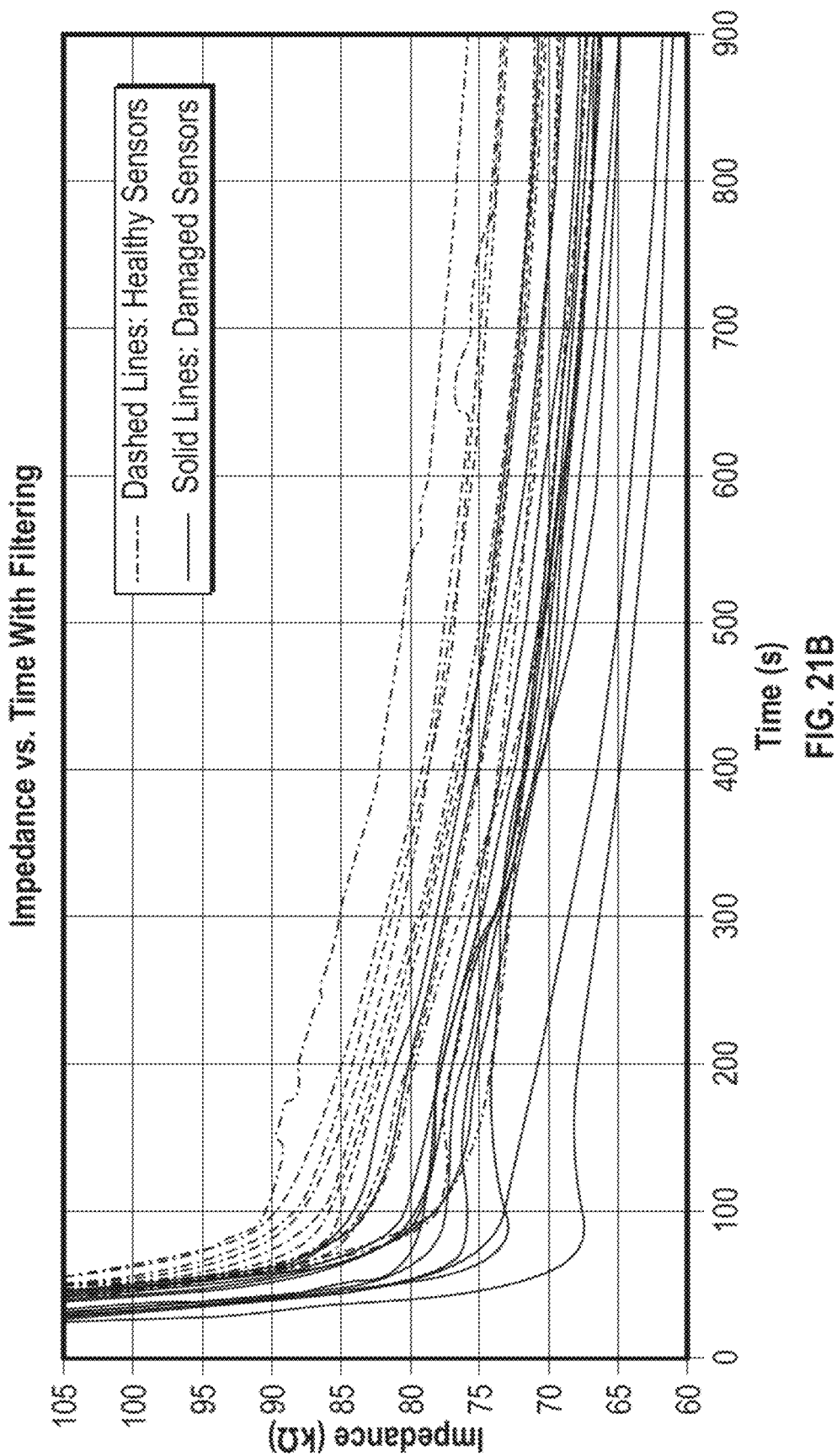
FIG. 21B is a graph that shows impedance plotted against time, with filtering applied to the data.

FIG. 21B shows impedance plotted against time for the same group of sensors, with filtering applied to the data. It can be seen, for example, that some signal variability (e.g., noise) has been removed for several of the healthy sensors between 100 and 200 seconds after immersion. Filtering may be accomplished, for example, using Savitzky-Golay filtering, which was applied to produce the plot shown in FIG. 21B.

Figure 21C:
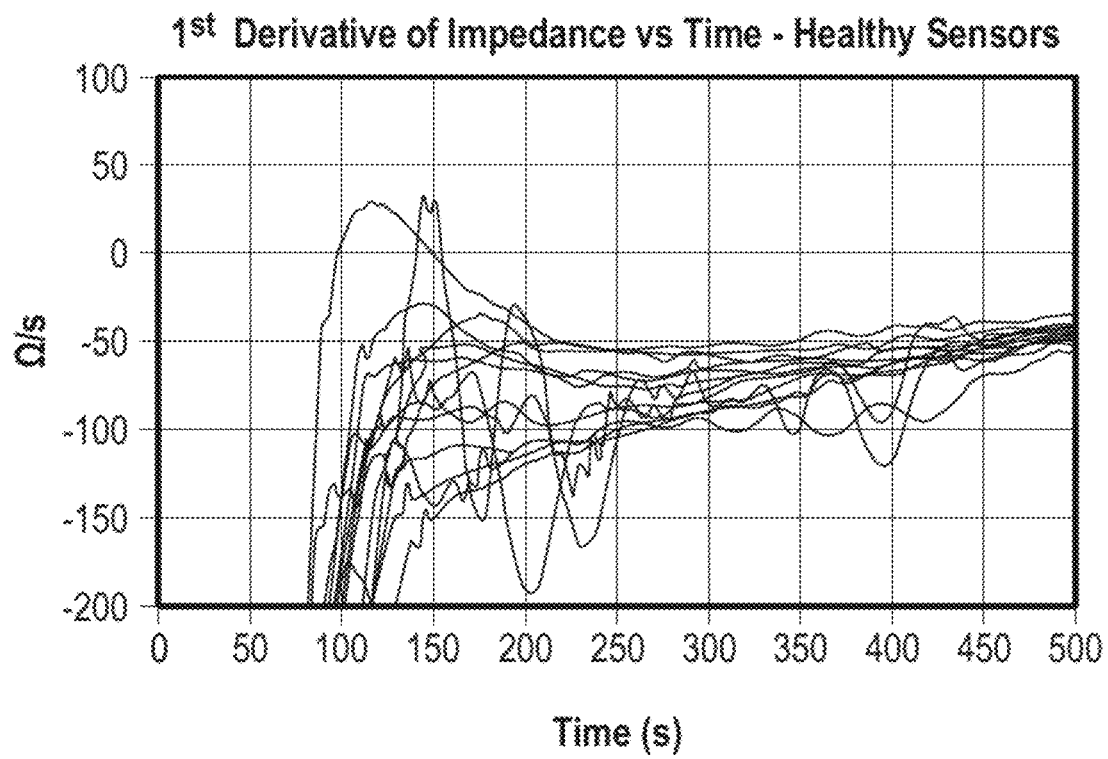
FIG. 21C is a graph that shows the first derivative of filtered impedance (from FIG. 21B) plotted against time, for healthy sensors.
Figure 21D:
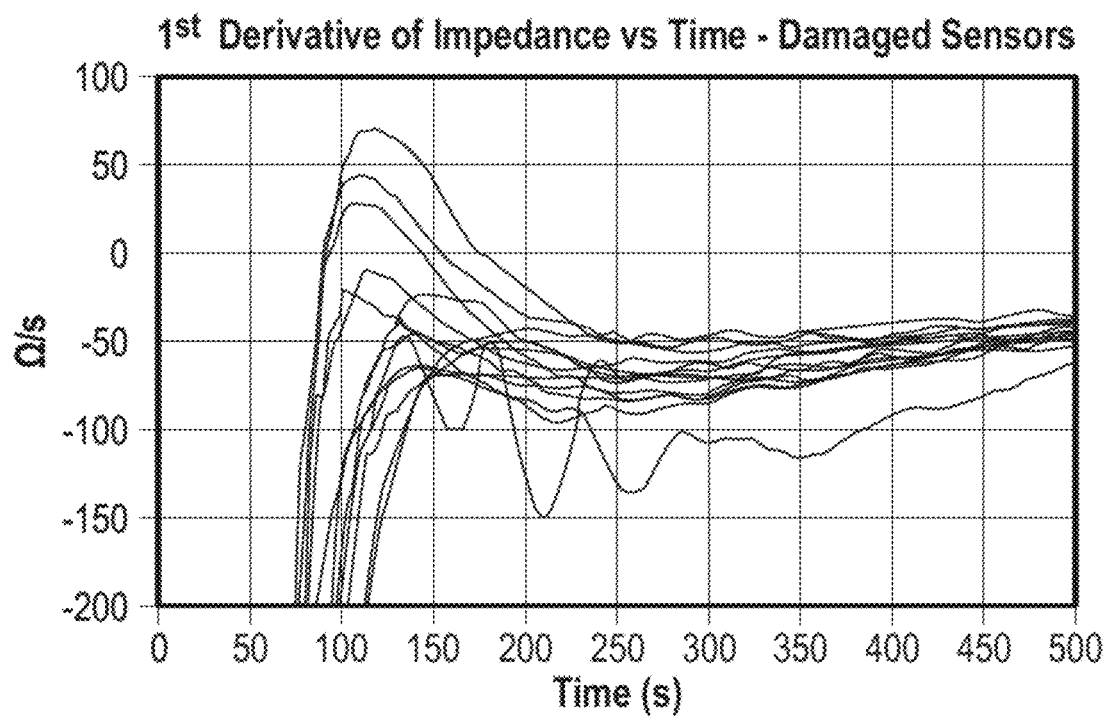
FIG. 21D is a graph that shows the first derivative of filtered impedance plotted against time for damaged sensors.
Figure 21E:
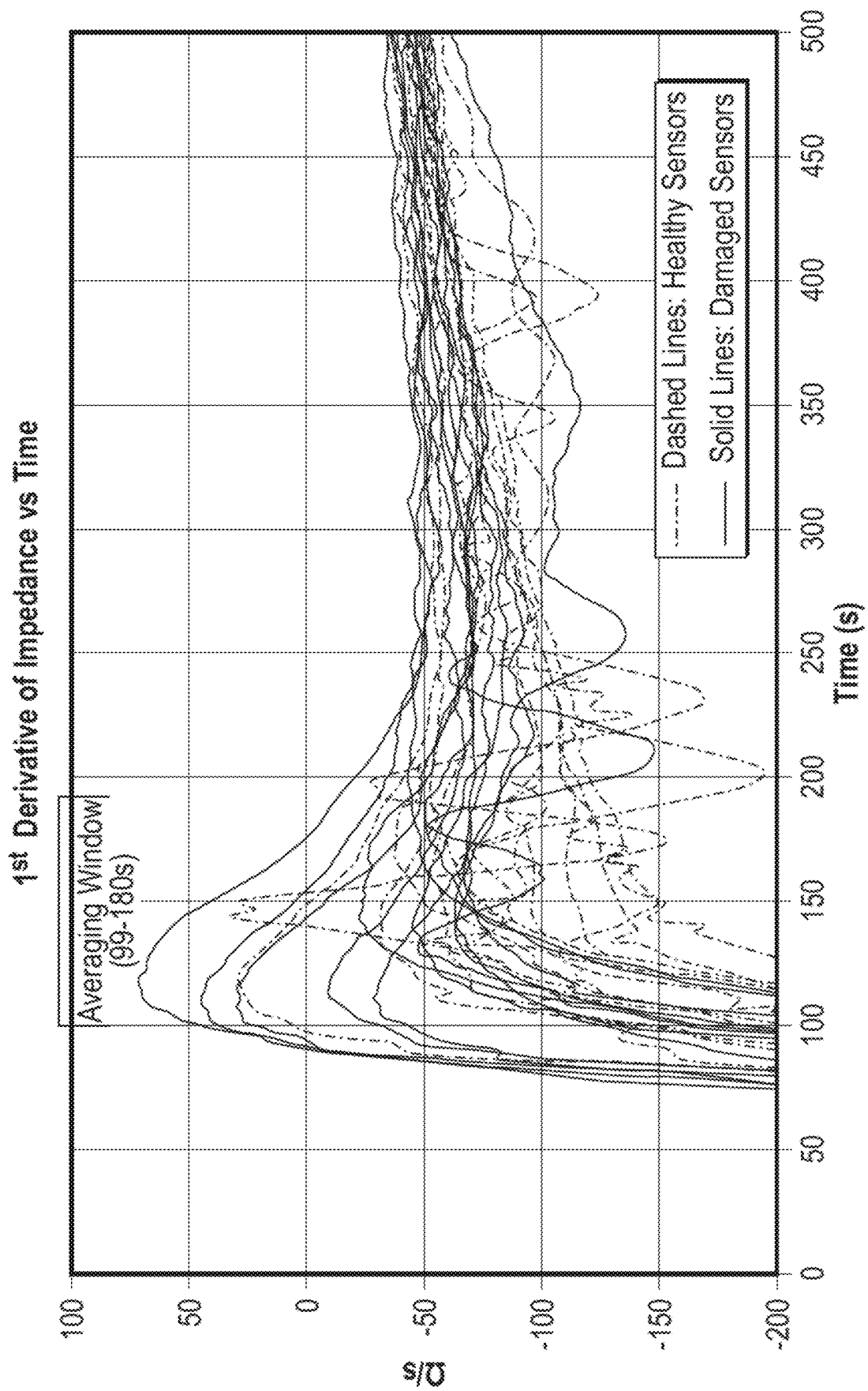
FIG. 21E is a graph that shows the first derivative of filtered impedance for damaged sensors and healthy sensors.

FIG. 21C shows the first derivative of filtered impedance (from FIG. 21B) plotted again time, for healthy sensors. FIG. 21D shows the first derivative of filtered impedance plotted against time for damaged sensors. FIG. 21E shows the first derivative of filtered impedance for damaged sensors and healthy sensors on the same graph (i.e., FIG. 21D overlaid over FIG. 21C).

Differences in features of the first derivative vs. time plot for healthy and damaged sensors may be used to differentiate healthy sensors from damaged sensors. For example, statistical analysis shows that the average of the first derivative values between 99 seconds and 180 second for the damaged sensors is significantly different ($p<0.05$) from the average for healthy sensors over the same averaging window. FIG. 21I shows the average of the first derivative of filtered impedance for this time window (99 to 180 seconds) for a plurality of damaged and healthy sensors. The healthy sensors have a significantly lower average than damaged sensors. While only a fraction of the damaged sensors (5 or 6 out of 14) may be distinguished from healthy sensors using the first derivative method, the method may be combined with other detection methods to increase the success rate of damage detection.

Other averaging time windows may be used, in place of the 99-180 second example described above. In some examples, the end points of an averaging time window may be selected, for example, as a low point for impedance, and a later time point at which the impedance has stabilized (e.g., determined from data as shown in FIGS. 20A and 20B). In other examples, the averaging time window may be determined from experimental data and a first derivative or second derivative of impedance or dual frequency impedance.

Other features of the first derivative data may also be used to differentiate damaged and healthy sensors. For example, the variability of the first derivative may be used as an indicator of sensor health, with lower variability correlated with sensor damage (i.e., sensors with higher variability over a window (e.g., 72 to 180 seconds) are more likely to be healthy).

Figure 21F:
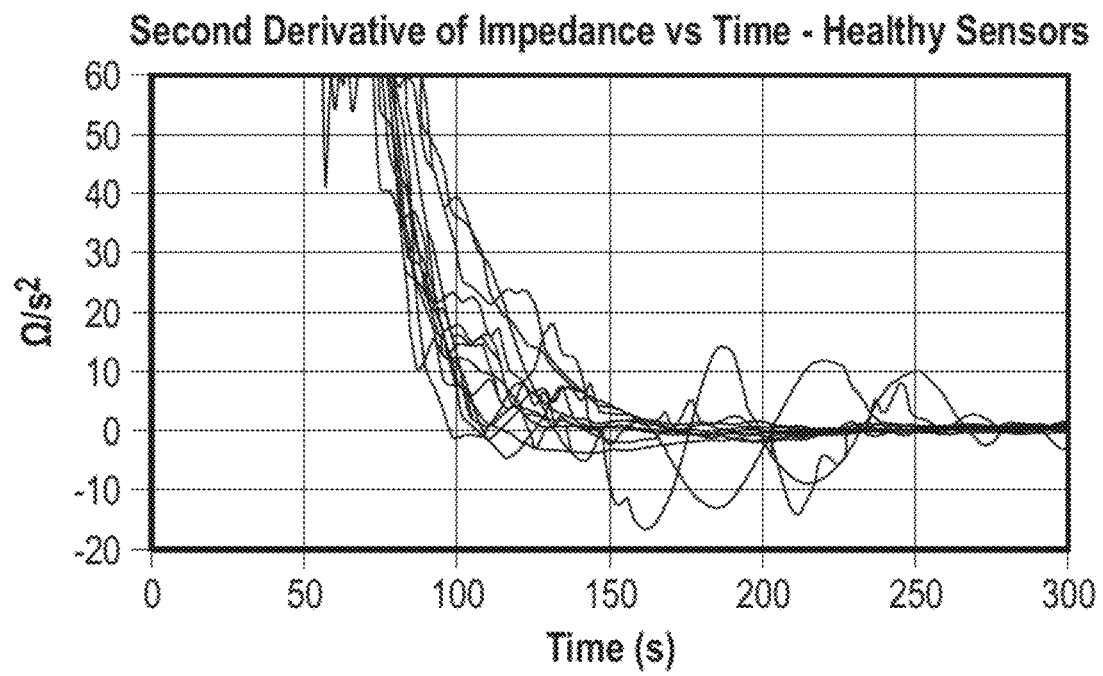
FIG. 21F is a graph that shows the second derivative of impedance plotted against time for healthy sensors.
Figure 21G:
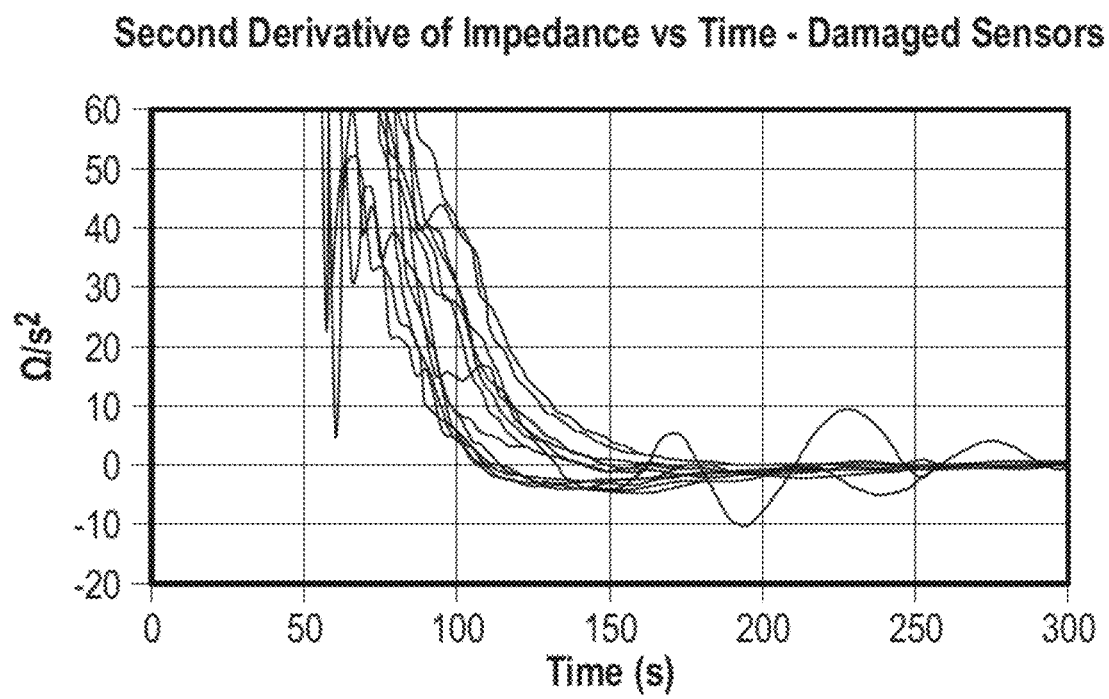
FIG. 21G is a graph that shows the second derivative of impedance plotted against time for damaged sensors.
Figure 21H:
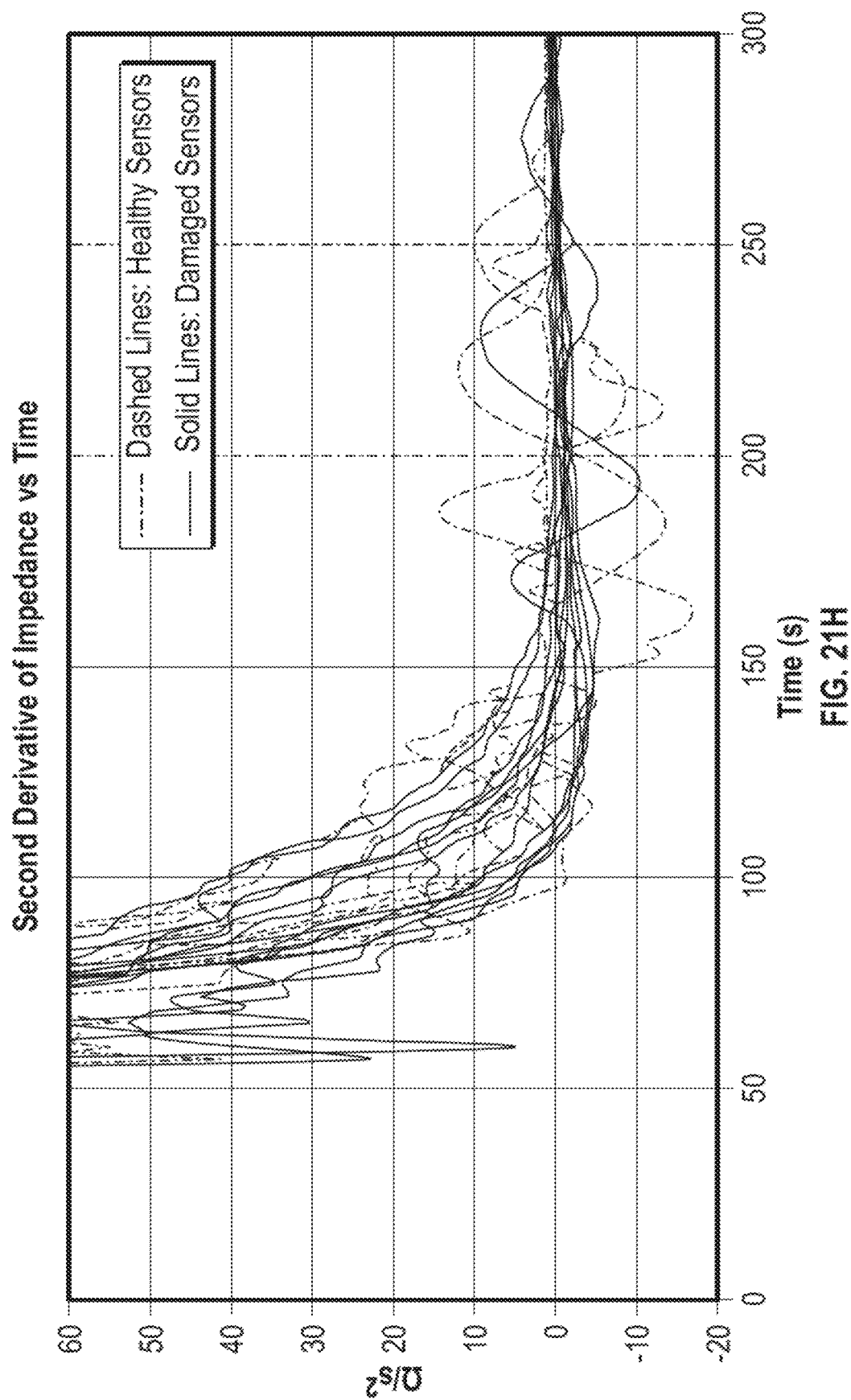
FIG. 21H is a graph that combines the information shown in FIG. 21F and FIG. 21G on the same chart.
Figure 21I:
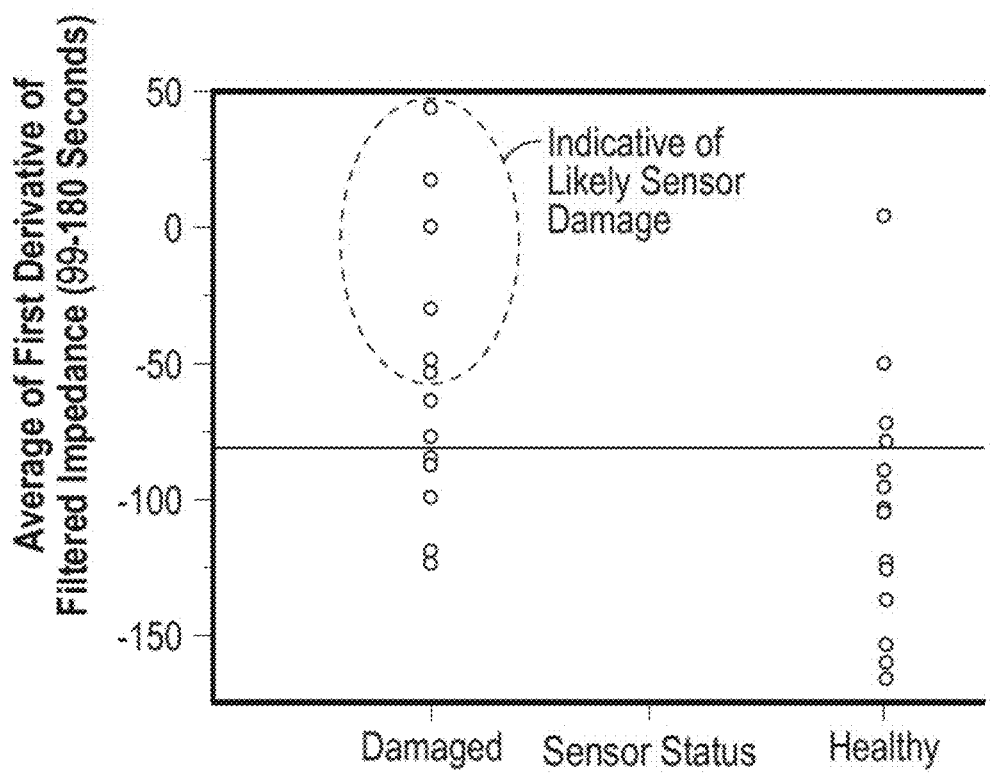
FIG. 21I is a graph that shows the average of the first derivative of filtered impedance for a plurality of damaged and healthy sensors.

FIGS. 21F and 21G show the second derivative of impedance plotted against time for healthy sensors (25F) and damaged sensors (25G), respectively. FIG. 21H shows these groups of second derivative data on the same chart.

Figure 21J:
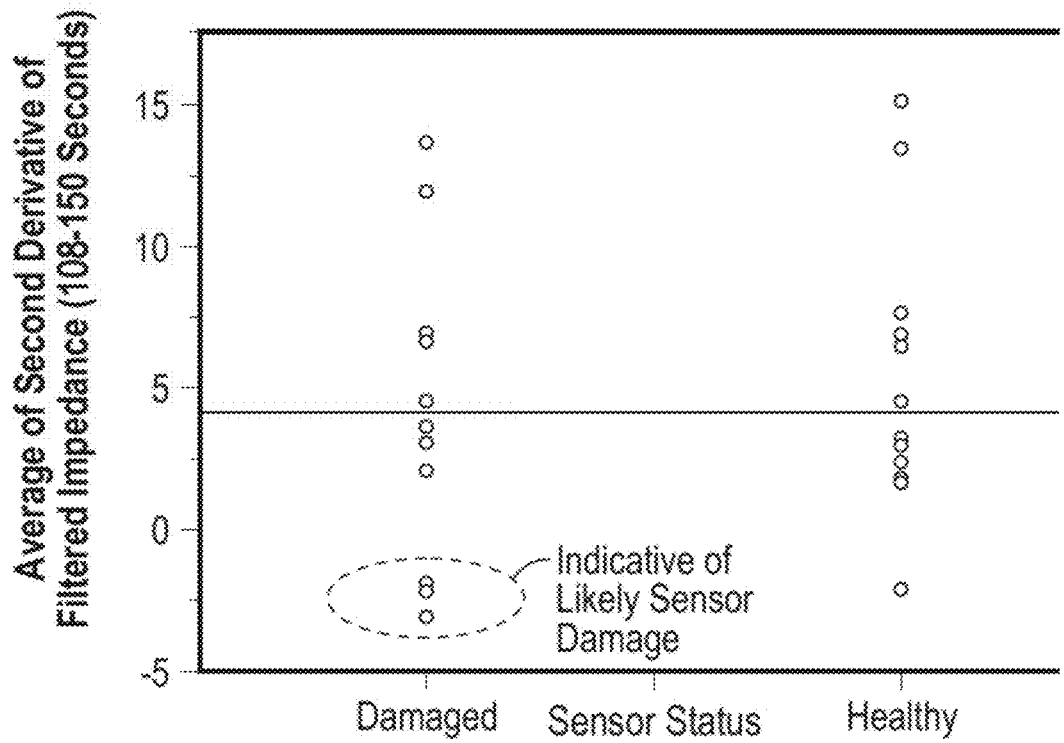
FIG. 21J is a graph that shows the average of the second derivative between 108 seconds and 150 seconds.

Differences in features of the second derivative vs. time plot for healthy and damaged sensors may be used to differentiate healthy sensors from damaged sensors. FIG. 21J shows the average of the second derivative between 108 seconds and 150 seconds. Sensors with a low average are more likely to be damaged.

In another example, the variability in the second derivative over a specified time period (e.g., 108 seconds to 150 seconds, or 100 seconds to 180 seconds) may be assessed as an indicator of sensor damage. A more variable signal indicates a sensor is likely healthy, and a less variable signal indicates that a sensor is likely damaged. This may be a result of interactions within the membrane in healthy sensors, and the relatively smaller impact of such interactions in a damaged membrane, in which more direct access to an electrode may be possible, due to membrane damage.

In some examples, a curve-fitting technique may be used to distinguish healthy sensors from damaged sensors.

In some examples, a curve-fitting technique may be applied to impedance vs. time, first derivative of impedance vs. time, second derivative impedance vs. time, or dual-frequency impedance vs. time. In some examples, a fitted curve or function may be applied to a template or model to determine a sensor's health status (e.g., to declare the sensor state as healthy or unhealthy, or characterize an amount of damage based on a model or a plurality of templates or models corresponding to a spectrum of damage levels). In some examples, one or more parameters (e.g., membrane resistance and pseudo membrane capacitance) extracted from a fitting (e.g., determined function) may be used to distinguish healthy sensors from damaged sensors.

Figure 22:
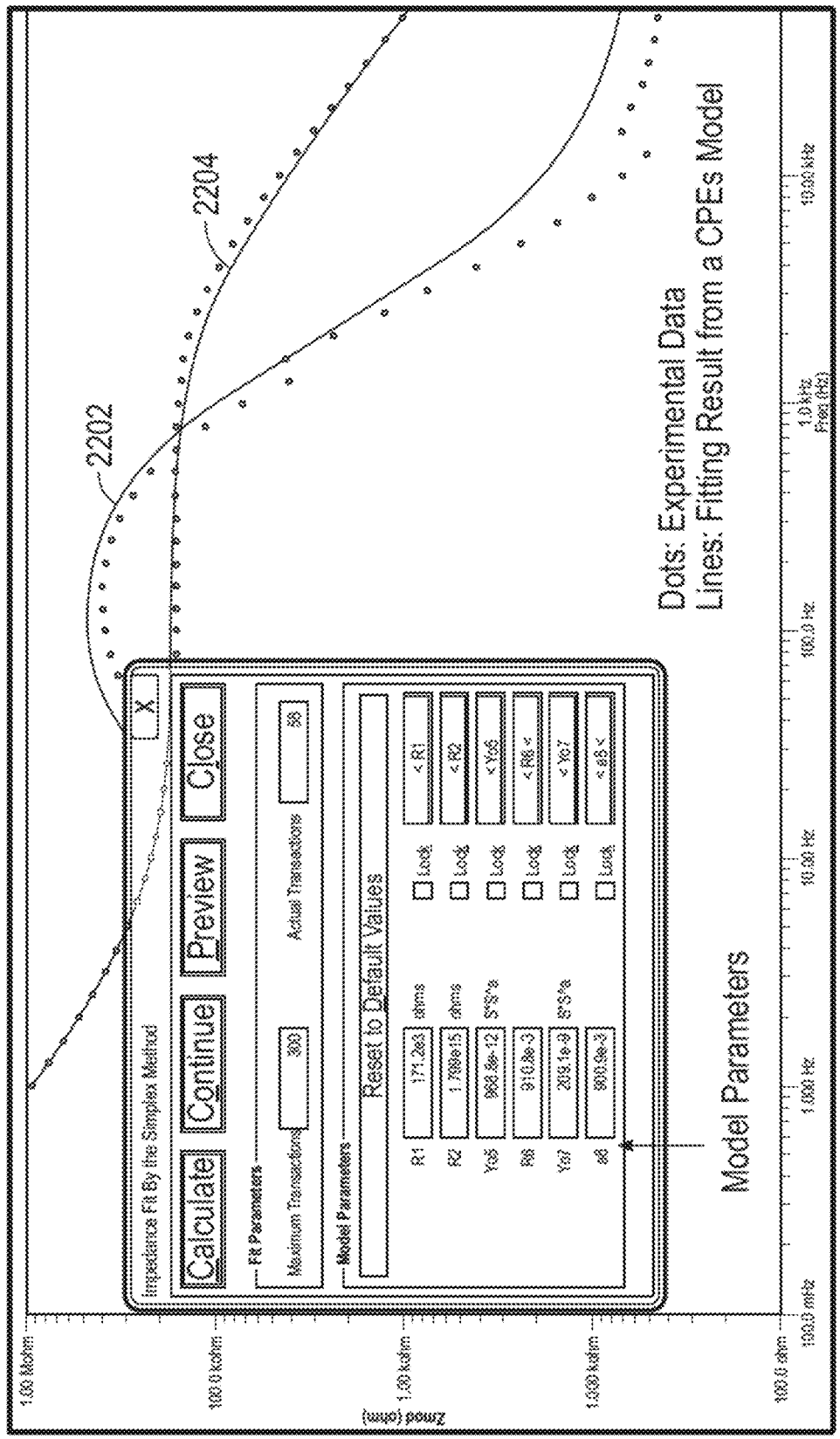
FIG. 22 shows an example curve-fitting for impedance and frequency data.

In some examples, a curve-fitting technique may be applied to an impedance spectroscopy data set (e.g., impedance at a plurality of frequencies). FIG. 22 shows an example curve-fitting, where dots indicate data from sensor testing (e.g., determined impedance values at various frequencies) and lines 2202, 2204 indicate fitted model for the sensor data. Software and a model may be used to determine a fit for the measured sensor data.

Figure 23:
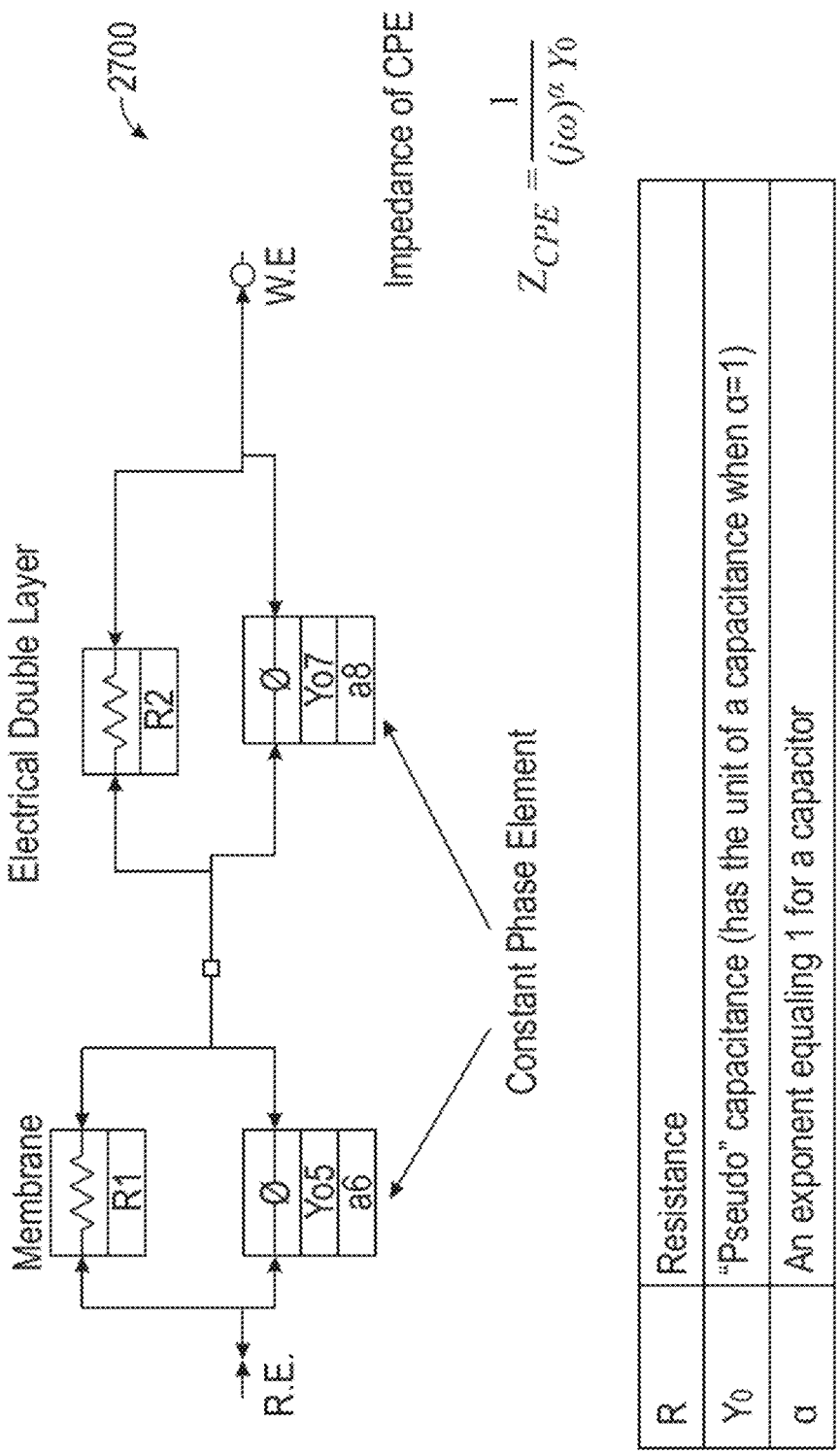
FIG. 23 is a schematic illustration of a constant-phase element (CPE) model.

In some examples, a constant-phase element model may be used to fit impedance spectroscopy data. A capacitor in an electrochemical sensor system may not behave ideally. For example, the double-layer capacitor (described above) formed by a membrane of an analyte sensor may behave according to a constant-phase element model, as opposed to a capacitor. FIG. 23 is a schematic illustration of a constant-phase element (CPE) model 2300, where R is resistance, Yo is a "pseudo" capacitance, and alpha is an exponent that equals 1 for a capacitor. A sensor may be tested to determine impedance across a range of frequencies, a fit may be determined (e.g., using a model), and the sensor may be declared healthy if one or more or a combination of the fitted parameters satisfies one or more health conditions. For example, the tested sensor may be declared healthy based upon a comparison of one or more parameter values to one or more respective thresholds. In some examples, a slightly damaged sensor may be identified based on a condition, and either approved for use, or compensated based on a measure of potential damage such as one or more of the model parameters.

Eight sensors were fitting using the CPE model explained above, where two sensors (denoted A and B) were healthy (undamaged), two sensors (denoted C and D) were badly damaged, and four sensors (E, F, G, and H) were slightly damaged.

Figure 24A:
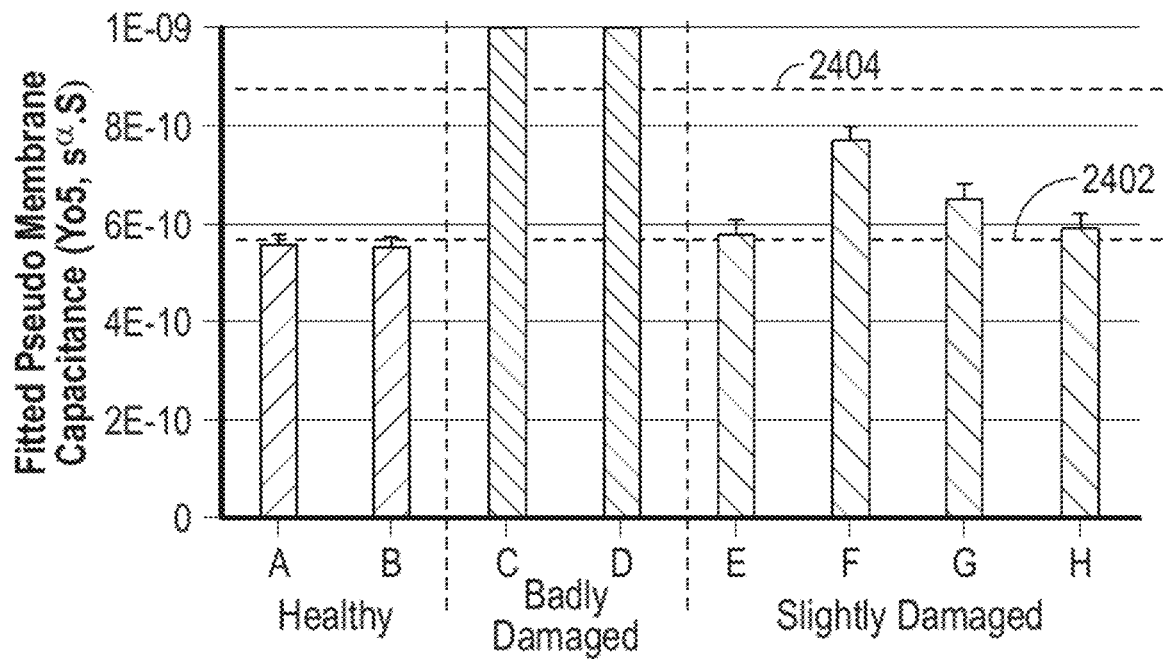
FIG. 24A is a chart that shows fitted pseudo membrane capacitance, determined using a CPE model, for eight sensors.

FIG. 24A shows fitted pseudo membrane capacitance for each of eight sensors, determined using the CPE model described above. The healthy sensors (sensors A and B) have the lowest fitted pseudo membrane capacitance in the group, the heavily damaged sensors (C and D) have the highest fitted pseudo membrane capacitance, and the slightly damaged sensors (E-H) have fitted pseudo membrane capacitance values between values for the healthy sensors and the badly damaged sensors, which indicates that the fitted pseudo membrane capacitance may be used to distinguish healthy sensors from damaged sensors. For example, a sensor may be tested, and a sensor status may be determined based on the fitted pseudo membrane capacitance relative to one or more thresholds, which may be determined from a population of tested sensors with known damage states (e.g., determined from a microscope inspection or protocol for inflicting damage, or both). In an example, a sensor may be declared healthy if the fitted pseudo membrane capacitance is below a first threshold 2402, a sensor may be declared badly damaged responsive to the fitted pseudo membrane capacitance being above a second threshold 2404, and a sensor may be declared slightly damaged (e.g., in need of appropriate compensation) if the fitted pseudo membrane capacitance is between the first and second thresholds 2402, 2404. In various examples, more or fewer threshold may be used, and a threshold may additionally or alternatively be applied to one or more of the other parameters represented in FIGS. 24A-E. In some examples, a probability of sensor damage may be determined based on one or more parameter values. In some examples, an estimate of an extent of sensor damage, or an amount of compensation, may be determined based on one or more parameters values. Such a probability or estimate may be used to determine whether to use a sensor (e.g., designate a sensor for removal from a production process, or indicate to a user to replace the sensor), or whether to apply compensation.

Figure 24B:
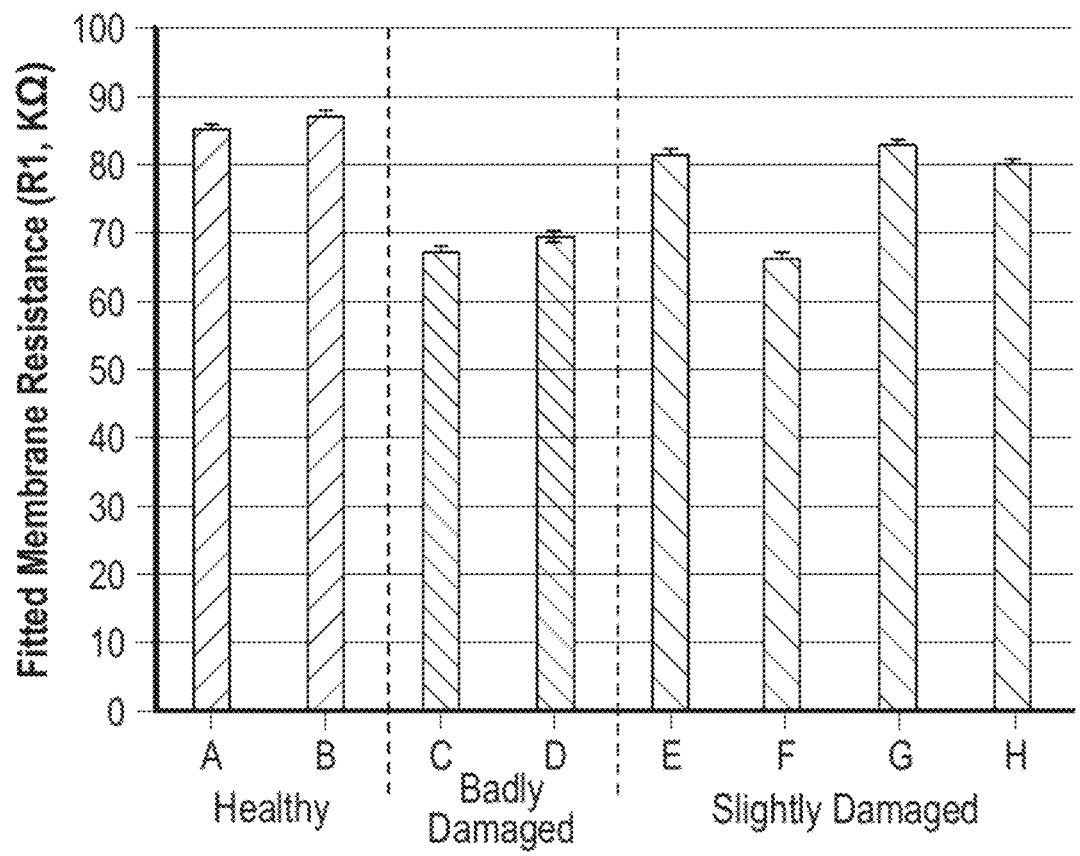
FIG. 24B is a chart that shows fitted membrane resistance for each of the eight sensors (also determined using the CPE model described above.)

FIG. 24B shows fitted membrane resistance for each of the eight sensors (also determined using the CPE model described above). The healthy sensors (sensors A and B) have a fitted membrane resistance that is significantly higher than the fitted membrane resistance of the heavily damaged sensors (C and D). The slightly damaged sensors (E, F, G, H) have an average fitted membrane resistance value that is between the values for the healthy sensors and the values for the badly damaged sensors. These relationships in fitted membrane resistance indicate that the fitted membrane resistance may be used to distinguish healthy sensors from damaged sensors. For example, a sensor may be tested to determine impedance across a range of frequencies, a fit may be determined (e.g., using a model), and the sensor may be declared healthy if the fitted membrane resistance satisfies a health condition. For example, the tested sensor may be declared healthy responsive to the fitted membrane resistance exceeding 82 kiloohms. In some examples, a slightly damaged sensor may be identified based on a fitted membrane resistance condition (e.g., R1 between two thresholds), and slightly damaged sensor may be approved for use or compensated (e.g., compensated based on a measure of potential damage, such as the fitted membrane resistance value, or another model parameter, or combination or parameters).

Figure 24C:
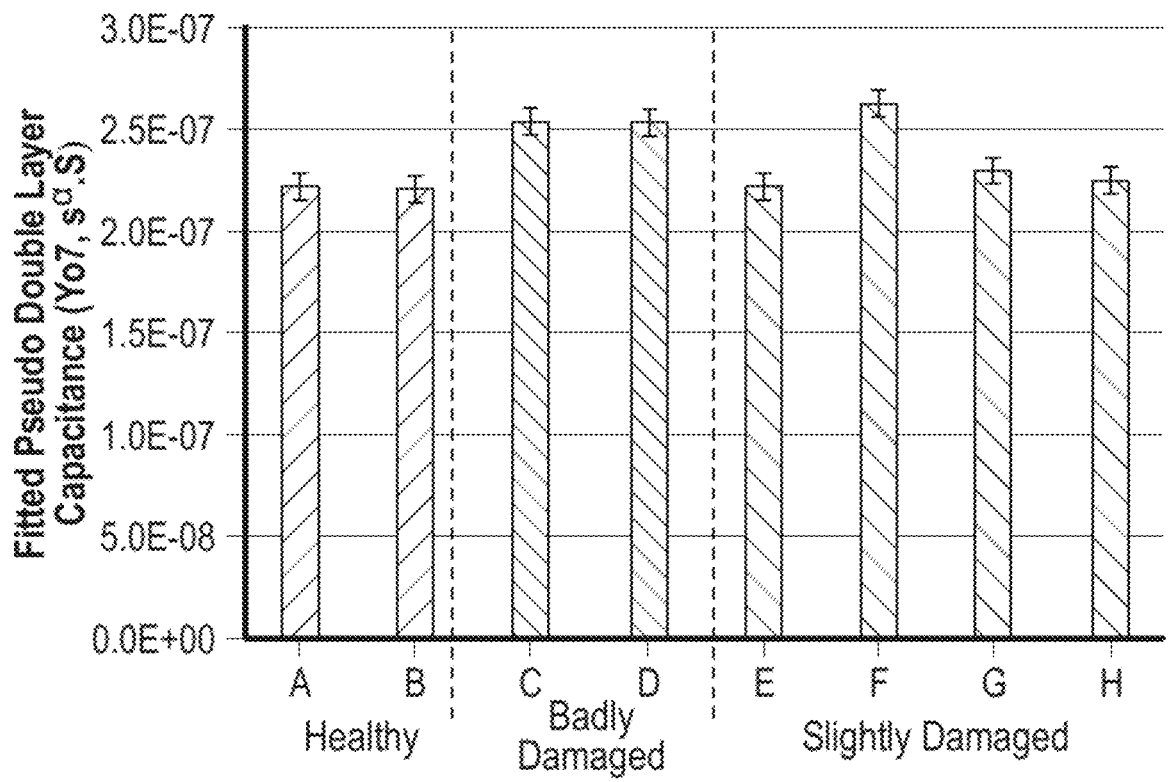
FIG. 24C is a chart that shows fitted pseudo double layer capacitance for the eight sensors.

FIG. 24C shows fitted pseudo double layer capacitance for the eight sensors. The healthy sensors (sensors A and B) have a fitted pseudo double layer capacitance that is lower than fitted pseudo double layer capacitance of the heavily damaged sensors (C and D). The slightly damaged sensors have fitted pseudo double layer capacitance values that are between the values for the healthy sensors and the values badly damaged sensors, which indicates that the fitted pseudo double layer capacitance may be used to distinguish healthy sensors from damaged sensors.

Figure 24D:
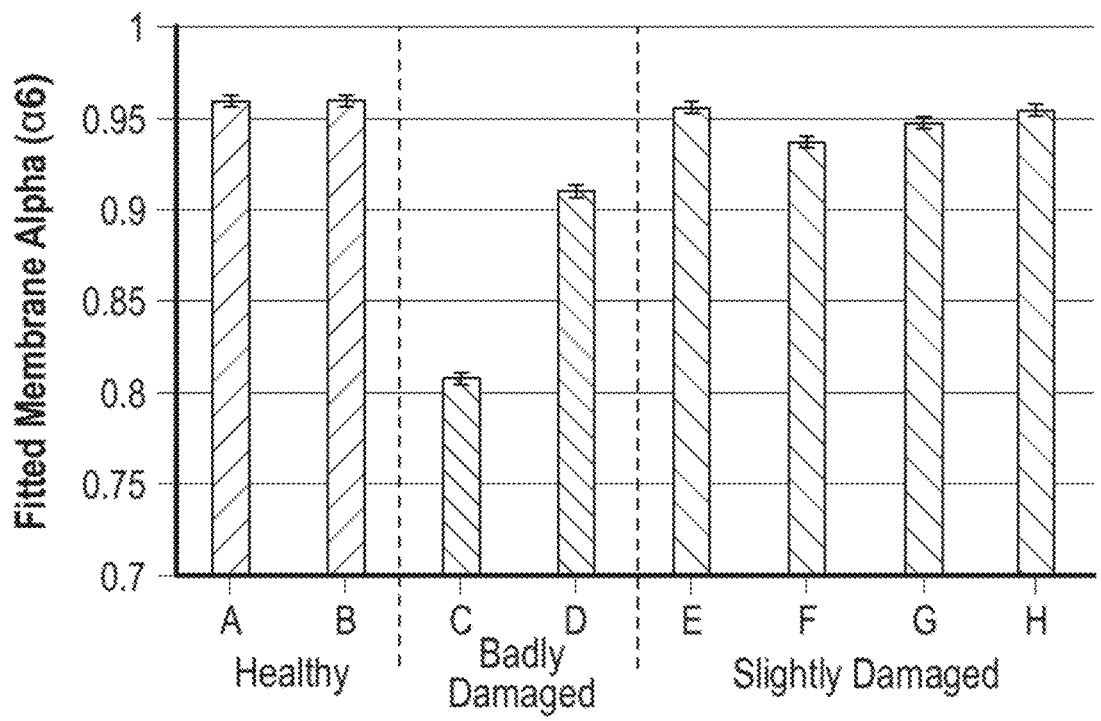
FIG. 24D is a chart that shows fitted membrane alpha for the eight sensors.

FIG. 24D shows fitted membrane alpha for the eight sensors. The healthy sensors (sensors A and B) have fitted membrane alpha values that are higher than the values for the heavily damaged sensors (C and D). The slightly damaged sensors have fitted membrane alpha values that are between values for the healthy sensors and the badly damaged sensors, which indicates that the fitted membrane alpha may be used to distinguish healthy sensors from damaged sensors.

Figure 24E:
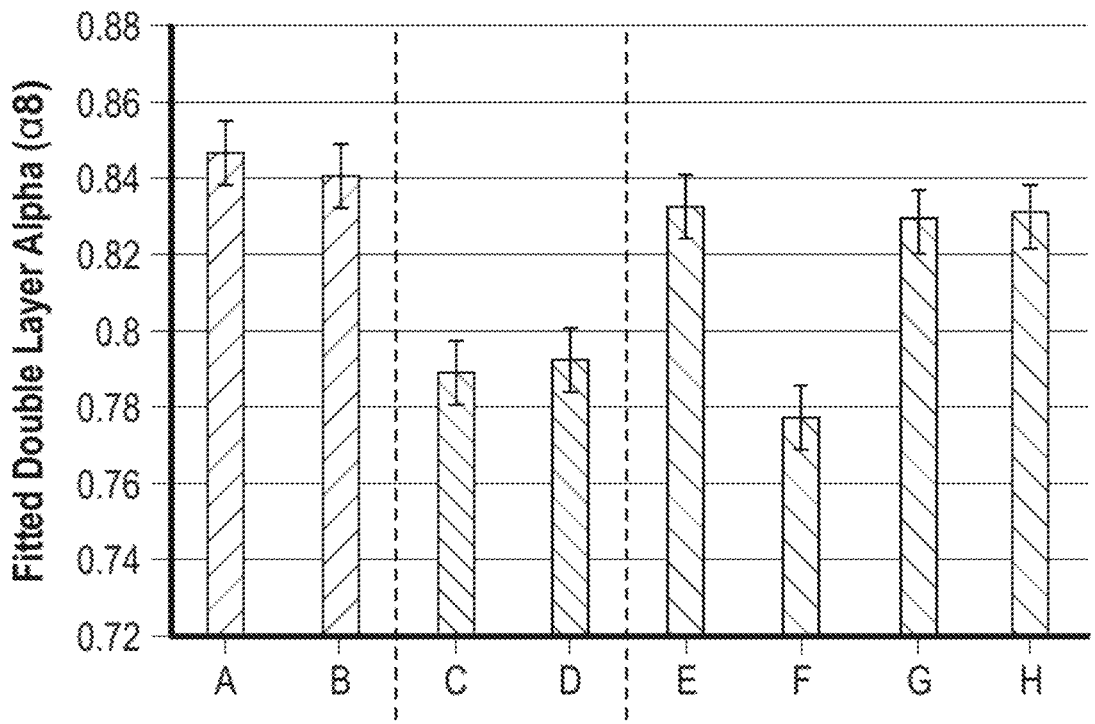
FIG. 24E is a chart that shows fitted double layer alpha for the eight sensors.

FIG. 24E shows fitted double layer alpha for the eight sensors. The healthy sensors (A and B) have fitted double layer alpha values that are significantly higher than the fitted double layer alpha values for the damaged sensors (C and D). The slightly damaged sensors have fitted double layer alpha values that are generally between the values for healthy and highly damaged sensors, with one sensor (sensor F) having a value that is lower than the highly damaged sensors.

In some examples, two or more of the parameters may be used in combination to ascertain whether a sensor is healthy, or damaged, or badly damaged. Using two or more sensors may increase the confidence in the classification of a particular sensor or reduce the likelihood of misclassification. For example, FIG. 24E suggests that sensor F is badly damaged, but the chart in FIG. 24A suggests it is slightly damaged. In some examples, the parameters may be weighted, e.g., the fitted pseudo membrane capacitance or fitted membrane resistance may be weighted more heavily than the other parameters in determining whether a sensor is damaged, or the extent of damage.

Figure 25:
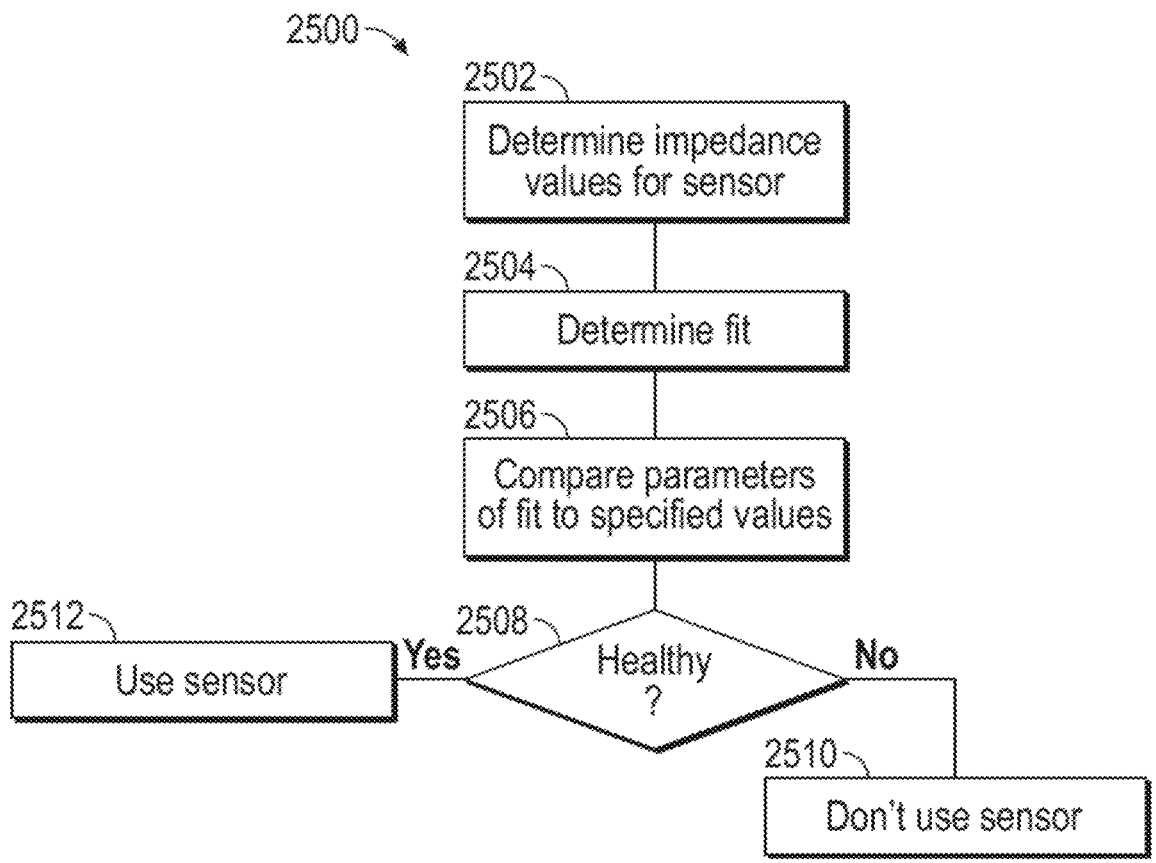
FIG. 25 is a flowchart illustration of a method of assessing a health of a sensor.

FIG. 25 is a flowchart illustration of a method 2500 of assessing a health of a sensor. At operation 2502, an impedance value is determined for a sensor. The impedance value may be determined, for example, by applying a voltage or voltage change, and measuring a current or current change, and using Ohm's law to determine impedance. In some examples, the method may include applying a plurality of signals at different frequencies and determining impedance for the different frequencies.

At operation 2504, a fit may be determined. For example, a fit may be determined for a relationship between impedance and frequency, as described in reference to FIG. 22. At operation 2506, a comparison is made to one or more specified values. For example, a comparison may be made against a reference value or a model or template. In some examples, the comparison may include a fitted parameter such as fitted pseudo membrane capacitance, fitted membrane resistance, fitted pseudo double layer capacitance, fitted membrane alpha, or fitted double layer alpha. In some examples, a comparison may be made for two or more parameters, which may increase a confidence that a sensor has been correctly characterized.

At operation 2508, a health determination may be made about the sensor. For example, the health determination may include a determination about whether the sensor is healthy, or not healthy (e.g., excessively damaged). In some examples, a sensor may be assigned a health status from three or more available classifications (e.g., healthy, slightly damaged, or extensively damaged). In some examples, a quantitative healthy assessment may be made. For example, a degree of damage of a sensor may be determined, based on one or more fit parameters.

At operation 2510, responsive to a determination that a sensor is not healthy, a sensor may be rejected. For example, a sensor may be removed from a manufacturing process (e.g., scrapped), or a user may be notified that the sensor should be replaced. At operation 2512, responsive to a determination that a sensor is healthy, it may be approved for use. In some examples, a sensor that is approved for use may be compensated based on a measured or determined parameter, such as one of the fitted parameters listed above, or based on a determined degree of damage. For example, sensor electronics may apply an adjusted sensitivity or sensitivity curve to compensate for the detected damage or abnormality characteristic in the sensor.

The method 2500 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine a health state of a sensor membrane (e.g., determine an amount of damage or abnormality) and avoid reliance on inaccurate sensor readings from an unhealthy (e.g., excessively damaged) sensor.

FIGS. 26 to 32 are flowchart illustrations that may be performed by sensor electronics (e.g., sensor electronics 106 in FIGS. 1 and 2) coupled to a sensor (e.g., sensor 104 in FIG. 1 or sensor 34 in FIGS. 3A-3B).

Figure 26:
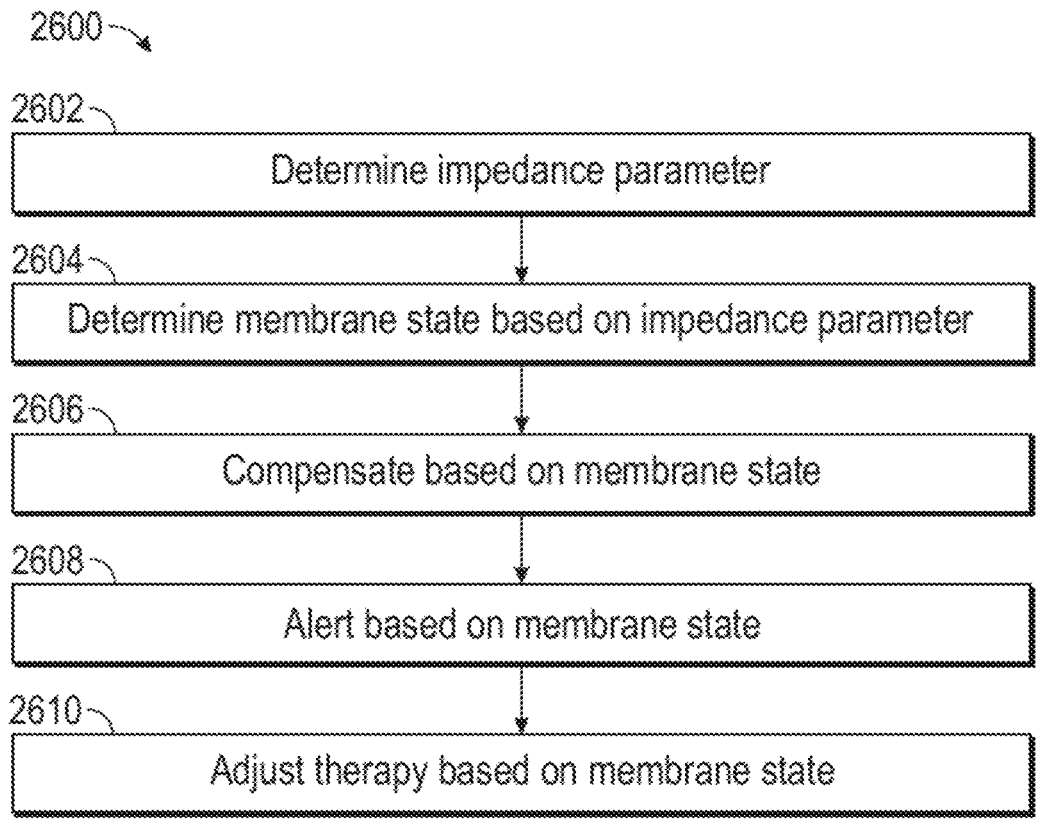
FIG. 26 is a flowchart illustration of a method of assessing sensor membrane integrity using sensor electronics.

FIG. 26 is a flowchart illustration of a method 2600 of assessing sensor membrane integrity using sensor electronics. The method may include, at operation 2602, determining an impedance parameter of an analyte sensor.

The method 2600 may include, at operation 2604, determining an integrity state of the analyte sensor membrane based on the impedance parameter. Determining the integrity state may include determining whether the membrane has damage or a significant abnormality. Determining the membrane state may include determining whether an impedance condition has been satisfied. For example, it may be determined that a sensor membrane is excessively damaged or abnormal in response to an impedance parameter that is below a specified threshold. In some examples, determining the membrane integrity state may include determining a level of membrane damage or abnormality.

In some examples, the determined impedance parameter may be an impedance of the analyte sensor after hydration, or a determined impedance of a membrane portion of an analyte sensor after hydration, e.g., using methods described above. The method may include determining the impedance parameter based on a measurement a specified time after hydration of the sensor. In some examples, the specified time may between 5 and 600 seconds after hydration. Hydration may include, for example, insertion of a sensor in a bath, or insertion of a sensor in a host. In some examples, the impedance parameter may be determined based on a measurement after a measured parameter has reached a steady state condition (e.g., responsive to detecting that impedance has stabilized, which may correlate with a time that the membrane has become sufficiently hydrated or other processes at the working electrode or an insertion site have sufficiently progressed).

In some examples, the impedance parameter may be a derivative (e.g., first derivative or second derivative) of impedance with respect to time. The membrane integrity state may be determined, for example, based on a shape of a first derivative vs. time curve or second derivative vs. time curve, or basted on one or more values of a first derivative or a second derivative.

In some examples, the membrane integrity state may be determined based at least in part on a fitted membrane resistance determined using a constant phase element model. In various examples, determining a membrane integrity state may include performing a template match, determining a best fit from a plurality of templates, or using dynamic time warping, or any combination thereof.

In some examples, the impedance parameter may be determined at a specified frequency. For example, the impedance parameter may be determined at a frequency above 50 Hz. In some examples, the impedance parameter may be determined at a frequency between 50 Hz and 3,000 Hz. In some examples, the comparison between the impedance at the frequency and the impedance at the second frequency is a difference between the impedance at the first frequency and the impedance at the second frequency. As described above, the difference in frequency is referred to as the "dual frequency impedance." The first frequency and second frequency may provide a relatively pronounced impedance difference. For example, the frequencies may be specified to accentuate the impedance difference, e.g., provide a relatively large difference, compared to selection of other adjacent frequencies. In some examples, the comparison includes determining an existence or amount of a kickback in a dual frequency impedance vs. time relationship, e.g., kickback may be detected when a dual frequency impedance reaches a low point and then rises to a generally steady value that is larger than the low point.

In some examples, the determined impedance parameter may be based on a comparison (e.g., a difference) of an impedance at a first frequency and an impedance at a second frequency. The comparison between an impedance at the first frequency and the impedance at the second frequency may become stable at a time after hydration that is earlier than the impedance at the first frequency or the impedance at the second frequency (or both) becomes stable, which may allow for an earlier assessment of the state of the membrane. For example, a damaged membrane may be more quickly identified after insertion into a host, which may allow for earlier notification of a user that the sensor should be replaced.

The method 2600 may include, at operation 2606, compensating an estimated analyte concentration level based at least in part on a determined level of membrane damage or abnormality. For example, an estimated analyte concentration level may be compensated by adjusting a sensitivity value based on the determined level of membrane damage or abnormality as indicated by an impedance parameter. The method 2600 may include, at operation 2608, alerting a user based on a membrane state. For example, a system may declare an alert or raise a "replace sensor" alarm" responsive to a membrane state that suggests a problem (e.g., damage) with a membrane.

The method 2600 may also include, at operation 2610, changing a therapy responsive to a determined membrane state. For example, a system may generate a recommended insulin dosage that is changed (e.g., reduced) based on the membrane state, or an insulin pump may change an insulin dosing regimen or scheme based on the membrane state.

The method 2600 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine a state of a sensor membrane (e.g., determine an amount of damage or abnormality) and avoid reliance on inaccurate sensor readings from an excessively damaged sensor, or determine an estimated analyte concentration level more accurately than conventional methods based on knowledge of the membrane state.

Figure 27:
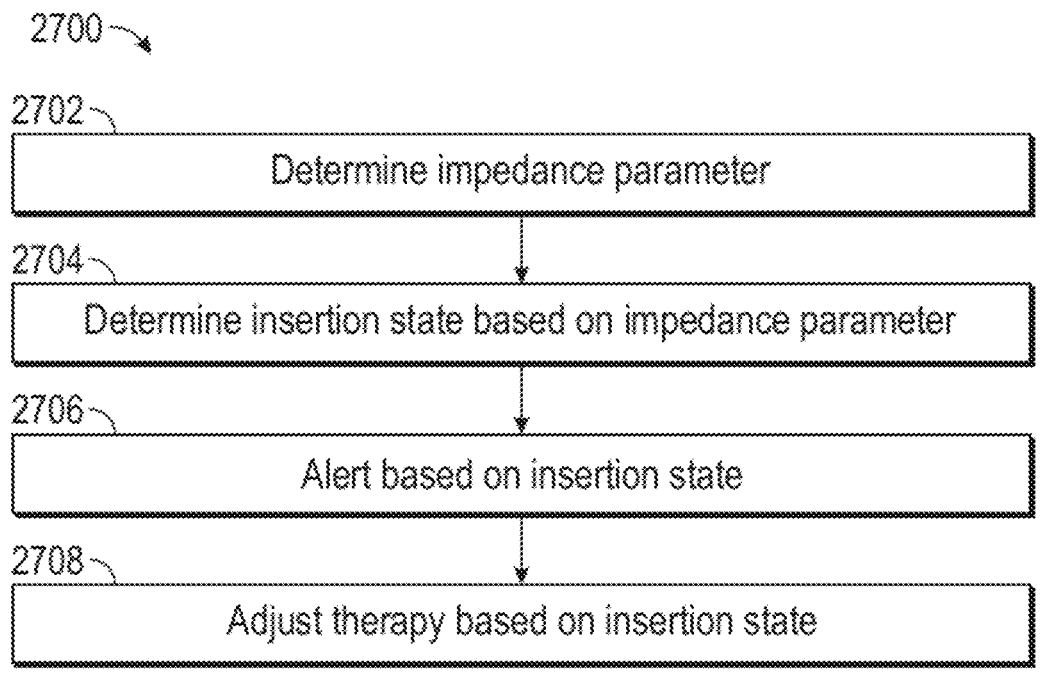
FIG. 27 is a flowchart illustration of a method of operating analyte sensor that may include determining an impedance parameter of an analyte sensor.

FIG. 27 is a flowchart illustration of a method 2700 of operating analyte sensor that may include, at operation 2702, determining an impedance parameter of an analyte sensor. In some examples, the impedance parameter may be a sensor impedance or membrane impedance, which may be determined using any of the methods described herein (e.g., using a measured current, a known voltage applied by sensors electronics, and Ohm's law).

The method 2700 may include, at operation 2704, determining an insertion state of the analyte sensor based on the impedance parameter. In some examples, determining an insertion state may include detecting a dislodgment of a sensor from an insertion position in a host. In some examples, determining the insertion state may include detecting that a sensor has been at least partially pulled out of an initial insertion position. Dislodgment may be detected, for example, based upon an increase in impedance.

The method 2700 may include, at operation 2706, alerting a user based on an insertion state (e.g., delivering a message on a receiver or smart device such as "Sensor has dislodged").

The method 2700 may include, at operation 2708, altering a therapy responsive to a determined membrane state. For example, a system may generate a recommended insulin dosage that is changed (e.g., reduced) based on the membrane state, or an insulin pump may change an insulin dosing regimen or scheme based on the membrane state (e.g., the pump may not rely on sensor data, or rely on sensor data from prior to a sensor withdrawal event).

The method 2700 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an insertion state of a sensor and avoid reliance on inaccurate sensor readings from a dislodged sensor or determine an estimated analyte concentration level more accurately than conventional methods based on knowledge of the insertion state.

Figure 28:
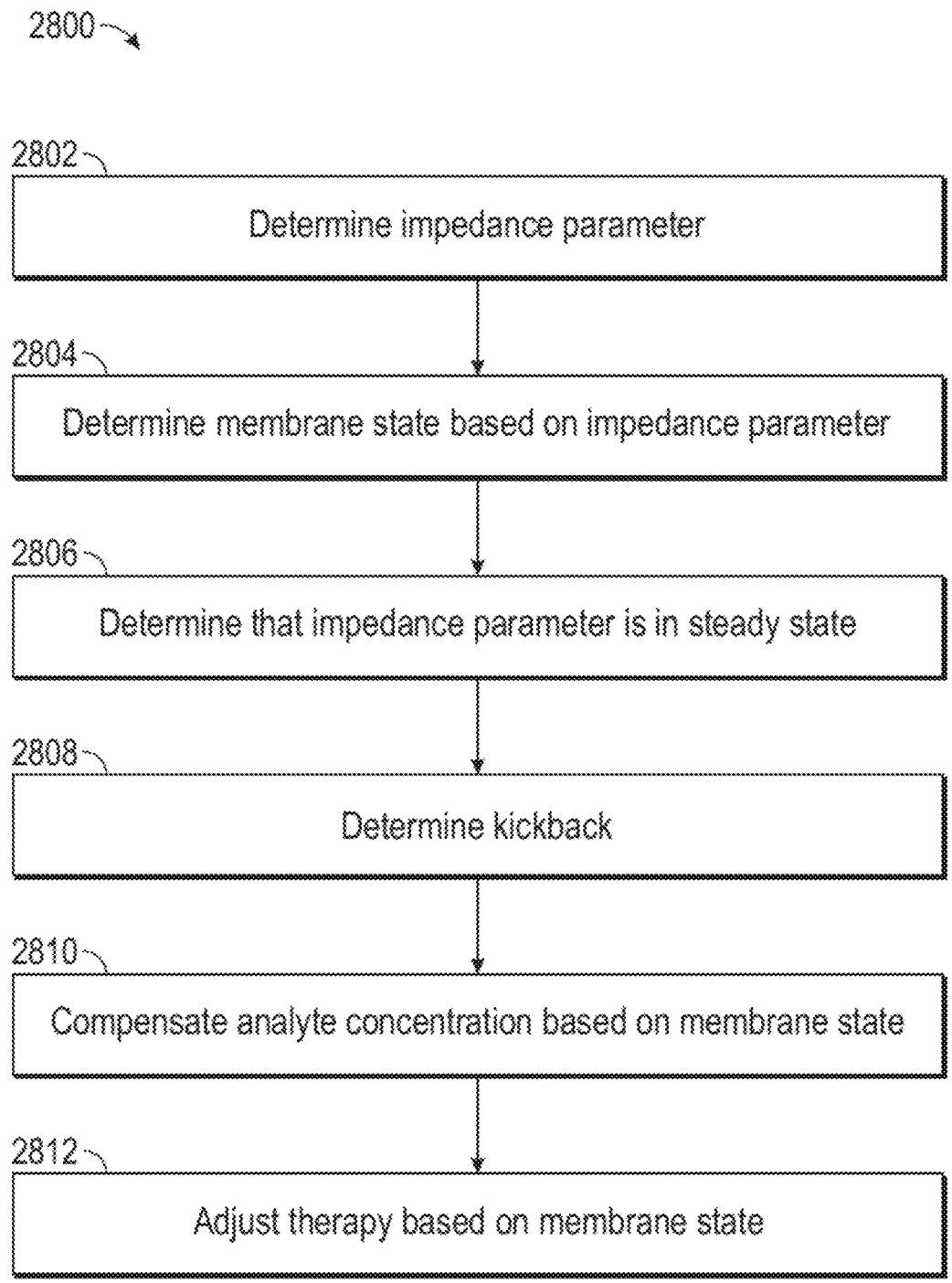
FIG. 28 is a flow chart illustration of a method of compensating an analyte sensor system that may be executed by sensor electronics.

FIG. 28 is a flow chart illustration of a method 2800 of compensating an analyte sensor system that may be executed by sensor electronics. The method 2800 may include, at operation 2802, determining an impedance parameter of an analyte sensor. In various examples, the impedance parameter may be an estimated membrane impedance, an impedance at a specified frequency, a dual frequency impedance, a first derivative of impedance with respect to time, or a second derivative of impedance with respect to time.

The method 2800 may include, at operation 2804, determining a membrane state based on the impedance parameter. For example, sensor electronics may determine the impedance parameter, and apply logic, compare the impedance parameter to a threshold or condition, or one or more impedance parameters to a model to determine a membrane state.

The method 2800 may include, at operation 2806, determining that the impedance parameter is in a steady state. For example, sensor electronics may compare a plurality of sequential impedance parameter values or perform statistical analysis or other analysis to assess a stability of the impedance parameter.

The method 2800 may include, at operation 2808, determining an existence or amount of a kickback in a dual frequency impedance vs. time relationship.

The method 2800 may include, at operation 2810, compensating an analyte concentration level based on the membrane state. For example, sensor electronics may use the membrane state or the steady state impedance parameter to compensate a sensor sensitivity, e.g., to account for drift or sensor-to-sensor variations in impedance. In some examples, sensor electronics may determine an amount of compensation based on the existence or amount of kickback.

The method 2800 may include, at operation 2812, adjusting a therapy based on the determined membrane state. For example, a system may generate a recommended insulin dosage that is changed (e.g., reduced) based on the membrane state, or an insulin pump may change an insulin dosing regimen or scheme based on the membrane state.

In some examples, a system may declare an alert or raise a "replace sensor" alarm" responsive to determination of a membrane state. For example, the system may raise an alert responsive to determination that a sensor is damaged.

The method 2800 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an estimated analyte concentration level more accurately than conventional methods.

Figure 29:
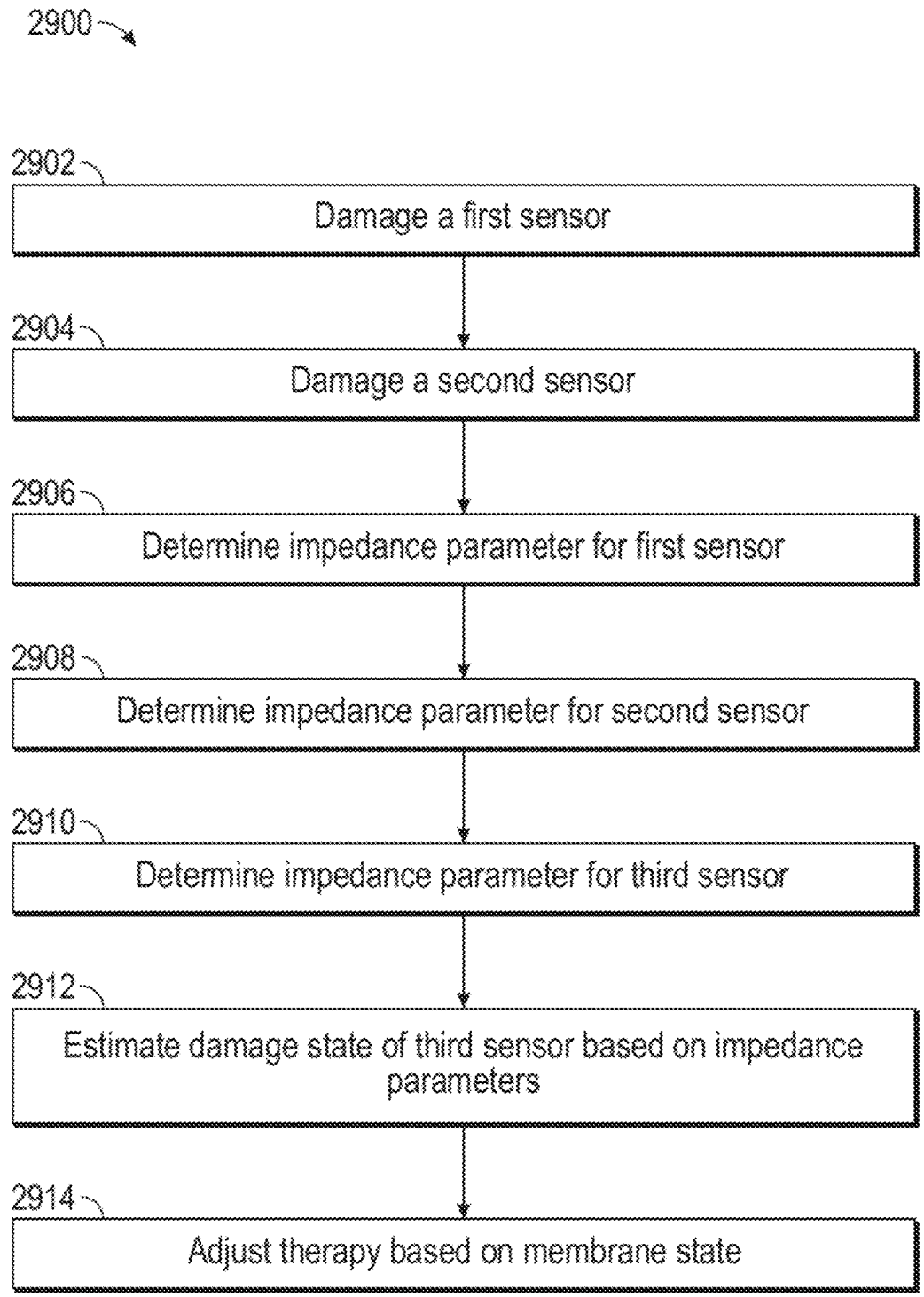
FIG. 29 is a flow chart illustration of a method of calibrating damage to impedance in a population of analyte sensors.

FIG. 29 is a flow chart illustration of a method 2900 of calibrating damage to impedance in a population of analyte sensors. The method 2900 may include, at operation 2902, damaging a first sensor; and at operation 2904, damaging a second sensor. The method 2900 may further include, at operation 2906, determining an impedance parameter for the first sensor using a first process, and, at operation 2908, determining an impedance parameter for the second sensor using a second process, wherein the second process is different than the first process. In an example, damaging the first sensor includes scratching the first sensor against an abrasive surface a specified number of times, and damaging the second sensor includes scratching the second sensor against an abrasive surface a specified number of times. For example, a first sensor may be scratched three times, and a second sensor may be scratched eight times, and it may be inferred from the process that the second sensor is more damaged that the first sensor.

The method 2900 may further include, at operation 2910, determining an impedance parameter for a third sensor. The method 2900 may further include, at operation 2912, estimating a damage state of the third sensor based at least in part on the determined impedance parameter for the first sensor, the determined impedance parameter for the second sensor, and the determined impedance parameter for the third sensor. In some examples, the method 2900 may include determining a damage curve based at least in part on the determined impedance parameter for the first sensor and the determined impedance parameter for the second sensor and estimating the damage state of the third sensor based upon the determined impedance parameter for the third sensor and the damage curve. In some examples, each of a plurality of sensors (e.g., five, ten, or twenty sensors) may be scratched a different number of times to provide a continuum of degrees of damage for comparison against a characteristic of a sensor of interest (e.g., the third sensor). At operation 2914, a therapy may be adjusted based on a membrane state. For example, delivery of insulin may be adjusted based on a membrane state, which may for example be received from an analyte sensor system via a wired or wireless communication connection.

The method 2900 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., by estimating a damage state the damage state to identify excessively damaged sensors, or determine an accurate estimated analyte concentration level more accurately than conventional methods.

Figure 30:
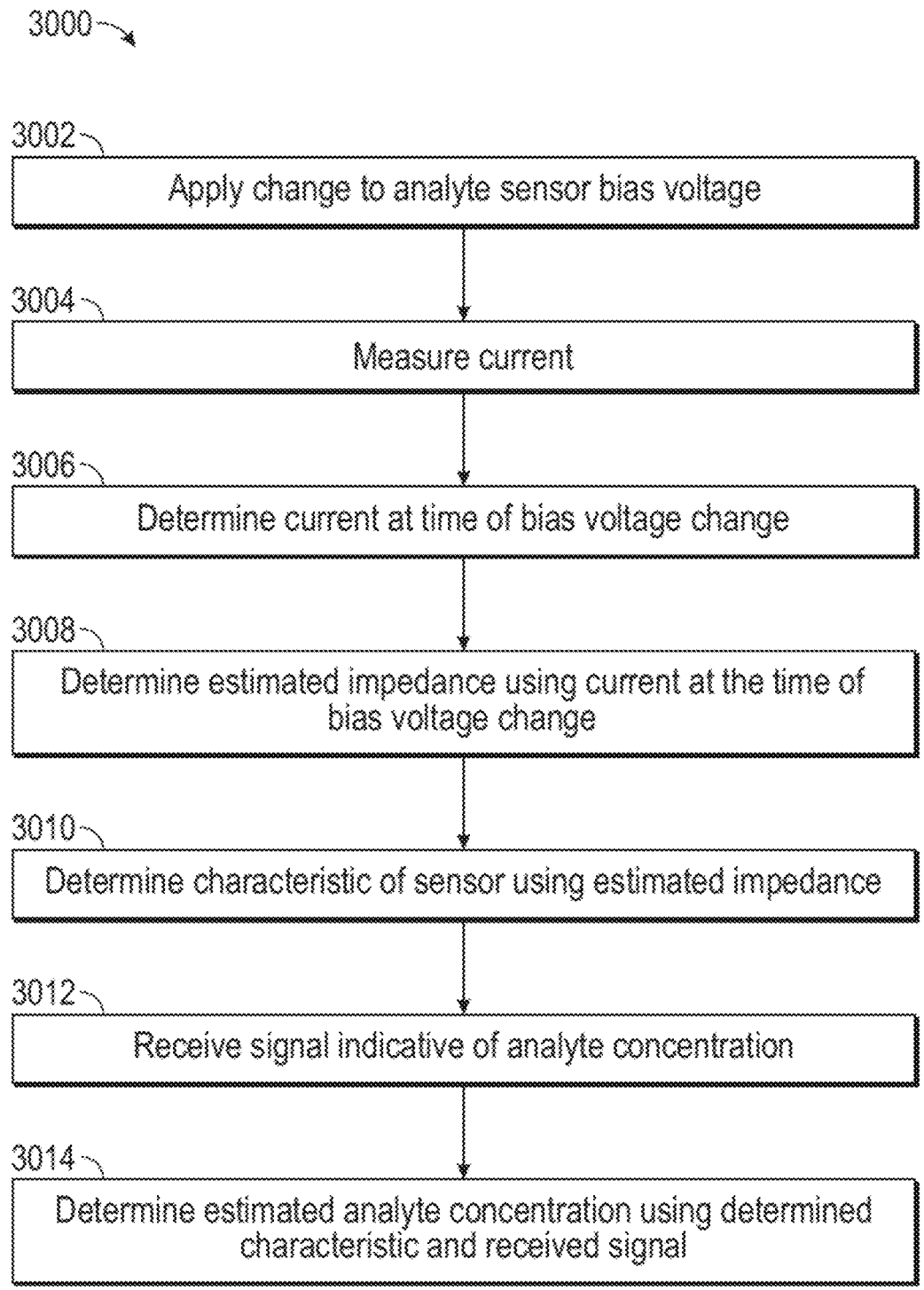
FIG. 30 is a flow chart illustration of a method of operating an analyte sensor system using sensor electronics to correct for an error from double-layer capacitance of a sensor membrane.

FIG. 30 is a flow chart illustration of a method 3000 of operating an analyte sensor system using sensor electronics to correct for an error from double-layer capacitance of a sensor membrane. The method 3000 may include, at operation 3002, applying a change to an analyte sensor bias voltage, for example as described in reference to FIGS. 5A to 5C.

The method 3000 may include, at operation 3004, measuring a current value for each of a plurality of time periods after application of the bias voltage change. The method 3000 may include, at operation 3006, determining a current at the time of the bias voltage change using the current values for the plurality of time periods. For example, a curve may be extrapolated using current values measured after the bias voltage change to determine a current at the time of the bias voltage change, which may allow for more accurate determination of an impedance, by accounting for a membrane capacitance, as described in reference to FIGS. 8A to 8D. In some examples, the method 3000 may include fitting the current values for the plurality of time periods to an exponential curve and extrapolating the fitted curve to determine the current at the time of the bias voltage change, for example as described in reference to FIGS. 8C and 8D.

The method 3000 may include, at operation 3008, determining an estimated impedance using the determined current at the time of the bias voltage change. The method 3000 may include, at operation 3010, determining a characteristic of the analyte sensor using the estimated impedance. In some examples, determining the characteristic of the analyte sensor may include determining a sensor sensitivity. In some examples, a sensor sensitivity may be updated to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

The method 3000 may include, at operation 3012, receiving from the analyte sensor a signal indicative of an analyte concentration. The method 3000 may include, at operation 3014, determining an estimated analyte concentration level using the determined characteristic of the analyte sensor and the received signal.

The method 3000 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an impedance of or characteristic of a sensor more accurately than conventional methods, which may allow for more accurate determination of estimated analyte concentration methods.

Figure 31:
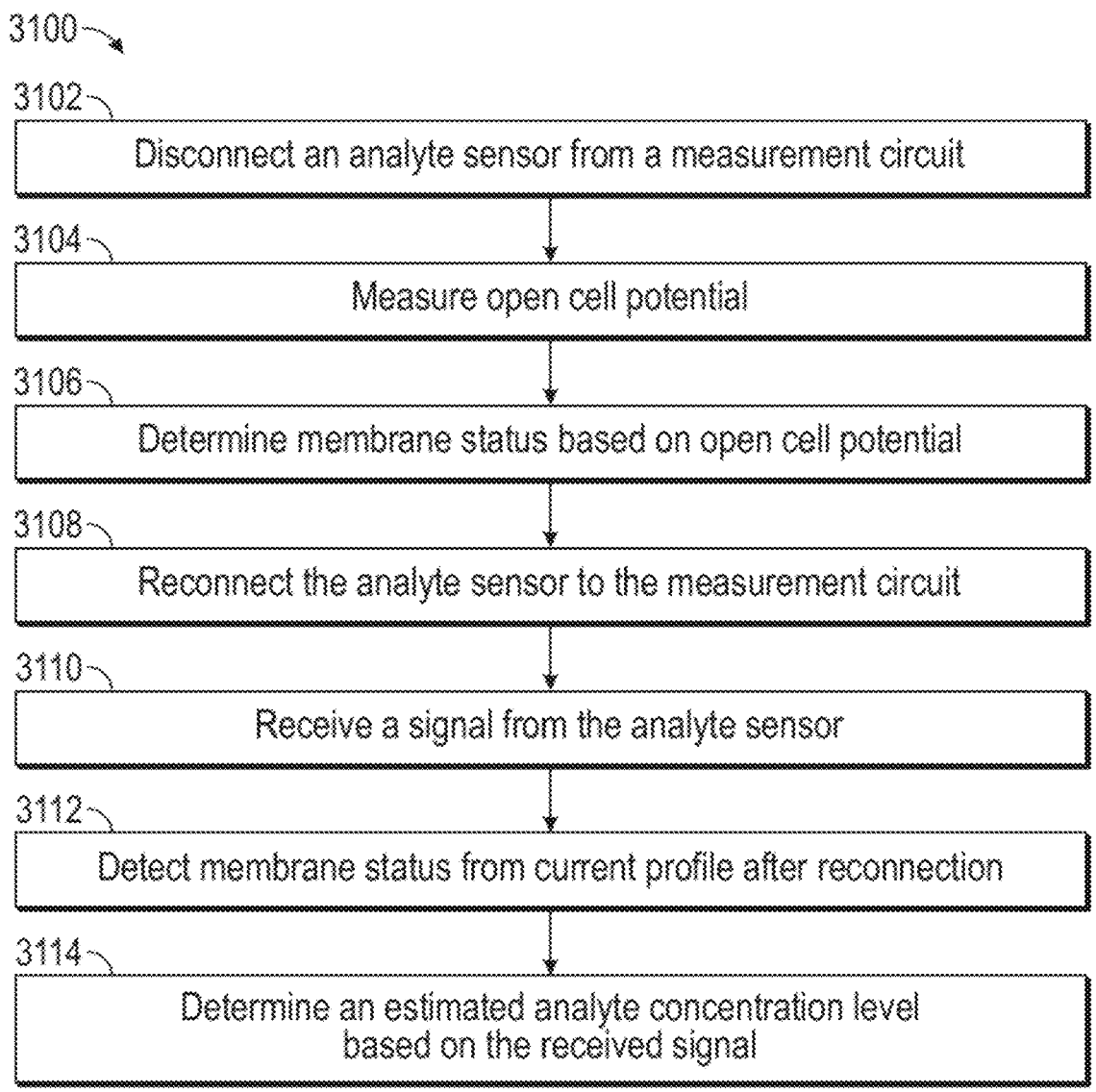
FIG. 31 is a flowchart illustration of a method that may include disconnecting an analyte sensor from a measurement circuit.

FIG. 31 is a flowchart illustration of a method 3100 that may include, at operation 3102, disconnecting an analyte sensor from a measurement circuit.

The method 3100 may include, at operation 3104, measuring one or more open cell potentials during the accumulation period. The method 3100 may include, at operation 3106, determining a membrane status based on one or more open cell potentials. In various examples, the membrane status may include an interference status (e.g., interference from acetaminophen), or a damage or abnormality status. For example, an abnormality or damage in a sensor membrane may be detected based upon an impedance characteristic (e.g., estimated sensor impedance, estimated membrane impedance, a first derivative of impedance, a second derivative impedance, or a fitted curve) determined from the one or more open cell potentials, or from a shape of an open cell vs. time curve.

The method 3100 may include, at operation 3108, reconnecting the analyte sensor to the measurement circuit after an accumulation period. The method 3100 may include using a gate circuit to disconnect and reconnect the analyte sensor.

The method 3100 may include, at operation 3110, receiving a signal from the analyte sensor, wherein the signal is indicative of an amount of charge accumulated on the analyte sensor during the accumulation period. Disconnecting and reconnecting (e.g., gating) an analyte sensor may improve the performance of a sensor system, for example because charge from an analyte reaction may increase during an accumulation period, resulting in a larger detectable current signal, whereas sources of interference or noise (e.g., acetaminophen) may not grow during the accumulation period. In some examples, the disconnection and reconnection of the analyte sensor improves a signal to interference ratio of the analyte sensor, as described above in the section titled "Gated Amperometric Detection."

The method 3100 may include, at operation 3112, determining a membrane status based on the analyte signal received after reconnection of the analyte sensor to the measurement circuit. In some examples, the method 3100 may include monitoring a current profile after reconnecting the analyte sensor and detecting a membrane status (e.g., membrane fault) using the current profile. In some examples, the method 3100 may include determining an impedance characteristic and detecting a membrane fault responsive to the impedance characteristic satisfying a fault condition (e.g., impedance characteristic below a threshold or resembling a damage template curve). In various examples, the impedance characteristic may be an estimated membrane impedance, a first derivative of impedance, a second derivative impedance, or a fitted curve.

The method 3100 may include, at operation 3114, determining an estimated analyte concentration level based on the received signal.

The method 3100 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to improve the signal to noise ration of a sensor system, or avoid reliance on inaccurate sensor readings from a sensor that has a damaged or abnormal membrane, or to determine an estimated analyte concentration level more accurately than conventional methods, based on one or more of the factors mentioned above.

Figure 32:
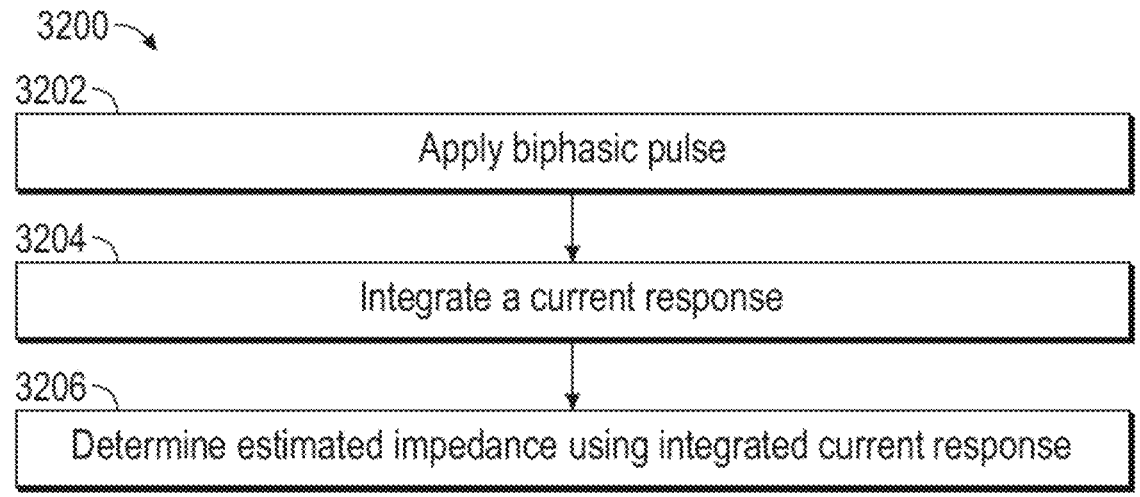
FIG. 32 is a flowchart illustration of a method that may include applying a biphasic pulse to a continuous analyte sensor circuit.

FIG. 32 is a flowchart illustration of a method 3200 that may include, at operation 3202, applying a biphasic pulse to a continuous analyte sensor circuit. The method 3200 may include, at operation 3204, integrating a current response to the biphasic pulse, e.g., as described in reference to FIG. 9. The method 3200 may include, at operation 3206, determining an estimated impedance using the integrated current response, for example as shown in FIG. 9 and described in reference thereto. As described in various examples above, the estimated impedance may be used to detect a sensor membrane status or compensate for drift.

The method 3200 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an impedance, detect a sensor membrane status (e.g., membrane fault), or determine an estimated analyte concentration level more accurately than conventional methods.

In some examples, the method 3100 or method 3200 may include compensating a sensor sensitivity using the determined impedance. In some examples, the method may include determining impedance using a signal at a frequency that avoid an effect of a double-layer membrane capacitance on the impedance. In some examples, the compensation may be based on impedance and one or more additional factors, such as temperature, a calibration curve (e.g., factory-determined calibration curve), or any combination thereof. In some examples, the compensation may use a transmitter temperature, and the transmitter temperature may be filtered using Greene's function.

In various examples, the method 3100 or 3200 may include determining the humidity of an environment of the sensor based at least in part on a determined impedance. For example, the method may include detection of humidity during transportation of the sensor or during storage of the sensor, or both. In some examples, the performance or operation of a sensor may be affected the humidity environment. In some examples, the method 3100 or method 3200 may include compensating a sensor sensitivity based upon the determined humidity and may optionally include declaring an alert based upon a determined humidity. For example, the method 3100 or 3200 may include delivering an alert using a smart device to alert a user that a sensor should not be used due to excessive humidity exposure.

Experiments were run to demonstrate the effectiveness of these approaches and the potential for improving the performance of an analyte sensor system. Based on forty-one (41) preliminary datasets, a Monte Carlo cross-validation procedure was performed on a commercially-available system (as a baseline) and four different techniques (described below) for improving the performance of an analyte sensor system. The results of the experiments are shown in FIGS. 33A-33F and show that the prediction errors of in vivo glucose sensitivity can be significantly improved using the combination of different physical measurements, such as impedance, temperature, and a calibration curve.

For a baseline comparison, a standard commercial factory-calibrated Dexcom G6 sensor system was used, without in vivo calibration.

A first technique based sensitivity drift compensation on impedance measurement alone using the relationship (IMPD) described above.

A second technique based sensitivity drift compensation on both impedance and calibration curve using the relationship (IMPD+CC) described above.

A third technique based sensitivity drift compensation on both impedance and temperature using the relationship (IMPD+T) described above.

A fourth technique based sensitivity drift compensation on impedance, temperature and a calibration curve, using the relationship (IMPD+CC+T) described above.

For the purpose of comparison, curves were also generated for a factory calibration approach with wedge parameters optimized locally using the same informal datasets as those used in training the other prototype algorithms ("FC Local").

FIGS. 33A to 33F show the cumulative distribution functions (CDF), for various metrics, from 1000 rounds of randomizations.

Figure 33A:
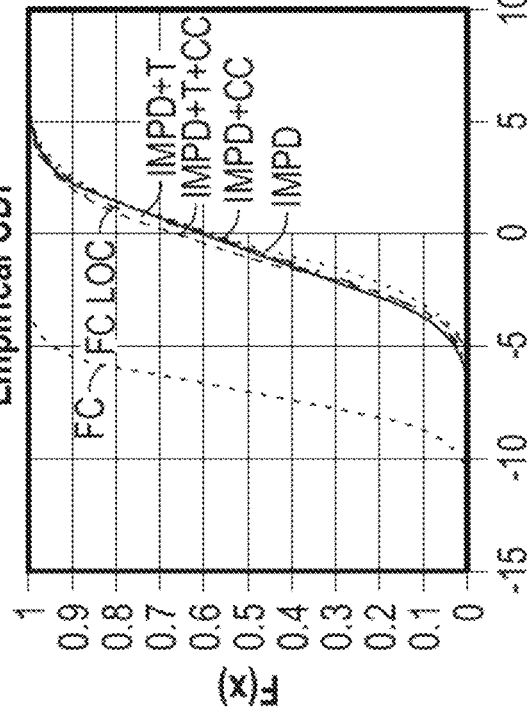
FIG. 33A shows empirical cumulative distribution function of the mean absolute relative difference (MARD) for a variety of compensation techniques.

FIG. 33A shows empirical cumulative distribution function of the mean absolute relative difference (MARD). The MARD is a measure of error. Thus, with respect to sensor system performance, a lower MARD is more desirable than a higher MARD, because the sensor data will be more accurate (e.g., include less error compared to a gold standard). The F(x) on the Y axis is the proportion of randomizations that produced a particular MARD.

Each of the drift compensation techniques provided a lower MARD than the baseline factory-calibrated (FC) sensor. The technique that used impedance, a calibration curve (CalCheck), and temperature produced the smallest MARD.

Figure 33B:
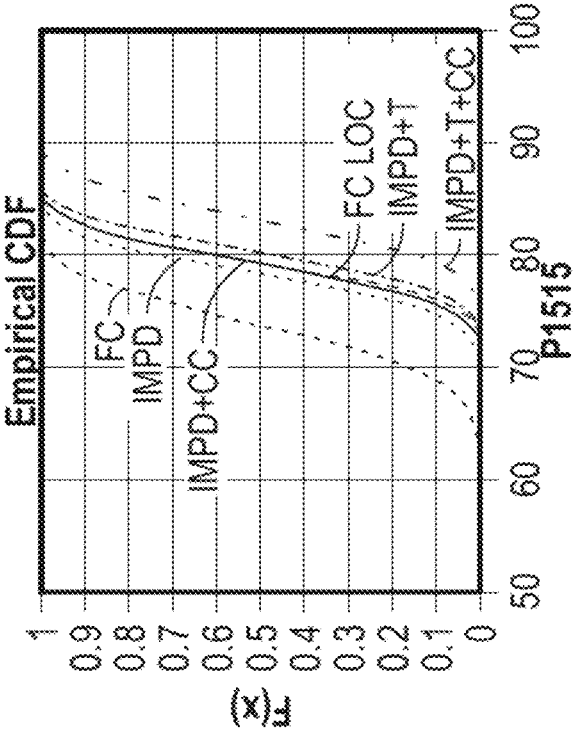
FIG. 33B shows the empirical cumulative distribution function of the mean relative difference (MRD).

FIG. 33B shows the empirical cumulative distribution function or the mean relative difference (MRD). An MRD value closer to zero is more desirable. The various improvement techniques produced highly clustered MRD values, and each technique represents an improvement over the factory-calibrated (FC) result.

Figure 33C:
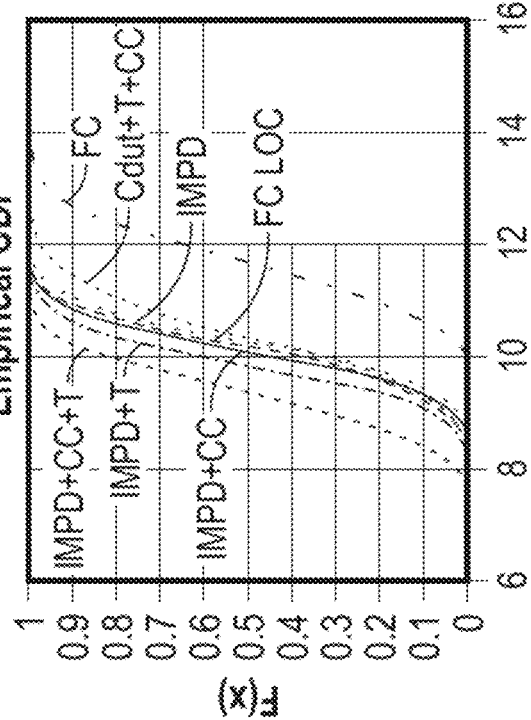
FIG. 33C shows the empirical cumulative distribution function of the relative distance (RD).

FIG. 33C shows the empirical cumulative distribution function or the relative distance (RD). An RD value closer to zero is more desirable. The various improvement techniques produced highly clustered MRD values, and each technique represents an improvement over the factory-calibrated (FC) result.

Figure 33D:
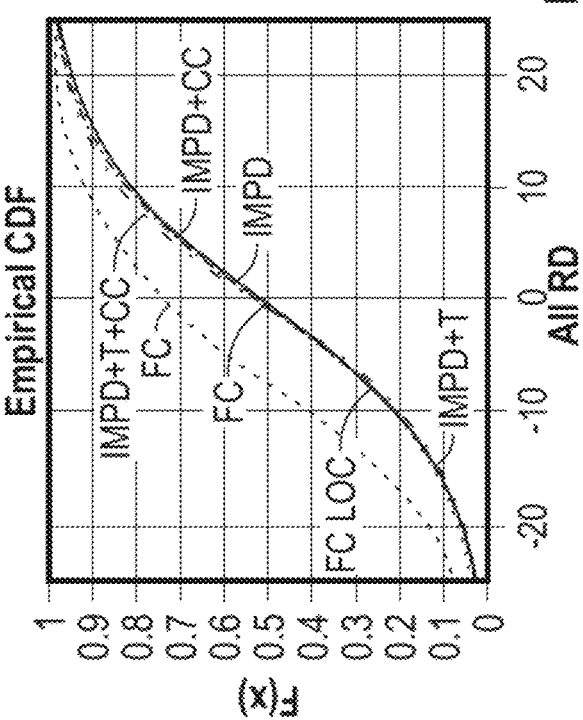
FIGS. 33D, 33E, and 33F show the empirical cumulative distribution function for p1515, p2020, and p4040.
Figure 33E:
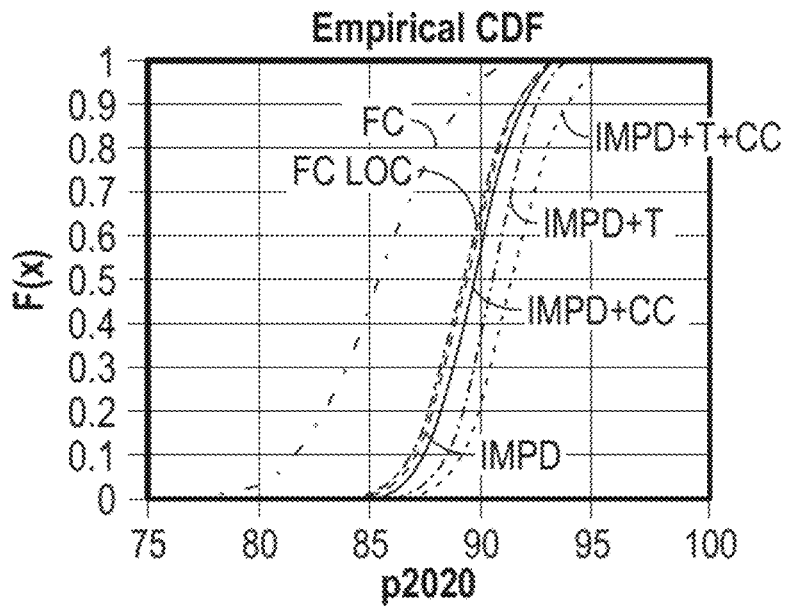
Figure 33F:
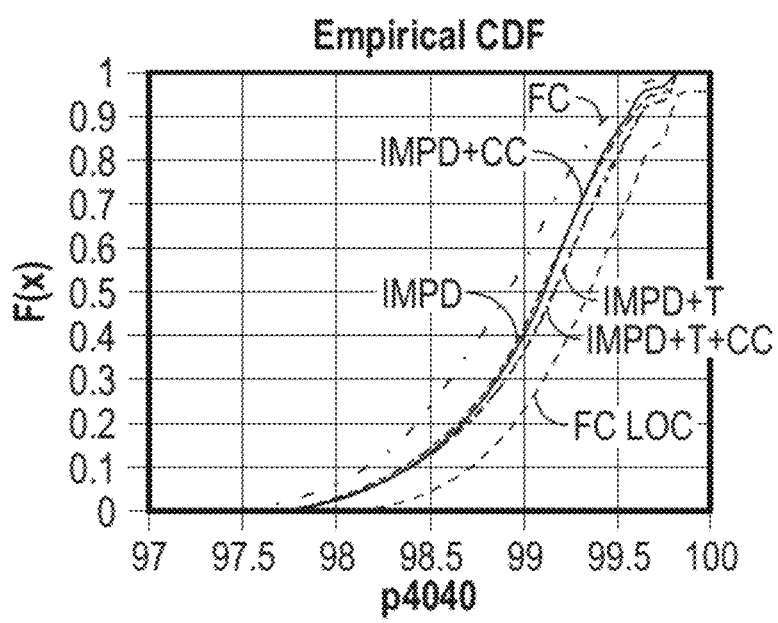

FIGS. 33D, 33E, and 33F show the empirical cumulative distribution function for p1515, p2020, and p4040. The charts indicate the percentage of randomizations that will fall within respective fifteen percent (±15% for FIG. 33D), twenty percent (±20% for FIG. 33E), or forty percent (±15% for FIG. 33F), of an actual blood glucose value. A higher value is better, as it indicates that a larger percentage of sensors will fall within a specified error range. Each of the four techniques improved the performance of the analyte sensor system.

Using a compensation technique to account for factors such as temperature, in vivo environment changes, and damage may improve sensor performance (e.g., lower the MARD for a sensor or a sensor population), or may improve manufacturing yields (e.g., a smaller percentage of sensors may fail a performance test), or both.

Figure 34:
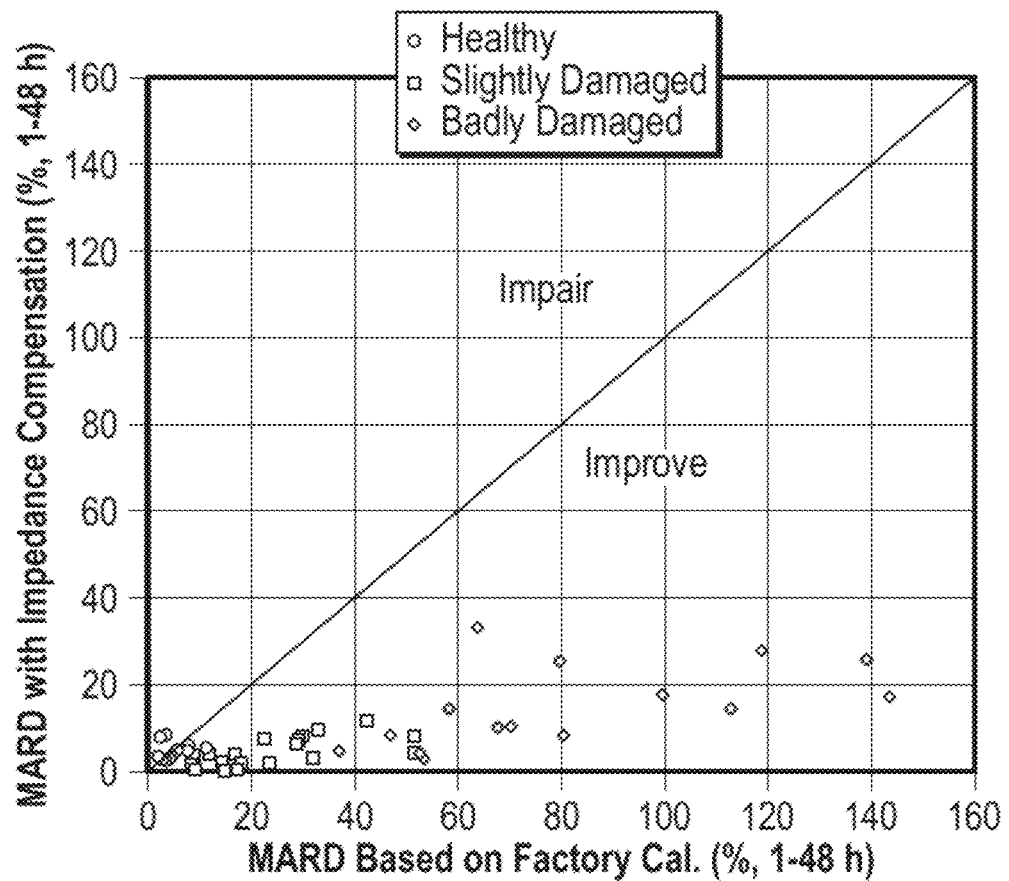
FIG. 34 is a plot showing example results of the experiment indicating a MARD with impedance compensation versus a MARD based on factory calibration.
Figure 35:
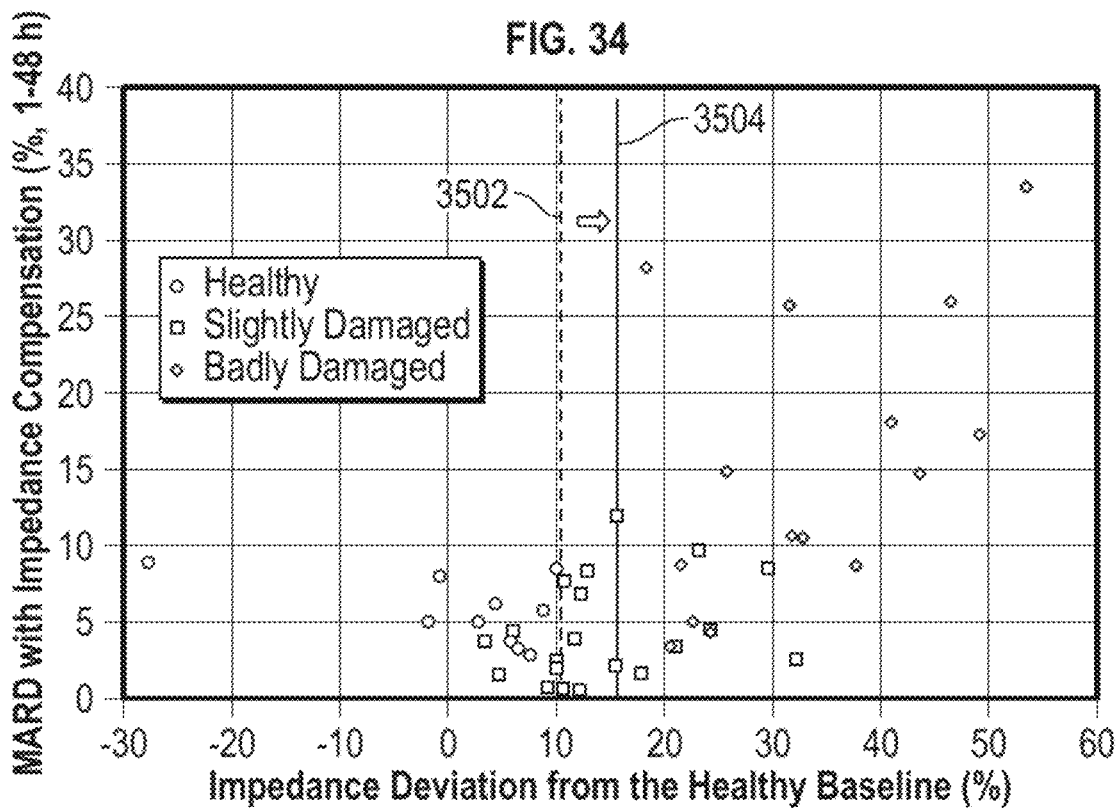
FIG. 35 is a plot showing example results of an experiment indicating sensor MARD with impedance compensation versus impedance deviation from a healthy baseline.
Figure 36:
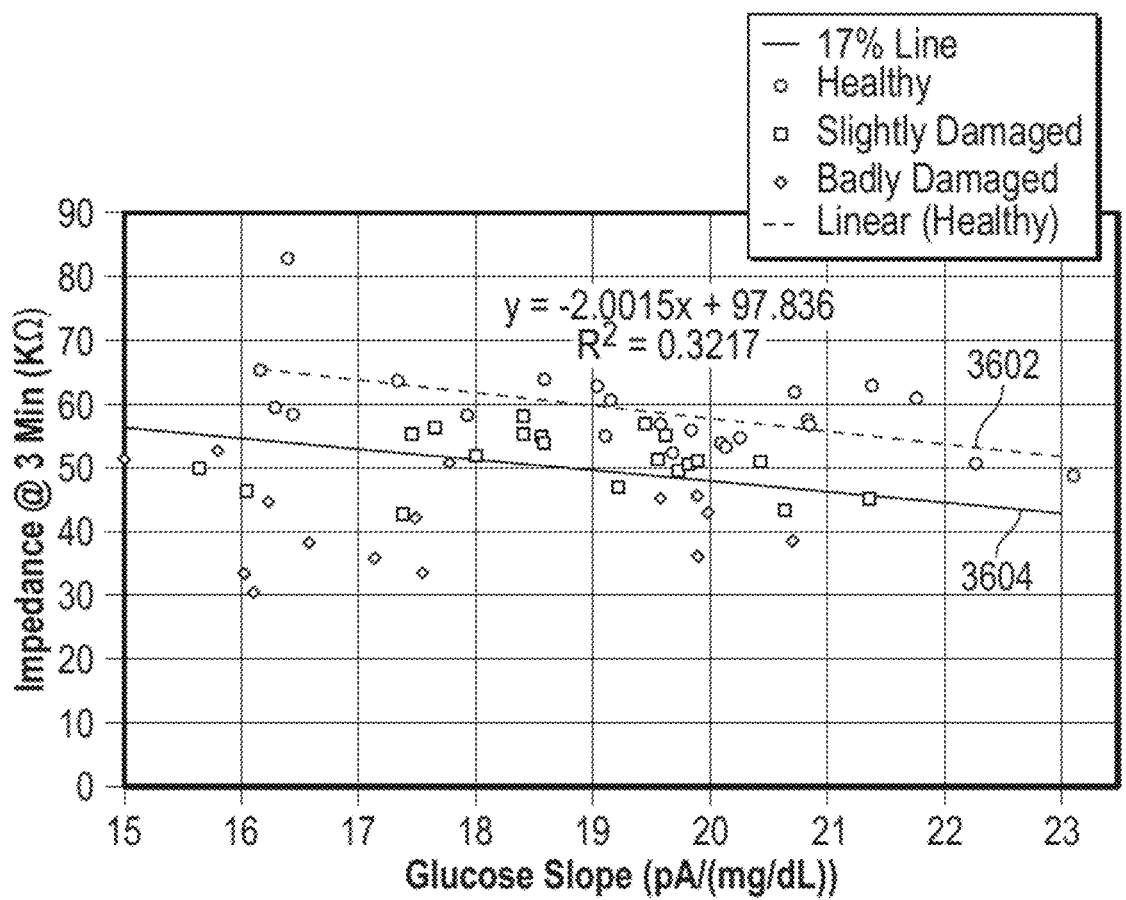
FIG. 36 is an example plot of the experiment described herein showing sensor impedance at three minutes from insertion versus glucose slope.

FIGS. 34-36 show results of additional experiments that were run to demonstrate the effectiveness of using impedance compensation to compensate for damaged sensors. Dexcom G6 sensor systems were used, both with and without impedance compensation. When used without impedance compensation, a standard commercial factory calibration was used. When used with impedance compensation, the impedance compensation was determined using the technique described herein with respect to FIGS. 30A-30G, although it is believed that similar results can be achieved with any suitable impedance compensation technique.

The experiments described by FIGS. 34-36 were run with a set of sensors that were healthy, a set of sensors that were slightly damaged, and a set of sensors that were badly damaged. Referring to the scale introduced herein with respect to FIGS. 12D-12H, sensors that were healthy had a damage level of 0. Sensors that were slightly damaged had a damage level between 1 and 4. Sensors that were badly damaged had a damage level greater than 5.

FIG. 34 is a plot showing example results of the experiment indicating a MARD with impedance compensation versus a MARD based on factory calibration. On the horizontal axis, which shows MARD based on factory calibration, it will be observed that sensors that health sensors generally exhibited a MARD of less than 10. Slightly damaged sensors generally exhibited a MARD of less than 50, with badly damaged sensors exhibiting MARDs of around 40 and above. The vertical axis shows sensor MARDs for the indicated sensors with impedance compensation. As shown, all of the healthy and slightly damaged sensors show MARDs of about 10 or less, which may be suitable for use.

FIG. 35 is a plot showing example results of an experiment indicating sensor MARD with impedance compensation versus impedance deviation from a healthy baseline. Impedance deviation from the healthy baseline is a threshold describing how much lower the impedance of a sensor can be than the healthy baseline impedance before the sensor is unsuitable for use. FIG. 35 shows a first threshold 3502. As shown, all of the healthy sensors to the left of the first threshold 3502 have a MARD of less than 10. With compensation, however, slightly damaged sensors above the first threshold 3502 also have a MARD of less than 10. Accordingly, the use of impedance compensation, as described herein, may make it possible to increase sensor yield by utilizing a higher, second threshold 3504 that passes more sensors. For example, sensors with impedance deviations less than the second threshold 3504 may exhibit acceptable MARDs (e.g., less than 10). This allows slightly damaged sensors that might otherwise have been discarded to be used and provide suitable accuracy.

FIG. 36 is an example plot of the experiment described herein showing sensor impedance at three minutes from insertion versus glucose slope. The glucose slope indicates a relationship between sensor current (in picoamps) and the corresponding glucose concentration at the sensor (in mg/dL).

FIG. 36 also shows a healthy line 3602 that indicates a threshold for passing sensors. For example, sensors within a threshold distance of the healthy line 3602 are passed for use while sensors that are more than a threshold distance are not passed and may be discarded. In the example experiment described by FIG. 36, the use of impedance adjusted sensitivity allowed the healthy line to be shifted by 17% to generate a 17% line 3604. Sensors within the threshold of the 17% line exhibit acceptable accuracy and may be passed for use.

Each of these non-limiting examples in any portion of the above description may stand on its own or may be combined in various permutations or combinations with one or more of the other examples.

The above detailed description includes references to the accompanying drawings, which form a part of the detailed description. The drawings show, by way of illustration, specific embodiments in which the subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," "third," etc., are used merely as labels, and are not intended to impose numerical requirements on their objects.

Geometric terms, such as "parallel", "perpendicular", "round", or "square" are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the subject matter should be determined with reference to the claims, along with the full scope of equivalents to which such claims are entitled.

What is claimed is:

1. A method of assessing sensor membrane integrity using sensor electronics, comprising:
    applying a voltage to an analyte sensor using the sensor electronics;
    measuring a response to the voltage applied using the sensor electronics;
    determining an impedance parameter of the analyte sensor based on the response measured by the sensor electronics; and
    determining a membrane integrity state of the analyte sensor based on the impedance parameter, wherein the determined impedance parameter includes a comparison that determines an existence or an amount of a kickback.

2. The method of claim 1, wherein determining the membrane integrity state includes determining whether an impedance condition has been satisfied.

3. The method of claim 2, wherein determining whether the impedance condition has been satisfied includes determining when the impedance parameter is below a specified threshold.

4. The method of claim 2, further comprising alerting a user to replace a sensor responsive to the impedance condition being satisfied.

5. The method of claim 1, wherein determining the membrane integrity state includes determining a level of membrane damage or abnormality.

6. The method of claim 5, comprising compensating an estimated analyte concentration level based at least in part on a determined level of membrane damage or abnormality.

7. The method of claim 6, comprising compensating the estimated analyte concentration level by adjusting a sensitivity value based on the determined level.

8. The method of claim 1, comprising determining the impedance parameter at a specified frequency.

9. The method of claim 8, comprising determining the impedance parameter at a frequency above 100 Hz.

10. The method of claim 9, comprising determining the impedance at a frequency between 100 Hz and 10,000 Hz.

11. The method of claim 1, wherein the determined impedance parameter is an impedance of the analyte sensor after hydration.

12. The method of claim 1, wherein the determined impedance parameter is a determined impedance of a membrane portion of an analyte sensor after hydration.

13. The method of claim 1, wherein the comparison compares an impedance at a first frequency and an impedance at a second frequency.

14. The method of claim 13, wherein the comparison between an impedance at the first frequency and the impedance at the second frequency becomes stable after hydration.

15. The method of claim 13, wherein the first frequency and second frequency provide a relatively pronounced impedance difference.

16. The method of claim 13, wherein the comparison between the impedance at the first frequency and the impedance at the second frequency is a difference between the impedance at the first frequency and the impedance at the second frequency.

17. The method of claim 13, wherein the kickback is in a dual frequency impedance vs time relationship.

18. The method of claim 1, comprising determining the impedance parameter based on a measurement a specified time after hydration of the sensor.

19. The method of claim 18, wherein the specified time is between 5 and 600 seconds after hydration.

20. The method of claim 1, comprising determining the impedance parameter based on a measurement after a measured parameter has reached a steady state condition.

21. The method of claim 1, wherein the impedance parameter is a first derivative of impedance with respect to time.

22. The method of claim 21, comprising determining the membrane integrity state based on a shape of a first derivative vs. time curve.

23. The method of claim 1, wherein the impedance parameter is a second derivative of impedance with respect to time.

24. The method of claim 1, wherein determining the membrane integrity state is based at least in part on a fitted membrane resistance determined using a constant phase element model.

25. The method of claim 1, wherein determining a membrane integrity state includes performing a template match.

26. The method of claim 25, further comprising determining a best fit from a plurality of templates.

27. The method of claim 26, wherein determining a best fit includes using dynamic time warping.

28. An analyte sensor system comprising:
an analyte sensor sized and shaped for insertion into a host; and
sensor electronics coupled to the analyte sensor, the sensor electronics to:
apply a voltage to the analyte sensor;
measure a response to the voltage applied;
determine an impedance parameter of the analyte sensor based on the response; and
determine a membrane integrity state of the analyte sensor based on the impedance parameter, wherein the impedance parameter includes a comparison that determines an existence or an amount of a kickback.

29. The analyte sensor system of claim 28, wherein the impedance parameter is an impedance value and the sensor electronics determine whether the impedance value is below a threshold, wherein an impedance value below the threshold indicates a presence of damage or abnormality in a sensor membrane portion of the analyte sensor.

30. The analyte sensor system of claim 28, wherein the sensor electronics determine a level of membrane damage or abnormality based on the impedance parameter, and compensate an estimated analyte concentration level based at least in part on the level of membrane damage or abnormality.

31. The analyte sensor system of claim 28, wherein the sensor electronics determine the impedance parameter by applying a voltage signal at a specified frequency.

32. The analyte system of claim 31, wherein the sensor electronics determine the impedance parameter at frequency between 100 Hz and 10,000 Hz.

33. The analyte sensor system of claim 31, wherein the comparison compares an impedance at a first frequency and an impedance at a second frequency.

34. The analyte sensor system of claim 33, wherein the impedance parameter is a difference between an impedance at a first frequency and an impedance at a second frequency.

35. The analyte sensor system of claim 33, wherein the kickback is in a dual frequency impedance vs. time relationship; and
the sensor electronics determine the existence or amount of membrane damage based on the existence or amount of kickback.

36. The analyte sensor system of claim 28, wherein the sensor electronics determine a first derivative of impedance with respect to time and determine the membrane integrity state based on a value of the first derivative or a shape of a first derivative vs. time curve.

37. The analyte sensor system of claim 28, wherein the sensor electronics determine a second derivative of impedance with respect to time;
and determine the membrane integrity state based on a value of the second derivative.

38. The analyte sensor system of claim 28, wherein the sensor electronics match an impedance curve to a template.

39. The analyte sensor system of claim 38, wherein the sensor electronics perform dynamic time warping to determine a template match.

40. A method of operating an analyte sensor system comprising:
applying a voltage to an analyte sensor using sensor electronics;
measuring a response to the voltage applied using the sensor electronics;
determining an impedance parameter of the analyte sensor;
determining membrane state based on the impedance parameter based on the response measured by the sensor electronics, wherein the determined impedance parameter includes a comparison that determines an existence or an amount of a kickback; and
compensating an analyte concentration level based on the membrane state.

41. The method of claim 40, wherein the impedance parameter is an estimated membrane impedance.

42. The method of claim 40, wherein the impedance parameter is an impedance at a specified frequency.

43. The method of claim 40, wherein the impedance parameter is a dual frequency impedance.

44. The method of claim 40, further comprising determining when the impedance parameter is in a steady state and compensating based on the impedance parameter in the steady state.

45. The method of claim 40, wherein the kickback is in a dual frequency impedance vs. time relationship and determining an amount of compensation based on the existence or the amount of the kickback.

46. The method of claim 40, wherein the impedance parameter is a first derivative of impedance with respect to time.

47. The method of claim 40, wherein the impedance parameter is a second derivative of impedance with respect to time.

48. An analyte sensor system comprising:
    an analyte sensor sized and shaped for insertion into a host; and
    sensor electronics coupled to the analyte sensor, the sensor electronics to:
    apply a voltage to the analyte sensor;
    measure a response to the voltage applied;
    determine an impedance parameter of the analyte sensor based on the response, wherein the impedance parameter includes a comparison that determines an existence or an amount of a kickback; and
    compensate an analyte concentration level based on the impedance parameter to compensate for damage or abnormality in a membrane.

49. The analyte sensor system of claim 48, wherein the impedance parameter is an estimated membrane impedance.

50. The analyte sensor system of claim 48, wherein the impedance parameter is an impedance at a specified frequency.

51. The analyte sensor system of claim 48, wherein the impedance parameter is a dual frequency impedance.

52. The analyte sensor system of claim 48, wherein the impedance parameter is a first derivative of impedance with respect to time.

53. The analyte sensor system of claim 48, wherein the impedance parameter is a second derivative of impedance with respect to time.

54. The analyte sensor system of claim 48, wherein the sensor electronics determine when the impedance parameter is in a steady state and compensate based on the steady state impedance parameter.

55. The analyte sensor system of claim 48, wherein the kickback is in a dual frequency impedance vs. time relationship and the sensor electronics determine an amount of compensation based on the existence or amount of kickback.

* * * * *

UNITED STATES PATENT AND TRADEMARK OFFICE
CERTIFICATE OF CORRECTION

| | | |
|---|---|---|
| PATENT NO. | : 11,963,767 B2 | Page 1 of 1 |
| APPLICATION NO. | : 16/729021 | |
| DATED | : April 23, 2024 | |
| INVENTOR(S) | : Bohm et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 547 days.

Signed and Sealed this
Twenty-fifth Day of March, 2025

Coke Morgan Stewart
*Acting Director of the United States Patent and Trademark Office*